United States Patent
Hogan et al.

(10) Patent No.: US 8,431,384 B2
(45) Date of Patent: Apr. 30, 2013

(54) STABLE PROTEIN STORAGE AND STABLE NUCLEIC ACID STORAGE IN RECOVERABLE FORM

(75) Inventors: Michael Hogan, Tucson, AZ (US); James C. Davis, Plymouth, MA (US)

(73) Assignee: GenVault Corporation, Pleasanton, CA (US)

( * ) Notice: Subject to any disclaimer, the term of this patent is extended or adjusted under 35 U.S.C. 154(b) by 851 days.

(21) Appl. No.: 12/499,031

(22) Filed: Jul. 7, 2009

(65) Prior Publication Data

US 2010/0178210 A1 Jul. 15, 2010

Related U.S. Application Data

(62) Division of application No. 11/137,806, filed on May 24, 2005, now Pat. No. 7,589,184.

(60) Provisional application No. 60/574,274, filed on May 24, 2004.

(51) Int. Cl.
*C12M 3/00* (2006.01)
*C07H 21/04* (2006.01)
*C07K 14/00* (2006.01)

(52) U.S. Cl.
USPC ............................ 435/283.1; 536/23.1; 514/2

(58) Field of Classification Search .................. None
See application file for complete search history.

(56) References Cited

U.S. PATENT DOCUMENTS

| | | | |
|---|---|---|---|
| 2,938,794 A | 5/1960 | Herman |
| 4,292,920 A | 10/1981 | Smith et al. |
| 4,643,879 A | 2/1987 | Hanaway |
| 4,684,613 A | 8/1987 | Barrere et al. |
| 4,767,716 A | 8/1988 | Sakamaki et al. |
| 4,824,641 A | 4/1989 | Williams |
| 4,891,319 A * | 1/1990 | Roser ........................... 435/188 |
| 4,896,024 A | 1/1990 | Morello et al. |
| 5,011,779 A | 4/1991 | Maimon |
| 5,034,506 A | 7/1991 | Summerton et al. |
| 5,096,676 A | 3/1992 | McPherson et al. |
| 5,102,804 A | 4/1992 | Fischer et al. |
| 5,120,662 A | 6/1992 | Chan et al. |
| 5,125,240 A | 6/1992 | Knippscheer et al. |
| 5,139,744 A | 8/1992 | Kowalski |
| 5,141,868 A | 8/1992 | Shanks et al. |
| 5,223,618 A | 6/1993 | Cook et al. |
| 5,355,304 A | 10/1994 | DeMoranville et al. |
| 5,366,896 A | 11/1994 | Margrey et al. |
| 5,378,825 A | 1/1995 | Cook et al. |
| 5,411,065 A | 5/1995 | Meador et al. |
| 5,411,893 A | 5/1995 | Eden et al. |
| 5,424,036 A | 6/1995 | Ushikubo |
| 5,441,698 A | 8/1995 | Norell |
| 5,445,294 A | 8/1995 | Gardner et al. |
| 5,460,057 A | 10/1995 | Ostrup |
| 5,496,562 A | 3/1996 | Burgoyne |
| 5,516,487 A | 5/1996 | Rosenthal et al. |
| 5,631,844 A | 5/1997 | Margrey |
| 5,637,508 A | 6/1997 | Kidwell et al. |
| 5,638,170 A | 6/1997 | Trinka et al. |
| 5,736,332 A | 4/1998 | Mandecki |
| 5,756,126 A | 5/1998 | Burgoyne |
| 5,800,777 A | 9/1998 | Jehan |
| 5,800,785 A | 9/1998 | Bochner |
| 5,805,456 A | 9/1998 | Higham et al. |
| 5,807,527 A | 9/1998 | Burgoyne |
| 5,841,975 A | 11/1998 | Layne et al. |
| 5,850,442 A | 12/1998 | Muftic |
| 5,853,666 A | 12/1998 | Seaton et al. |
| 5,912,128 A | 6/1999 | Lal et al. |
| 5,916,812 A | 6/1999 | Chen et al. |
| 5,920,871 A | 7/1999 | Macri et al. |
| 5,922,617 A | 7/1999 | Wang et al. |
| 5,955,448 A | 9/1999 | Colaco et al. |
| 5,968,731 A | 10/1999 | Layne |
| 5,981,166 A | 11/1999 | Mandecki |
| 5,984,116 A | 11/1999 | Babbs |
| 5,985,214 A | 11/1999 | Stylli et al. |
| 5,985,217 A | 11/1999 | Krulevitch |
| 5,993,387 A | 11/1999 | Moore |
| 6,007,779 A | 12/1999 | Lemieux et al. |
| 6,086,824 A | 7/2000 | Fanning et al. |
| 6,098,819 A | 8/2000 | Link |
| 6,103,518 A | 8/2000 | Leighton |
| 6,108,588 A | 8/2000 | McGrady |
| 6,110,748 A | 8/2000 | Reber et al. |
| 6,127,928 A | 10/2000 | Issacman et al. |
| 6,132,685 A | 10/2000 | Kercso et al. |
| 6,156,565 A | 12/2000 | Maes et al. |
| 6,159,425 A | 12/2000 | Edwards et al. |
| 6,182,719 B1 | 2/2001 | Yahiro |
| 6,221,575 B1 | 4/2001 | Roser et al. |
| 6,245,295 B1 | 6/2001 | Chen et al. |
| 6,251,343 B1 | 6/2001 | Dubrow et al. |
| 6,260,024 B1 | 7/2001 | Shkedy |
| 6,265,219 B1 | 7/2001 | Giger et al. |
| 6,274,374 B1 | 8/2001 | Astle |
| 6,294,203 B1 | 9/2001 | Burgoyne |

(Continued)

FOREIGN PATENT DOCUMENTS

DE 19716154 A1 10/1998
EP 0198413 A2 10/1986

(Continued)

OTHER PUBLICATIONS

Perry-O'Keefe H et al., Peptide nucleic acid pre-gel hybridization: an alternative to southern hybridization. Proc Natl Acad Sci USA. 93(25):14670-5 (1996).

(Continued)

*Primary Examiner* — Anand Desai

(57) ABSTRACT

The invention provides compositions and methods for storage of biomolecules. The biomolecules are stored via absorption to a substrate. Absorbed biomolecules can be eluted or recovered from the substrate at a future time, and optionally be subjected to a subsequent analysis or application. Biomolecules absorbed to a substrate for storage may also optionally be preserved, i.e., the absorbed biomolecule is resistant to or resists degradation.

11 Claims, 38 Drawing Sheets

U.S. PATENT DOCUMENTS

| | | |
|---|---|---|
| 6,313,102 B1 | 11/2001 | Colaco et al. |
| 6,325,114 B1 | 12/2001 | Bevirt et al. |
| 6,350,620 B2 | 2/2002 | Chang et al. |
| 6,358,470 B1 | 3/2002 | Higuchi |
| 6,362,737 B1 | 3/2002 | Rodgers et al. |
| 6,366,682 B1 | 4/2002 | Hoffman et al. |
| 6,372,185 B1 | 4/2002 | Shumate et al. |
| 6,395,231 B1 | 5/2002 | Kraemer et al. |
| 6,402,837 B1 | 6/2002 | Shtrahman et al. |
| 6,408,878 B2 | 6/2002 | Unger et al. |
| 6,416,719 B1 | 7/2002 | Fawcett et al. |
| 6,418,416 B1 | 7/2002 | Rosenberg et al. |
| 6,464,942 B2 | 10/2002 | Coffman et al. |
| 6,472,218 B1 | 10/2002 | Stylli et al. |
| 6,485,690 B1 | 11/2002 | Pfost et al. |
| 6,485,978 B1 | 11/2002 | Kirckof et al. |
| 6,493,724 B1 | 12/2002 | Cusack et al. |
| 6,508,984 B1 | 1/2003 | Turner et al. |
| 6,518,060 B2 | 2/2003 | Heimberg et al. |
| 6,534,015 B1 | 3/2003 | Viot et al. |
| 6,556,923 B2 | 4/2003 | Gallagher et al. |
| 6,649,386 B2 | 11/2003 | Roser |
| 6,649,403 B1 | 11/2003 | McDevitt et al. |
| 6,652,724 B2 | 11/2003 | Michael et al. |
| 6,678,577 B1 | 1/2004 | Stylli et al. |
| 6,685,884 B2 | 2/2004 | Stylli et al. |
| 6,685,940 B2 | 2/2004 | Andya et al. |
| 6,686,158 B2 | 2/2004 | Mandecki |
| 6,689,755 B1 | 2/2004 | Gabel et al. |
| 6,699,710 B1 | 3/2004 | Kononen et al. |
| 6,752,967 B2 | 6/2004 | Farina et al. |
| 6,767,748 B2 | 7/2004 | Yokokawa et al. |
| 6,811,752 B2 | 11/2004 | Barbera-Guillem |
| 6,943,035 B1 | 9/2005 | Davies et al. |
| 7,142,987 B2 | 11/2006 | Eggers |
| 7,225,082 B1 | 5/2007 | Natan et al. |
| 7,276,208 B2 | 10/2007 | Sevigny et al. |
| 7,312,085 B2 | 12/2007 | Chou et al. |
| 7,354,774 B2 | 4/2008 | Hughes et al. |
| 7,589,184 B2 | 9/2009 | Hogan et al. |
| 2002/0006673 A1 | 1/2002 | Mandecki |
| 2002/0176803 A1 | 11/2002 | Hamel et al. |
| 2003/0000597 A1 | 1/2003 | Ganz et al. |
| 2003/0027788 A1 | 2/2003 | Singh et al. |
| 2003/0044991 A1 | 3/2003 | Haslam et al. |
| 2003/0046114 A1 | 3/2003 | Davies |
| 2003/0087425 A1 | 5/2003 | Eggers |
| 2003/0087455 A1 | 5/2003 | Eggers et al. |
| 2003/0088657 A1 | 5/2003 | Eggers |
| 2003/0129089 A1 | 7/2003 | Arnold et al. |
| 2003/0129755 A1 | 7/2003 | Sadler et al. |
| 2003/0161761 A1 | 8/2003 | Williams et al. |
| 2003/0215361 A1 | 11/2003 | Jang |
| 2003/0215369 A1 | 11/2003 | Eggers et al. |
| 2004/0014228 A1 | 1/2004 | Brignac et al. |
| 2004/0053318 A1 | 3/2004 | McWilliams et al. |
| 2004/0098204 A1 | 5/2004 | Milosavljevic et al. |
| 2004/0101966 A1 | 5/2004 | Davis et al. |
| 2004/0142893 A1 | 7/2004 | Ikeda et al. |
| 2004/0219533 A1 | 11/2004 | Davis et al. |
| 2004/0229038 A1 | 11/2004 | Cooper et al. |
| 2005/0026181 A1 | 2/2005 | Davis et al. |
| 2005/0074478 A1 | 4/2005 | Ofstead et al. |
| 2008/0050793 A1 | 2/2008 | Durance et al. |
| 2009/0212260 A1 | 8/2009 | Paknikar |
| 2010/0062418 A1 | 3/2010 | Mach et al. |
| 2010/0087352 A1 | 4/2010 | Mason |
| 2010/0209957 A1 | 8/2010 | Hogan et al. |
| 2010/0218623 A1 | 9/2010 | Eggers et al. |
| 2010/0248363 A1 | 9/2010 | Hogan et al. |

FOREIGN PATENT DOCUMENTS

| | | |
|---|---|---|
| EP | 0198413 A3 | 12/1987 |
| EP | 1155742 A2 | 11/2001 |
| EP | 1155742 A3 | 1/2002 |
| EP | 1179585 A2 | 2/2002 |
| EP | 1179585 A3 | 3/2002 |
| EP | 1965326 A2 | 9/2008 |
| EP | 1965326 A3 | 12/2008 |
| GB | 2369086 A | 2/2002 |
| GB | 2380259 A | 4/2003 |
| JP | 1078388 A | 3/1998 |
| JP | 2002-125656 A | 5/2002 |
| JP | 2008275648 | 11/2008 |
| WO | WO 87/00196 A1 | 1/1987 |
| WO | WO 94/11388 A1 | 5/1994 |
| WO | WO 96/11406 A1 | 4/1996 |
| WO | WO 96/40077 A2 | 12/1996 |
| WO | WO 96/40077 A3 | 1/1997 |
| WO | 98/10787 | 3/1998 |
| WO | 98/10792 | 3/1998 |
| WO | WO 98/13684 A1 | 4/1998 |
| WO | WO 98/20019 A1 | 5/1998 |
| WO | WO 98/10787 A3 | 7/1998 |
| WO | WO 98/29736 A1 | 7/1998 |
| WO | 98/47516 | 10/1998 |
| WO | WO 99/34214 A1 | 7/1999 |
| WO | WO 99/38962 A2 | 8/1999 |
| WO | WO 99/39716 A1 | 8/1999 |
| WO | WO 99/44062 A1 | 9/1999 |
| WO | WO 99/38962 A3 | 10/1999 |
| WO | 00/09150 | 2/2000 |
| WO | 00/23478 | 4/2000 |
| WO | WO 00/09150 A3 | 5/2000 |
| WO | 00/35472 | 6/2000 |
| WO | 00/42030 | 7/2000 |
| WO | WO 00/48735 A2 | 8/2000 |
| WO | WO 00/49382 A2 | 8/2000 |
| WO | WO 00/35472 A3 | 11/2000 |
| WO | WO 00/66360 A1 | 11/2000 |
| WO | WO 00/48735 A3 | 12/2000 |
| WO | WO 00/49382 A3 | 1/2001 |
| WO | WO 01/12327 A1 | 2/2001 |
| WO | WO 01/31317 A1 | 5/2001 |
| WO | WO 01/31333 A1 | 5/2001 |
| WO | WO 01/42796 A1 | 6/2001 |
| WO | WO 01/86410 A1 | 11/2001 |
| WO | WO 01/94016 A1 | 12/2001 |
| WO | WO 02/46719 A3 | 2/2002 |
| WO | WO 02/30561 A2 | 4/2002 |
| WO | WO 02/46719 A2 | 6/2002 |
| WO | 03020924 A2 | 3/2003 |
| WO | WO 03/022435 A2 | 3/2003 |
| WO | WO 03/031929 A2 | 4/2003 |
| WO | WO 02/30561 A3 | 5/2003 |
| WO | WO 03/039749 A2 | 5/2003 |
| WO | WO 03/049861 A1 | 6/2003 |
| WO | WO 03/020924 A3 | 7/2003 |
| WO | WO 03/031929 A3 | 8/2003 |
| WO | WO 03/022435 A3 | 12/2003 |
| WO | WO 03/039749 A3 | 2/2004 |
| WO | 2004/033470 A2 | 4/2004 |
| WO | WO 2004/033470 A3 | 9/2004 |
| WO | WO 2005/116081 A2 | 12/2005 |
| WO | WO 2005/116081 A3 | 7/2006 |

OTHER PUBLICATIONS

International search report dated May 18, 2006 for PCT/US2005/018092.

U.S. Appl. No. 13/081,436, filed Apr. 6, 2011, Saghbini et al.

Belgrader, et al. Coupled DNA Purification and PCR Amplication of STR Loci from Bloodstain Cards using a Robotic System. BioTechniques. 1995; 19:427-432.

Bever, et al. Implementation of Laboratory Automation for the Analysis of STR Loci. 8th International Symposium on Human ID. 1997.

Elliot, et al. Extraction of DNA from FTA Blood Stain Collection Cards for Construction of a Large STR National DNA Data Base. 8th International Symposium on Human ID. 1997.

European office action dated Mar. 14, 2006 for EP 02792241.8.

European office action dated May 9, 2008 for EP 02776478.6.

European office action dated May 10, 2006 for EP 02776478.6.

European office action dated May 19, 2008 for EP 05754240.9.

European office action dated Sep. 21, 2004 for EP 02776478.6.

European search report dated Jun. 16, 2011 for EP 03812020.0.
European search report dated Dec. 6, 2010 for EP 03736489.0.
Final Office Action dated Jan. 5, 2006 for U.S. Appl. No. 10/150,771.
Final Office Action dated Mar. 31, 2005 for U.S. Appl. No. 10/007,355.
Final Office Action dated Jul. 11, 2007 for U.S. Appl. No. 10/150,771.
Final Office Action dated Jul. 21, 2005 for U.S. Appl. No. 10/150,771.
Final Office Action dated Sep. 24, 2008 for U.S. Appl. No. 10/150,771.
Final Office Action dated Sep. 25, 2009 for U.S. Appl. No. 10/150,771.
Final Office Action dated Oct. 8, 2012 for U.S. Appl. No. 12/732,154.
Final Office Action dated Dec. 8, 2005 for U.S. Appl. No. 10/007,355.
Final Office Action dated Dec. 16, 2009 for U.S. Appl. No. 10/007,355.
Hansen, et al. Sample Archiving of Bacterial and Plasmid DNAs for Future Use. Focus. 1998; 20(3):72-74.
International search report dated Feb. 17, 2010 for PCT/US2009/048187.
International search report dated Feb. 26, 2004 for PCT/US2002/036101.
International search report dated Mar. 19, 2003 for PCT/US2002/036099.
International search report dated Apr. 13, 2004 for PCT/US2003/028437.
International search report dated May 5, 2005 for PCT/US2003/032611.
International search report dated May 31, 2010 for PCT/US2009/056869.
International search report dated Jul. 30, 2003 for PCT/US2003/012852.
International Search Report dated Aug. 22, 2003 for PCT/US2003/012850.
International Search Report dated Oct. 12, 2003 for PCT/US2002/036108.
International search report and written opinion dated Aug. 9, 2011 for PCT/US2011/031477.
Office Action dated Jan. 31, 2006 for U.S. Appl. No. 10/252,352.
Office Action dated Feb. 1, 2007 for U.S. Appl. No. 10/150,771.
Office Action dated Feb. 2, 2009 for U.S. Appl. No. 10/252,352.
Office Action dated Feb. 12, 2008 for U.S. Appl. No. 10/150,771.
Office Action dated Feb. 15, 2006 for U.S. Appl. No. 10/005,415.
Office Action dated Feb. 26, 2008 for U.S. Appl. No. 11/137,806.
Office Action dated Mar. 4, 2008 for U.S. Appl. No. 10/005,415.
Office Action dated Mar. 22, 2006 for U.S. Appl. No. 10/150,770.
Office Action dated Mar. 22, 2006 for U.S. Appl. No. 10/302,647.
Office Action dated Mar. 24, 2004 for U.S. Appl. No. 10/252,352.
Office Action dated Apr. 2, 2009 for U.S. Appl. No. 10/302,647.
Office Action dated Apr. 4, 2007 for U.S. Appl. No. 10/150,770.
Office Action dated Apr. 5, 2005 for U.S. Appl. No. 10/252,352.
Office Action dated Apr. 23, 2009 for U.S. Appl. No. 10/007,355.
Office Action dated Jun. 13, 2005 for U.S. Appl. No. 10/005,415.
Office Action dated Jun. 25, 2008 for U.S. Appl. No. 10/302,647.
Office Action dated Jun. 30, 2005 for U.S. Appl. No. 10/005,529.
Office Action dated Aug. 28, 2006 for U.S. Appl. No. 10/005,415.
Office Action dated Sep. 2, 2008 for U.S. Appl. No. 10/005,415.
Office Action dated Sep. 6, 2006 for U.S. Appl. No. 10/302,647.
Office Action dated Sep. 8, 2006 for U.S. Appl. No. 10/150,770.
Office Action dated Sep. 12, 2007 for U.S. Appl. No. 10/005,415.
Office Action dated Sep. 13, 2004 for U.S. Appl. No. 10/007,355.
Office Action dated Sep. 16, 2004 for U.S. Appl. No. 10/252,352.
Office Action dated Sep. 25, 2008 for U.S. Appl. No. 11/137,806.
Office Action dated Oct. 3, 2007 for U.S. Appl. No. 10/302,647.
Office Action dated Oct. 14, 2004 for U.S. Appl. No. 10/150,771.
Office Action dated Oct. 17, 2007 for U.S. Appl. No. 10/150,770.
Office Action dated Nov. 4, 2004 for U.S. Appl. No. 10/005,529.
Zhang, et al. Single gene retrieval from thermally degraded DNA. J Biosci. Dec. 2005; 30:599-604.
Canadian office action dated Mar. 5, 2012 for CA Application No. 2,567,720.
Harty, et al. Collection of buccal cell DNA using treated cards. Cancer Epidemiol Biomarkers Prev. May 2000;9(5):501-6.
Nokes, et al. A comparison of oral fluid and serum for the detection of rubella-specific antibodies in a community study in Addis Ababa, Ethiopia. Trop Med Int Health. Apr. 1998;3(4):258-67.
Nokes, et al. An evaluation of oral-fluid collection devices for the determination of rubella antibody status in a rural Ethiopian community. Trans R Soc Trop Med Hyg. Nov.-Dec. 1998;92(6):679-85.
Ware, et al. Comparison of sponging and excising as sampling procedures for microbiological analysis of fresh beef-carcass tissue. J Food Prot. Nov. 1999;62(11):1255-9.
Zhong, et al. Comparison of IsoCode STIX and FTA Gene Guard collection matrices as whole-blood storage and processing devices for diagnosis of malaria by PCR. J Clin Microbiol. Mar. 2001;39(3):1195-6.

* cited by examiner

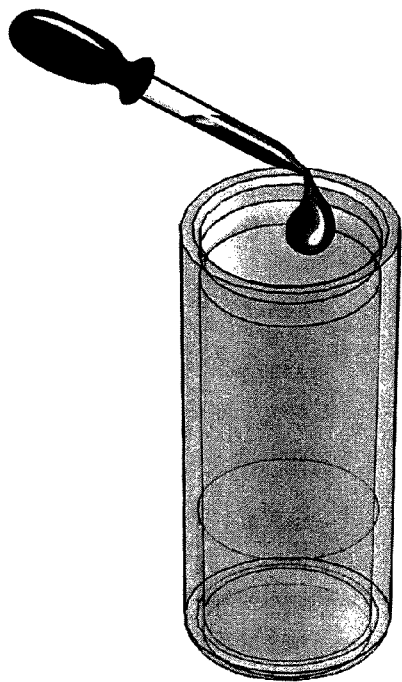 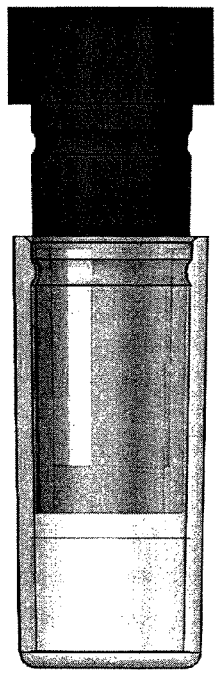
Apply sample & dry down	Cap for storage
Figure 2
Storage Unit with sponge showing addition of sample, drying and capped storage format.

After sample selection the absorbed plasma sample is hydrated and the cap/plunger is used to compress the sponge and elute the plasma.

Figure 6

1. Alpha-2 Macroglobulin – mg/ml
2. Alpha-Fetoprotein – ng/ml
3. Apolipoprotein A1 – mg/ml
4. Apolipoprotein CIII – ug/ml
5. Apolipoprotein H – ug/ml
6. Beta-2 Microglobulin – ug/ml
7. Brain Derived Neurotrophic Factor – ng/ml
8. Complement 3 – mg/ml
9. C Reactive Protein – ug/?ml
10. ENA-78 – ng/ml
11. Factor VII – ng/ml
12. Ferritin – ng/ml
13. Fibrinogen – mg/ml
14. GM-CSF – pg/ml
15. Glutathione S-Transferase – ng/ml
16. ICAM-1 – ng/ml
17. IgA – mg/ml
18. IgM – mg/ml
19. IL-16 – pg/ml
20. Insulin – uIU/ml
21. Leptin – ng/ml
22. Lipoprotein (a) – ug/ml
23. MCP-1 – pg/ml
24. MDC – pg/ml
25. MIP-1 beta – pg/ml
26. MMP-3 – ng/ml
27. MMP-9 – ng/ml
28. Myoglobin – ng/ml
29. Prostatic Acid Phosphatase – ng/ml
30. Prostate Specific Antigen, Free – ng/ml
31. RANTES – ng/ml
32. SGOT – ug/ml
33. Thyroxine Binding Globulin – ug/ml
34. TIMP-1 – ng/ml
35. Thrombopoietin – ng/ml
36. Thyroid Stimulating Hormone – uIU/ml
37. von Willebrand Factor – ug/ml

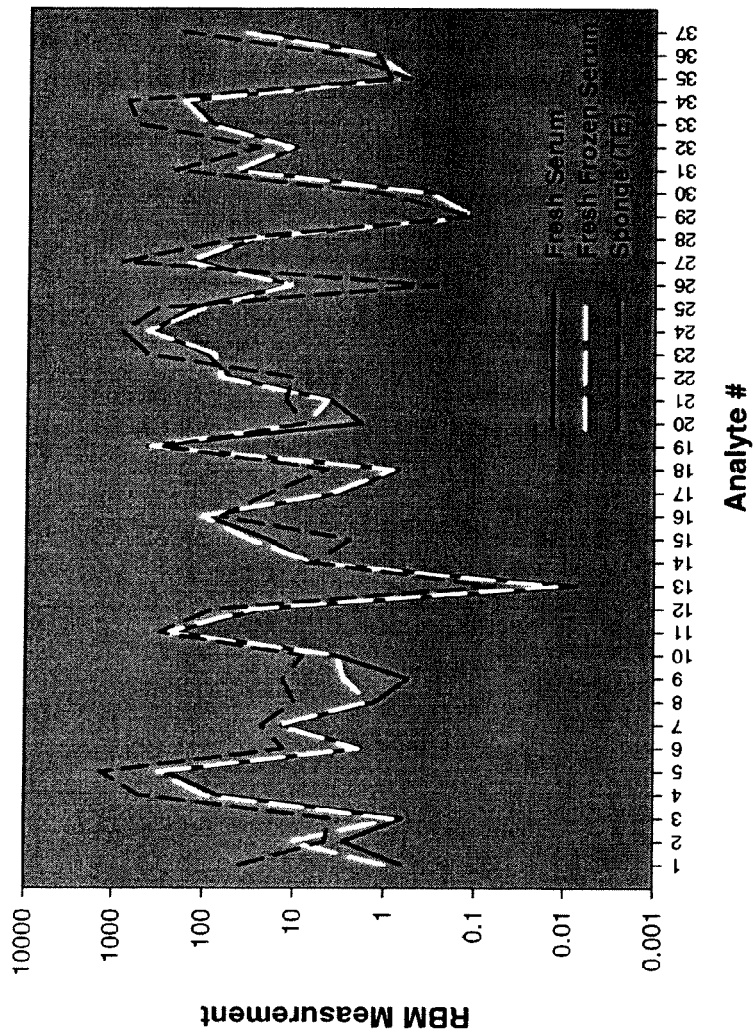

Day 7
Serum on Sponge (TE)
Room Temperature
vs
Fresh Serum and Fresh Frozen Serum

Figure 13

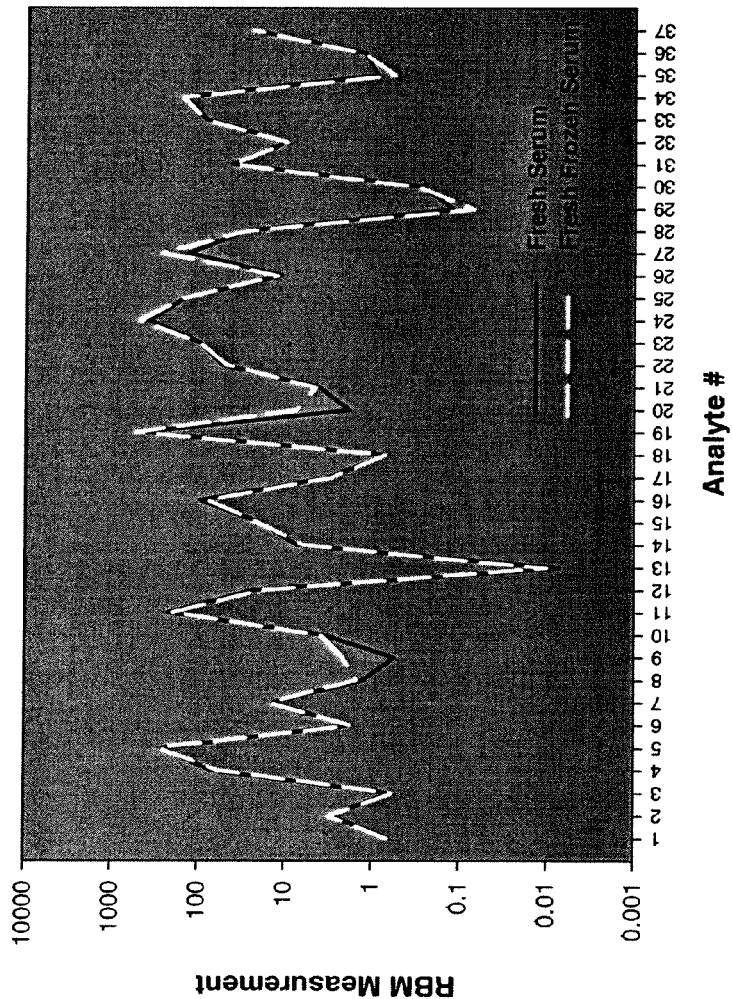

1. Alpha-2 Macroglobulin – mg/ml
2. Alpha-Fetoprotein – ng/ml
3. Apolipoprotein A1 – mg/ml
4. Apolipoprotein CIII – ug/ml
5. Apolipoprotein H – ug/ml
6. Beta-2 Microglobulin – ug/ml
7. Brain Derived Neurotrophic Factor – ng/ml
8. Complement 3 – mg/ml
9. C Reactive Protein – ug/?ml
10. ENA-78 – ng/ml
11. Factor VII – ng/ml
12. Ferritin – ng/ml
13. Fibrinogen – mg/ml
14. GM-CSF – pg/ml
15. Glutathione S-Transferase – ng/ml
16. ICAM-1 – ng/ml
17. IgA – mg/ml
18. IgM – mg/ml
19. IL-16 – pg/ml
20. Insulin – uIU/ml
21. Leptin – ng/ml
22. Lipoprotein (a) – ug/ml
23. MCP-1 – pg/ml
24. MDC – pg/ml
25. MIP-1 beta – pg/ml
26. MMP-3 – ng/ml
27. MMP-9 – ng/ml
28. Myoglobin – ng/ml
29. Prostatic Acid Phosphatase – ng/ml
30. Prostate Specific Antigen, Free – ng/ml
31. RANTES – ng/ml
32. SGOT – ug/ml
33. Thyroxine Binding Globulin – ug/ml
34. TIMP-1 – ng/ml
35. Thrombopoietin – ng/ml
36. Thyroid Stimulating Hormone – uIU/ml
37. von Willebrand Factor – ug/ml

Figure 21

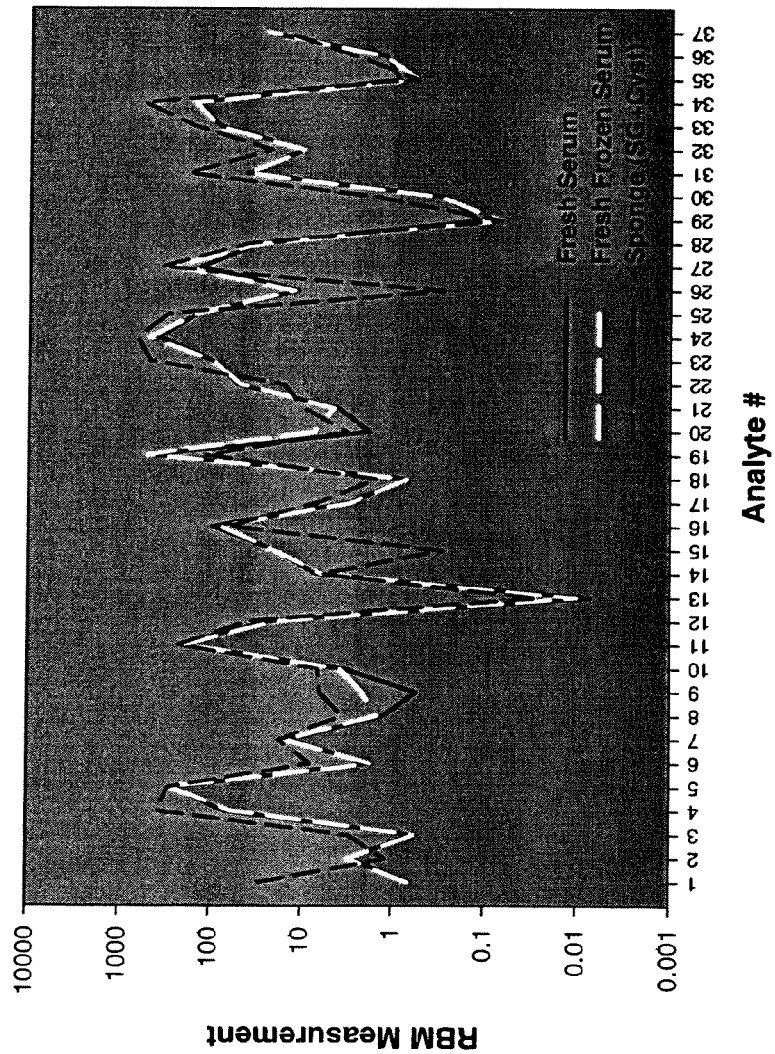

Day 55
Serum on Sponge (SG+Cyst)
Room Temperature
vs
Fresh Serum and Fresh Frozen Serum 1. Alpha-2 Macroglobulin – mg/ml
2. Alpha-Fetoprotein – ng/ml
3. Apolipoprotein A1 – mg/ml
4. Apolipoprotein CIII – ug/ml
5. Apolipoprotein H – ug/ml
6. Beta-2 Microglobulin – ug/ml
7. Brain Derived Neurotrophic Factor – ng/ml
8. Complement 3 – mg/ml
9. C Reactive Protein – ug/?ml
10. ENA-78 – ng/ml
11. Factor VII – ng/ml
12. Ferritin – ng/ml
13. Fibrinogen – mg/ml
14. GM-CSF – pg/ml
15. Glutathione S-Transferase – ng/ml
16. ICAM-1 – ng/ml
17. IgA – mg/ml
18. IgM – mg/ml
19. IL-16 – pg/ml
20. Insulin – uIU/ml
21. Leptin – ng/ml
22. Lipoprotein (a) – ug/ml
23. MCP-1 – pg/ml
24. MDC – pg/ml
25. MIP-1 beta – pg/ml
26. MMP-3 – ng/ml
27. MMP-9 – ng/ml
28. Myoglobin – ng/ml
29. Prostatic Acid Phosphatase – ng/ml
30. Prostate Specific Antigen, Free – ng/ml
31. RANTES – ng/ml
32. SGOT – ug/ml
33. Thyroxine Binding Globulin – ug/ml
34. TIMP-1 – ng/ml
35. Thrombopoietin – ng/ml
36. Thyroid Stimulating Hormone – uIU/ml
37. von Willebrand Factor – ug/ml

Figure 23

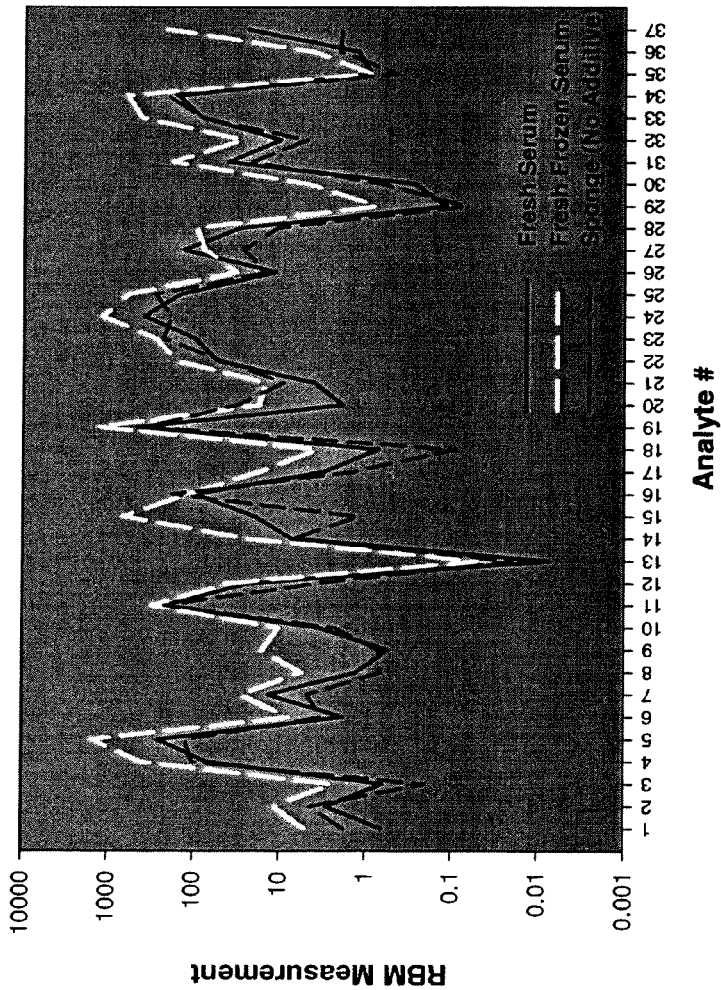

Day 187
Serum on Sponge (No Additive)
Room Temperature
vs
Fresh Serum vs Fresh Frozen Serum 1. Alpha-2 Macroglobulin – mg/ml
2. Alpha-Fetoprotein – ng/ml
3. Apolipoprotein A1 – mg/ml
4. Apolipoprotein CIII – ug/ml
5. Apolipoprotein H – ug/ml
6. Beta-2 Microglobulin – ug/ml
7. Brain Derived Neurotrophic Factor – ng/ml
8. Complement 3 – mg/ml
9. C Reactive Protein – ug/?ml
10. ENA-78 – ng/ml
11. Factor VII – ng/ml
12. Ferritin – ng/ml
13. Fibrinogen – mg/ml
14. GM-CSF – pg/ml
15. Glutathione S-Transferase – ng/ml
16. ICAM-1 – ng/ml
17. IgA – mg/ml
18. IgM – mg/ml
19. IL-16 – pg/ml
20. Insulin – uIU/ml
21. Leptin – ng/ml
22. Lipoprotein (a) – ug/ml
23. MCP-1 – pg/ml
24. MDC – pg/ml
25. MIP-1 beta – pg/ml
26. MMP-3 – ng/ml
27. MMP-9 – ng/ml
28. Myoglobin – ng/ml
29. Prostatic Acid Phosphatase – ng/ml
30. Prostate Specific Antigen, Free – ng/ml
31. RANTES – ng/ml
32. SGOT – ug/ml
33. Thyroxine Binding Globulin – ug/ml
34. TIMP-1 – ng/ml
35. Thrombopoietin – ng/ml
36. Thyroid Stimulating Hormone – uIU/ml
37. von Willebrand Factor – ug/ml Gel #8

558 bp amplicon screen of DNA extracted from
Day 167 Whole Blood on Polyester Sponge –

Q1 and Q2 are [1018] duplicate smpls of Qiagen-ext DNA from control whole blood never on sponge, frozen @ minus 20°C, 506 / 517 bp

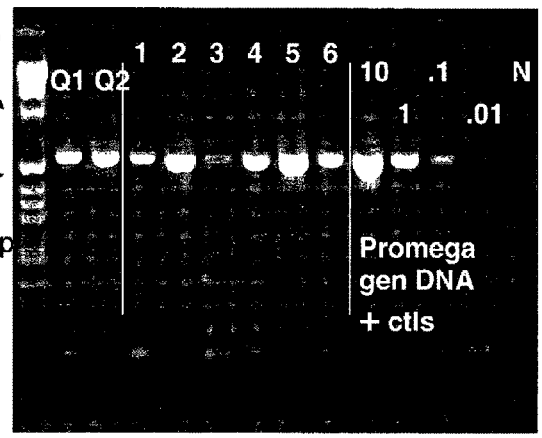

Q1 and Q2:
added 1 ul of 1:10 diln to 50 ul PCR reaction,
total elute = 200 ul 1 thru 6:
added 2 ul to PCR reaction,
total elute = 150 ul 1 = TE + NP40, no trehalose
2 = TE + NP40 + trehalose
3 = TE + SDS
4 = TE + SDS + trehalose
5 = Trehalose alone
6 = no additive NOTE: #3 was slightly hemolyzed in final elution 01-14-05 Bonnie
150V X 45 minutes
2%SFR + 1XTBE

Figure 38

US 8,431,384 B2

STABLE PROTEIN STORAGE AND STABLE NUCLEIC ACID STORAGE IN RECOVERABLE FORM

RELATED APPLICATIONS

This application claims priority to U.S. application Ser. No. 11/137,806, filed May 24, 2005, which claims priority to U.S. Application No. 60/574,274, filed May 24, 2004, the contents of which are incorporated by reference herein in their entirety.

INTRODUCTION

Proteins and nucleic acid are known for highly variable stability based upon their origin, structure and environment. Some proteins are highly stable even in hostile environments, such as digestive enzymes or thermally stable proteins found in organisms growing in fumaroles in the deep oceans. Others, such as cellular membrane proteins may have a solution half life measured in minutes. Most proteins fall in an intermediate range of stability that requires cold, frozen storage for long term stability.

SUMMARY

The invention is based, at least in part, upon compositions that can store biomolecules (e.g., peptide or nucleic acid alone, or in combination) in a form that is recoverable. Biomolecules (e.g., peptide or nucleic acid) stored as set forth herein can be preserved for days, weeks, months, and even longer periods of time, for example, years. Biomolecules (e.g., peptide or nucleic acid) can be stored at ambient temperatures, such that no freezing or refrigeration is required. The invention is also based, at least in part, upon stored biomolecules (e.g., peptide or nucleic acid) being in a form that resists degradation, i.e., the stored biomolecule (e.g., peptide or nucleic acid) is preserved during storage. Biomolecules stored in a preserved form that allows recovery of the biomolecule for a subsequent analysis or application. For example, a stored peptide can be recovered days, weeks, months or years after storage and subsequently analyzed. Even heating stored peptide at 50° C. for 90 days did not result in substantial degradation.

In accordance with the invention, in one embodiment, provided is a composition including a biomolecule (e.g., peptide or nucleic acid) and an elutable porous or semi-porous substrate (e.g., an elastomeric substrate), wherein the composition is substantially free of moisture (e.g., the moisture content is less than about 5%, 5-10%, 10-15%, 15-20%, or 20-25% water by mass) and the biomolecule (e.g., peptide or nucleic acid) is absorbed to the porous or semi-porous substrate (e.g., an elastomeric substrate), and the absorbed peptide is recoverable from the porous or semi-porous substrate (e.g., an elastomeric substrate). In one aspect the biomolecule adsorbed to the substrate comprises a peptide. In another aspect, the biomolecule adsorbed to the substrate comprises a nucleic acid. In yet another aspect, the biomolecule adsorbed to the substrate comprises a peptide and a nucleic acid.

In additional embodiments, a biomolecule (e.g., peptide or nucleic acid) adsorbed to an elutable porous or semi-porous substrate (e.g., an elastomeric substrate) resists degradation as compared to unabsorbed biomolecule (e.g., peptide or nucleic acid). In one aspect, peptide adsorbed to the substrate resists degradation as compared to unabsorbed peptide. In another aspect, nucleic acid adsorbed to the substrate resists degradation as compared to unabsorbed nucleic acid. In particular aspects, the resistance to degradation comprises a loss of no greater than 50-75%, 33-50%, 25-33%, 10-25%, or 5-15% of the biomolecule (e.g., peptide or nucleic acid), as compared to an equivalent amount of unabsorbed biomolecule (e.g., peptide or nucleic acid), over a period of time; or the resistance to degradation comprises preserving 33-50%, 50-75%, 75-90%, or 90-95% or more of the biomolecule (e.g., peptide or nucleic acid), as compared to an equivalent amount of unabsorbed biomolecule (e.g., peptide or nucleic acid), over a period of time, for example, for 5-10, 10-20, 20-30, 30-50, 50-90, 50-150, 150-365 days or weeks, or for 1, 2, 3, 4, 5, 6, 7, 8, 9, 10 years, or more (e.g., at ambient temperature, at −20° C., at 4° C., at 4-10° C., at 10-20° C., at 20-30° C., at 30-40° C., at 40-50° C., at 50-60° C., at 60-70° C., or at 70-80° C.). Degradation can be assessed, for example, by determining one or more of the quantity of the biomolecule (e.g., peptide or nucleic acid) or a fragment of the biomolecule (e.g., peptide or nucleic acid); size fractionation and determining the relative amount of biomolecule (e.g., peptide or nucleic acid) or a fragment of the biomolecule (e.g., peptide or nucleic acid); by direct or indirect quantitation of biomolecule (e.g., peptide or nucleic acid) fragmentation; or by the amount of phosphorylation or prenylation (e.g., peptide).

In particular embodiments, the elutable porous or semi-porous substrate comprises a hydrophilic biocompatible material, a synthetic or natural polymer, cellulose, polyester, or polyurethane. In other particular embodiments, the elutable porous or semi-porous substrate has a density in a range of ⅓-10 lbs/ft³. In an additional embodiment, the elutable porous or semi-porous substrate is elastomeric. Elastomeric substrates include materials that are compressible to ½, ⅕, 1/10, 1/25, 1/50, or 1/100 of the volume of the uncompressed state, and materials that are expandable up to 2-fold, 5-fold, 10-fold, 25-fold, 50-fold, or 100-fold the volume of the uncompressed state. In particular aspects, the elutable elastomeric porous or semi-porous substrate comprises open cell foam, a closed cell foam or a combination thereof. In other particular aspects, the elutable porous or semi-porous non-elastomeric substrate comprises FTA®, rag paper, or Isocode™.

In other embodiments, the substrate is such that applying a fluid to the substrate having a biomolecule (e.g., peptide or nucleic acid) absorbed thereto elutes or recovers at least a portion of the biomolecule from the substrate. In particular aspects, 30-50%, 50-65%, 65-80%, 80-90%, or more of the biomolecule (e.g., peptide or nucleic acid) is eluted or recovered from an elutable porous or semi-porous elastomeric substrate upon applying a fluid (e.g., an aqueous liquid such as water) to the substrate. In more particular aspects, the aqueous liquid has a pH within a range of 5.0 to 9.0, has a pH within a range of 10 to 12, 11 to 12, 11.3 to 11.8, 11.4 to 11.7, or a pH of about 11.4, 11.5, 11.6, 11.7, or 11.8, or has a stabilized pH. In further particular aspects, stabilization of pH can be achieved with a zwitterion, with Tris (hydroxymethyl) aminomethane hydrochloride (TRIS), N-(2-hydroxyethyl) piperazine-N'-2-ethanesulfonic acid (HEPES), 3-(N-morpholino) propanesulfonic acid (MOPS), 2-(N-morpholino) ethanesulfonic acid (MES), N-tris[hydroxymethyl]methyl-2-aminoethanesulfonic acid (TES), N-[carboxymethyl]-2-aminoethanesulfonic acid (ACES), N-[2-acetamido]-2-iminodiacetic acid (ADA), N,N-bis[2-hydroxyethyl]-2-aminoethanesulfonic acid (BES), N-[2-hydroxyethyl] piperazine-N'-[2-hydroxypropoanesulfonic acid] (HEPPSO), N-tris[hydroxymethyl]methylglycine (TRICINE), N,N-bis[2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino) ethanesulfonic acid (CHES), N-(2-hydroxyethyl)piperazine-N'-(3-propanesulfonic acid) (EPPS), piperazine-N,N'-bis(2-ethanesulfonic acid (PIPES), [(2-hydroxy-1,1-bis[hydroxymethyl]ethyl) amino]-1-propanesulfonic acid (TAPS), 2-amino-2-methyl-1-propanol (AMP), 3-[(1,1-dimethyl-2-hydroxyethyl) amino]-2-hydroxypropanesulfonic acid (AMPSO), ethanolamine, or 3-amino-1-propanesulfonic acid.

In further embodiments, the elutable porous or semi-porous elastomeric or non-elastomeric substrate substrate has or has not been treated with an additive or other treatment, or has or is substantially free of a particular substance, component or constituent. In one aspect, the elutable porous or semi-porous elastomeric or non-elastomeric substrate substrate has not been treated with a or is substantially free of a polyhydric compound (e.g., has an amount of polyhydric compound less than about 0.25% of total mass (w/w)). In another aspect, the elutable porous or semi-porous elastomeric or non-elastomeric substrate substrate is substantially free of glass or glass fibers. In still further aspects, the elutable porous or semi-porous elastomeric or non-elastomeric substrate has been treated with a buffer (e.g., a pH stabilizing agent), a chelating agent, a denaturing agent, a detergent, a reducing agent, an anti-oxidant, a protease inhibitor, a nuclease inhibitor, an anti-microbial, or a low water uptake saccharide.

In more particular aspects, the pH stabilizing agent maintains pH from pH 5.0 to pH 9.0, and is optionally selected from potassium chloride, citric acid, potassium hydrogenphthalate, boric acid, potassium dihydrogenphosphate, Diethanolamine, sodium citrate, sodium dihydrogenphosphate, sodium acetate, sodium carbonate, sodium tetraborate, cacodylic acid, imidazole, and 2-Amino-2-methyl-1-propanediol. In more particular aspects, the chelating agent is optionally selected from EDTA (Ethylenediamine-tetraacetic acid), EGTA (Ethyleneglycol-O,O'-bis(2-aminoethyl)-N,N,N',N'-tetraacetic acid), GEDTA (Glycoletherdiaminetetraacetic acid), HEDTA (N-(2-Hydroxyethyl)ethylenediamine-N,N',N'-triacetic acid), NTA (Nitrilotriacetic acid), Salicylic acid and Triethanolamine. In more particular aspects, the denaturing agent or detergent is an anionic surfactant, nonionic surfactant, cationic surfactant or ampholytic surfactant, which is optionally selected from SDS, Sodium lauryl sulfate, NP40, triton X-100, Sodium cholate, Sodium deoxycholate, Benzethonium chloride, CTAB (Cetyltrimethylammonium bromide), Hexadecyltrimethylammonium bromide and N,N-Dimethyldecylamine-N-oxide. In more particular aspects, the reducing agent or antioxidant is a free radical scavenging agent, or is optionally selected from DTT (dithiothreitol), dithioerythritol, urea, uric acid, mercaptoethanol, dysteine, vitamin E, vitamin C, dithionite, thioglycolic acid and pyrosulfite. In more particular aspects, the protease inhibitor is a serine or cysteine protease inhibitor, and is optionally selected from PMSF, PMSF Plus, APMSF, anti-thrombin III, Amastatin, Antipain, aprotinin, Bestatin, Benzamidine, Chymostatin, calpain inhibitor I and II, E-64, 3,4-dichloroisocoumarin, DFP, Elastatinal, Leupeptin, Pepstatin, 1, 10-Phenanthroline, Phosphoramidon, TIMP-2, TLCK, TPCK, trypsin inhibitor (soybean or chicken egg white), hirustasin, alpha-2-macroglobulin, 4-(2-aminoethyl)-benzenesulfonyl fluoride hydrochloride (AEBSF) and a Kunitz-type protease inhibitor. In more particular aspects, the anti-microbial is an anti-biotic, anti-viral, anti-fungal or anti-parasitic agent; is a member of a class selected from: beta-lactams; semisynthetic penicillins; monobactams; carboxypenems; aminoglycosides; glycopeptides; glucan synthesis inhibitors; Lincomycins; macrolides; polypeptides; allylamines; azoles; polyenes; sulfonamides; pyrimidines; tetraenes; thiocarbamates; benzoic acid compounds, complexes and derivatives thereof; rifamycins, tetracyclines, reverse transcriptase inhibitors, protease inhibitors, thymidine kinase inhibitors, sugar or glycoprotein synthesis inhibitors, structural protein synthesis inhibitors, nucleoside analogues, and viral maturation inhibitors, or is optionally selected from: penicillin, cephalosporin, ampicillin, amoxycillin, aztreonam, clavulanic acid, imipenem, streptomycin, gentamycin, vancomycin, clindamycin, polymyxin, erythromycin, bacitracin, amphotericin, nystatin, rifampicin, tetracycline, chlortetracycline, doxycycline, chloramphenicol, ammolfine, butenafine, naftifine, terbinafine, ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, undecylenate, silver sulfadiazine, undecylenic acid, undecylenic alkanolamide, Carbol-Fuchsin, nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir and ganciclovir.

In yet another aspect, the elutable porous or semi-porous substrate has been treated with a low-water uptake saccharide (L- or D-form), such as a non-reducing sugar (e.g., trehalose, a trehalose analogue, such as 6-azido-6-deoxytrehalose, or a trehalose derivative, such as trehalose-6-phosphate), or a malodextrin, such as a mono-saccharide (e.g., fucose) or a di-saccharide. In more particular aspects, the low-water uptake saccharide has a glass transition temperature greater than 60° C., greater than 65° C., greater than 70° C., or greater than 75° C.; or has a hydroscopicity less than 15% (% weight gain at 25° C. at 94% estimated relative humidity), less than 10%, less than 5%, or less than 1%. In additional more particular aspects, the absorbed biomolecule (e.g., peptide or nucleic acid) and low-water uptake saccharide are in a molar or mass ratio of about 1:0.5 to about 1:10.

In yet additional embodiments, the compositions of the invention, including kits, further include or exclude a substance, component or constituent. In one aspect, compositions of the invention include an aqueous liquid (e.g., water or an alkaline solution) for elution or recovery of at least a portion of the absorbed biomolecule (e.g., peptide or nucleic acid) from the elutable substrate. In more particular aspects, the aqueous liquid for elution or recovery of at least a portion of the absorbed peptide has a pH within a range of 5.0 to 9.0, within a range of pH 10 to 12, pH 11 to 12, pH 11.3 to 11.8, pH 11.4 to 11.7, a pH of about 11.4, 11.5, 11.6, 11.7, or 11.8, or has a stabilized pH.

Biomolecules absorbed to substrate include peptides or nucleic acids. Biomolecules absorbed to substrate further include biological samples, such as whole blood, serum, plasma, biopsied cells or tissue, sputum, mucus, cerebrospinal fluid, hair, urine, stool, and semen; as well as cells, bacteria, virus, yeast, and mycoplasma, optionally isolated or purified. Biological samples absorbed to substrate can be obtained from or produced by a subject, such as a mammal (e.g., a human). Particular subjects from which samples can be obtained from or produced by include a subject screened for a genetic disease or physiological disorder, or a predisposition towards a genetic disease or physiological disorder; a subject that has or is at risk of having a disease or physiological disorder, such as a genetic disorder, a hyperproliferative disorder, an immunological disorder or a microbial infection; or a subject is incarcerated, has been incarcerated or is at risk of incarceration.

In accordance with the invention, also provided are kits, including a composition set forth herein. In one embodiment, a kit includes a device for elution or recovery of at least a portion of an absorbed biomolecule (e.g., peptide or nucleic acid) from the substrate. In one aspect, the device has a physical size sufficient for introducing or holding the substrate, an open end, an openable end or a removable end, and physical dimensions suitable for inserting a plunger into the device so the plunger can cause compression of the substrate. In a more particular aspect, the device is substantially as shown on FIG. 2 or FIG. 3, or is a spin column. In another embodiment, a kit includes instructions for elution or recovery of at least a portion of an absorbed biomolecule (e.g., peptide or nucleic acid) from the substrate. In various aspects, the absorbed biomolecule is subjected to preferential or selective elution or recovery from the substrate, or where multiple biomolecules are desired to be eluted or recovered from substrate, subjected to simultaneous elution or recovery from the substrate.

In accordance with the invention, further provided are storage units. In one embodiment, a storage unit has a plurality of compartments, each compartment having a physical size sufficient for holding individual elutable porous or semi-porous elastomeric or non-elastomeric substrates, and an elutable porous or semi-porous elastomeric or non-elastomeric substrate, wherein the substrate is suitable for absorbing a biomolecule (e.g., peptide or nucleic acid) and for elution or recovery of the absorbed biomolecule (e.g., peptide or nucleic acid); and, instructions for absorbing a biomolecule (e.g., peptide or nucleic acid) to the substrate. In another embodiment, a storage unit includes instructions for eluting or recovering an absorbed biomolecule (e.g., peptide or nucleic acid) from the elutable porous or semi-porous elastomeric substrate; or instructions for preparing an aqueous liquid for eluting or recovering an absorbed biomolecule (e.g., peptide or nucleic acid) from the elutable porous or semi-porous elastomeric substrate. In still another embodiment, a storage unit includes an aqueous liquid for eluting or recovering an absorbed biomolecule (e.g., peptide or nucleic acid) from the elutable porous or semi-porous elastomeric substrate. In particular aspects, a storage unit is a multi-well plate, such as a plate having 2-6, 6-12, 12 to 24, 24-96, or more wells, or a plate in which one or more of wells of the multi-well plate has a volume of about 10-50 ul, 50-100 ul, 100-250 ul, 250-500 ul, 0.5-1.0 ml, 1.0-2.0 ml, 2.0-3.0 ml, 3.0-5.0 ml, or 5.0-10.0 ml.

Storage units can include a plurality of compositions. In one embodiment, a storage unit has a plurality of compartments, the compartments each having a physical size sufficient for holding individual elutable porous or semi-porous elastomeric or non-elastomeric substrates, wherein the substrate is suitable for absorbing a biomolecule (e.g., peptide or nucleic acid) and for elution or recovery of the absorbed biomolecule (e.g., peptide or nucleic acid); and, wherein a biomolecule (e.g., peptide or nucleic acid) is absorbed to one or more of the substrates contained therein. In one aspect, a storage unit includes at least two substrates each having a different absorbed biomolecule (e.g., peptide or nucleic acid), such as a different absorbed biological sample.

In accordance with the invention, provided are storage apparatus', including an absorbed or unabsorbed porous or semi-porous elastomeric or non-elastomeric substrate. In one embodiment, a storage apparatus is capable of maintaining a temperature at about −20° C., at 4° C., at 4-10° C., at 10-20° C., at 20-30° C., at 30-40° C., at 40-50° C., at 50-60° C., at 60-70° C., or at 70-80° C.

In accordance with the invention, additionally provided are libraries. In one embodiment, a library includes at least two elutable porous or semi-porous elastomeric or non-elastomeric substrates (a plurality) each of which have a different biomolecule (e.g., peptide or nucleic acid), such as a different absorbed biological sample, absorbed to the substrate. In various particular aspects, the library includes 10-50, 50-100, 100-500, 500-2500, 2500-10,000, 10,000-50,000, 50,000-250,000 different biomolecules (e.g., peptides or nucleic acids), such as a different absorbed biological sample, each of which is absorbed to an elutable porous or semi-porous elastomeric substrate.

In accordance with the invention, yet also provided are methods of producing a stabilized or preserved biomolecule (e.g., peptide or nucleic acid) in an elutable or recoverable form. In one embodiment, a method includes providing an elutable porous or semi-porous elastomeric or non-elastomeric substrate, wherein the substrate allows elution of a biomolecule (e.g., peptide or nucleic acid) absorbed thereto; contacting the substrate with a biomolecule (e.g., peptide or nucleic acid) under conditions allowing absorption of the biomolecule (e.g., peptide or nucleic acid) to the substrate; and reducing, if necessary, moisture from the contacted substrate to less than about 5%, 5-10%, 10-15%, 15-20%, or 20-25% by mass, thereby producing a stabilized or preserved biomolecule (e.g., peptide or nucleic acid) in an elutable or recoverable form. In another embodiment, a method includes providing an elutable porous or semi-porous substrate that has been treated with a low-water uptake saccharide, but not treated with an alcohol, glycerol, sucrose, carrageenan, xanthum gum or pectin; contacting the substrate under conditions allowing absorption of a biomolecule (e.g., peptide or nucleic acid) to the substrate; and reducing, if necessary, moisture from the contacted substrate to less than about 5%, 5-10%, 10-15%, 15-20%, or 20-25% by mass, thereby producing a stabilized or preserved biomolecule (e.g., peptide or nucleic acid) in an elutable or recoverable form. In one aspect, the biomolecule is a peptide. In another aspect, the biomolecule is a nucleic acid. In an additional aspect, the biomolecule is a peptide and a nucleic acid, wherein absorption of the peptide to the substrate occurs prior to, simultaneously with or following absorption of the nucleic acid to the substrate. In a further aspect, the biomolecule is a biological sample, such as whole blood, serum, plasma, biopsied cells or tissue, sputum, mucus, cerebrospinal fluid, urine, stool, or semen; cells, bacteria, virus, yeast, or mycoplasma; or from a subject, such as a mammal (e.g., a human), optionally isolated or purified.

In accordance with the invention, yet further provided are methods of storing a biomolecule (e.g., peptide or nucleic acid) in an elutable or recoverable form. In one embodiment, a method includes providing an elutable porous or semi-porous elastomeric or non-elastomeric substrate, wherein the substrate allows elution of a biomolecule (e.g., peptide or nucleic acid) absorbed thereto; contacting the substrate with a biomolecule (e.g., peptide or nucleic acid) under conditions allowing absorption of the biomolecule (e.g., peptide or nucleic acid) to the substrate; and reducing, if necessary, moisture from the contacted substrate to less than about 5%, 5-10%, 10-15%, 15-20%, or 20-25% by mass, thereby producing a stored biomolecule (e.g., peptide or nucleic acid) in an elutable or recoverable form. In another embodiment, a method includes providing an elutable porous or semi-porous substrate that has been treated with a low-water uptake saccharide, but not treated with an alcohol, glycerol, sucrose, carrageenan, xanthum gum or pectin; contacting the substrate under conditions allowing absorption of a biomolecule (e.g., peptide or nucleic acid) to the substrate; and reducing, if necessary, moisture from the contacted substrate to less than about 5%, 5-10%, 10-15%, 15-20%, or 20-25% by mass, thereby producing a stored biomolecule (e.g., peptide or nucleic acid) in an elutable or recoverable form. In one aspect, the biomolecule is a peptide. In another aspect, the biomolecule is a nucleic acid. In an additional aspect, the biomolecule is a peptide and a nucleic acid, wherein contacting of the peptide to the substrate occurs prior to, simultaneously with or following contacting of the nucleic acid to the substrate. In a further aspect, the biomolecule is a biological sample, such as whole blood, serum, plasma, biopsied cells or tissue, sputum, mucus, cerebrospinal fluid, urine, stool, or semen; cells, bacteria, virus, yeast, or mycoplasma; or from a subject, such as a mammal (e.g., a human), optionally isolated or purified.

In accordance with the invention, yet additionally provided are methods of eluting a biomolecule (e.g., peptide or nucleic acid) absorbed to an elutable porous or semi-porous elastomeric or non-elastomeric substrate. In one embodiment, a method includes providing a biomolecule (e.g., peptide or nucleic acid) adsorbed to an elutable porous or semi-porous elastomeric or non-elastomeric substrate, said substrate substantially free of moisture; hydrating the substrate with a liquid under conditions that elute at least a portion of the absorbed biomolecule (e.g., peptide or nucleic acid) from the substrate; and agitating, incubating or compressing said hydrated substrate to elute at least a portion of the absorbed biomolecule (e.g., peptide or nucleic acid) from the substrate, thereby eluting a biomolecule (e.g., peptide or nucleic acid) absorbed to an elutable porous or semi-porous elastomeric or non-elastomeric substrate. In one aspect, the biomolecule is a peptide. In another aspect, the biomolecule is a nucleic acid. In an additional aspect, the biomolecule is a peptide and a nucleic acid. In a further aspect, the biomolecule is a biological sample, such as whole blood, serum, plasma, biopsied cells or tissue, sputum, mucus, cerebrospinal fluid, urine, stool, or semen; cells, bacteria, virus, yeast, or mycoplasma; or from a subject, such as a mammal (e.g., a human), optionally isolated or purified.

In accordance with the invention, moreover provided are methods of recovering a biomolecule (e.g., peptide or nucleic acid) absorbed to an elutable porous or semi-porous elastomeric or non-elastomeric substrate. In one embodiment, a method includes providing a biomolecule (e.g., peptide or nucleic acid) absorbed to an elutable porous or semi-porous elastomeric or non-elastomeric substrate, the substrate substantially free of moisture; hydrating the substrate with a liquid under conditions that elute at least a portion of the absorbed biomolecule (e.g., peptide or nucleic acid) from the substrate; agitating, incubating or compressing said hydrated substrate to elute at least a portion of the absorbed biomolecule (e.g., peptide or nucleic acid) from the substrate; and collecting the eluate, thereby recovering a biomolecule (e.g., peptide or nucleic acid) absorbed to an elutable porous or semi-porous elastomeric or non-elastomeric substrate. In one aspect, the biomolecule is a peptide. In another aspect, the biomolecule is a nucleic acid. In an additional aspect, the biomolecule is a peptide and a nucleic acid. In a further aspect, the biomolecule is a biological sample, such as whole blood, serum, plasma, biopsied cells or tissue, sputum, mucus, cerebrospinal fluid, urine, stool, or semen; cells, bacteria, virus, yeast, or mycoplasma; or from a subject, such as a mammal (e.g., a human), optionally isolated or purified.

In accordance with the invention, yet also provided are methods of producing libraries having a plurality of stored biomolecules (e.g., peptide or nucleic acid). Each of the stored biomolecules (e.g., peptide or nucleic acid) can be absorbed to a different porous or semi-porous substrate.

In one embodiment, a method includes a) contacting an elutable porous or semi-porous substrate with a first biological sample under conditions allowing absorption of the first biological sample to the substrate; b) reducing, if necessary, moisture from the contacted substrate to less than about 5%, 5-10%, 10-15%, 15-20%, or 20-25% by mass, thereby producing a stored first biological sample; and repeating steps a) and b) at least one time with a second or subsequent biological sample absorbed to a different elutable porous or semi-porous substrate, thereby producing a library comprising a plurality of stored biological samples. In one aspect, either the first or second absorbed biological sample is recoverable from the elutable elastomeric substrate. In another aspect, either the first or second absorbed biological sample resists degradation following absorption to the substrate, as compared to the first or second biological sample not absorbed to the substrate. In a further aspect, the elutable porous or semi-porous substrate is elastomeric. In additional aspects, the first or second absorbed biological sample includes a peptide or nucleic acid, which peptide or nucleic acid optionally is isolated or purified.

In accordance with the invention, provided are specific iterations of various embodiments. In one iteration, a biological sample is absorbed to an elutable porous or semi-porous elastomeric substrate, the substrate substantially free of moisture, wherein at least a portion of the absorbed biological sample is recoverable from the substrate. In another iteration, a biological sample is absorbed to an substrate, the substrate consisting of an elutable porous or semi-porous substrate substantially free of moisture, wherein at least a portion of the absorbed biological sample is recoverable from the substrate. In an additional iteration, a peptide or nucleic acid alone, or in combination, is absorbed to a substrate, the substrate consisting of an elutable elastomeric porous or semi-porous substrate substantially free of moisture, wherein at least a portion of the absorbed peptide or the absorbed nucleic acid alone, or in combination, is recoverable from the elutable porous or semi-porous elastomeric substrate. In a further iteration, a biological sample is absorbed to a substrate, the substrate consisting of an elutable porous or semi-porous substrate substantially free of moisture, wherein at least a portion of the absorbed biological sample is recoverable from said substrate.

Additional specific iterations of various embodiments include storage units, in which in one iteration, the unit houses a plurality of stored or preserved peptides alone, or in combination with one or more nucleic acids, each peptide alone, or in combination with nucleic acid is individually absorbed to an elutable porous or semi-porous elastomeric substrate substantially free of moisture, wherein at least a portion of said absorbed peptide alone, or in combination with nucleic acid is recoverable from said elutable porous or semi-porous elastomeric substrate. In a particular iteration, each of the plurality of stored or preserved peptides or nucleic acids absorbed to the substrate has a defined location or address within the storage unit. In another particular iteration, the absorbed peptide or nucleic acid is a biological sample.

Further specific iterations of various embodiments include libraries, in which in one embodiment, includes a plurality of different stored or preserved peptides or nucleic acids each peptide or nucleic acid absorbed to an elutable porous or semi-porous elastomeric or non-elastomeric substrate, the substrate substantially free of moisture, wherein at least a portion of the absorbed peptide or the absorbed nucleic acid is recoverable from the elutable porous or semi-porous elastomeric or non-elastomeric substrate. In a particular iteration, each of the plurality of peptides or nucleic acids absorbed to the substrate has a defined location or address in the library In another particular iteration, the absorbed peptide or nucleic acid is a biological sample.

DESCRIPTION OF DRAWINGS

FIG. 2 is a schematic diagram of sample (e.g., serum or plasma) absorption to a substrate (sponge) housed in a vessel (storage unit, vial), and capping the vessel for storage. A plurality of vessels can be arrayed in a 96 SBS format plate frame, or other suitable format, for manual or automated retrieval and elution or recovery of one or more absorbed samples.

FIG. 6 is a graphical illustration of the quantity of various serum analytes stored on sponge (TE) at room temperature after seven days, vs. fresh and frozen serum (see the data presented in Tables 5-7).

FIG. 13 is a graphical illustration of the quantity of various serum analytes of various serum analytes in fresh vs. frozen serum (55 days).

FIG. 21 is a graphical illustration of the quantity of various serum analytes stored on sponge (TE+Cysteine+NP40) at room temperature after 55 days, vs. fresh and frozen serum (see the data presented in Tables 5-7).

FIG. 23 is a graphical illustration of the quantity of various serum analytes stored on sponge (no treatment) at room temperature after 187 days, vs. fresh and frozen serum (see the data presented in Tables 5-7).

FIG. 38 is a gel electrophoresis result of the total recovered DNA eluted from a polyester sponge used to absorb blood and stored for 167 days.

DETAILED DESCRIPTION

Figure 1:
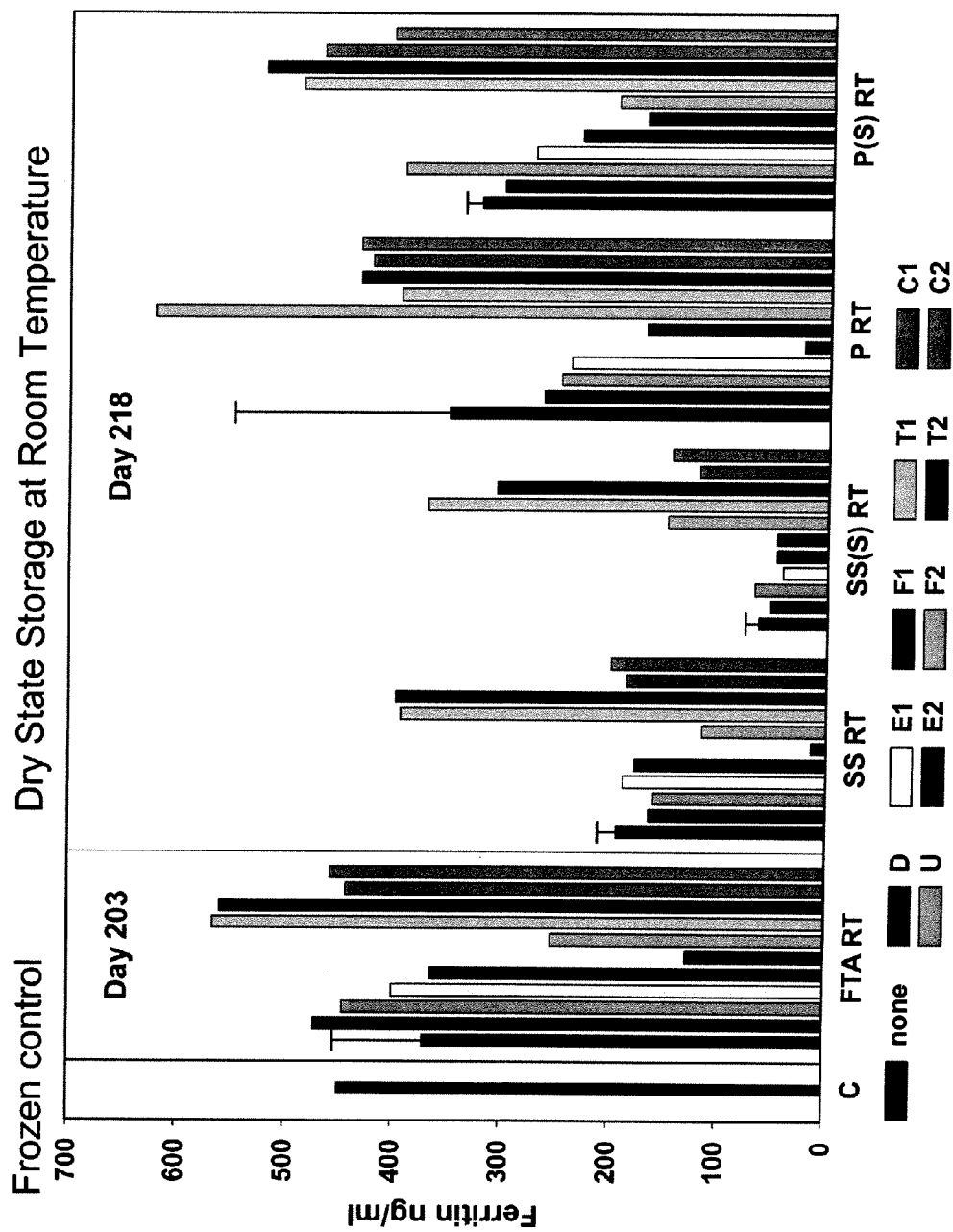
FIG. 1 is a bar graph illustration of protein storage with and without trehalose and other treatments on various substrates. Abbreviations: T is trehalose; SS is S&S 903™; F is FTA®; (S) is the "SG" cocktail (160 mM Tris, 10 mM EDTA, 2% NP40). Other symbols refer to additional treatments in the table: E=vitamin E, C=cysteine, F=fucose.

The invention provides compositions and methods for storage of biomolecules. Biomolecules are stored via absorption of a fluid containing at least one biomolecule to a porous or semi-porous substrate. The substrate to which a biomolecule is absorbed is dried so as to be substantially free of moisture. The absorbed biomolecule can optionally be eluted or recovered from the substrate at a future time and subjected to a subsequent analysis or application. Biomolecules absorbed to substrate for storage are therefore recoverable, at least in part, from the substrate. Biomolecules absorbed to substrate for storage may also optionally be preserved, i.e., the absorbed biomolecule is resistant to or resists degradation. A preserved biomolecule is useful for a subsequent analysis or application. Biomolecules appropriate for absorption as a fluid to a substrate for storage, and for optional preservation include, inter alia, peptides, nucleic acids, carbohydrates, sugars, fatty acids, lipids. Biomolecules absorbed to a substrate may be a sample obtained from, produced by or derived from a living or non-living organism, such as a cell, organ or tissue sample, e.g., blood, serum or plasma. Accordingly, suitable biomolecules for absorption to a substrate for storage further include biological material and biological samples.

The invention therefore provides, in one embodiment, a composition including a biomolecule (e.g., peptide or nucleic acid) and an elutable porous or semi-porous substrate, wherein the composition is substantially free of moisture and the biomolecule (e.g., peptide or nucleic acid) is absorbed to the porous or semi-porous substrate, wherein the absorbed biomolecule (e.g., peptide or nucleic acid) optionally resists degradation as compared to unabsorbed biomolecule, and wherein at least a portion of the absorbed biomolecule is recoverable from said porous or semi-porous substrate. The invention also provides, in another embodiment, a composition including at least two biomolecules (e.g., a peptide and a nucleic acid) and an elutable porous or semi-porous substrate, wherein the composition is substantially free of moisture and the biomolecules (e.g., peptide and a nucleic acid) are absorbed to the substrate, wherein one or more of the absorbed biomolecules (e.g., peptide or nucleic acid) optionally resists degradation as compared to one or more unabsorbed biomolecules (e.g., peptide or nucleic acid), and wherein at least a portion of one of the one or more absorbed biomolecules (e.g., peptide or nucleic acid) is elutable or recoverable from said substrate. In these and other embodiments, in particular aspects the porous or semi-porous substrate is elastomeric.

The invention further provides, in various embodiments, kits, storage units, storage apparatus, libraries and housings, including a biomolecule (e.g., peptide or nucleic acid) and an elutable porous or semi-porous substrate. In various aspects, a kit, storage unit, storage apparatus, library or housing includes a peptide and an elutable porous or semi-porous substrate, in which the peptide is absorbed to the porous or semi-porous substrate, the absorbed peptide optionally resists degradation as compared to unabsorbed peptide, and at least a portion of the absorbed peptide is elutable or recoverable from the porous or semi-porous substrate; or includes a peptide, a nucleic acid and an elutable porous or semi-porous substrate, in which the peptide and the nucleic acid are absorbed to the substrate, wherein the absorbed peptide or the absorbed nucleic acid optionally resists degradation as compared to unabsorbed peptide or unabsorbed nucleic acid, and wherein at least a portion of the absorbed peptide or the absorbed nucleic acid is recoverable or elutable from the substrate. In these and other embodiments, in particular aspects the porous or semi-porous substrate is elastomeric.

The invention additionally provides, in various embodiments, methods of producing stored, stabilized or preserved biomolecule (e.g., peptide or nucleic acid) in an elutable or recoverable form. The invention moreover provides, in various embodiments, methods of eluting or recovering a biomolecule (e.g., peptide or nucleic acid) absorbed to an elutable porous or semi-porous substrate. In these and other embodiments, in particular aspects the porous or semi-porous substrate is elastomeric.

As used herein, the term "substrate" refers to a single or multi-dimensional, natural or synthetic material or substance capable of absorbing a biomolecule (e.g., peptide or nucleic acid) containing fluid. Subsequent to, or simultaneously with absorption of biomolecule fluid to substrate, the biomolecule optionally can directly or indirectly be adsorbed to the substrate. Thus, a substrate is a material or substance that can absorb fluid containing a biomolecule, which material or substance also optionally can, but is not required, adsorb the biomolecule in the fluid. Exemplary non-limiting terms that are synonyms of substrate, when used in the appropriate context, include "medium" and "support."

As used herein, the term "elutable," when used in reference to a "substrate" or an equivalent term for substrate (e.g., medium or support), means that substantially all or a portion of a biomolecule (e.g., peptide or nucleic acid) absorbed to a substrate can be eluted, removed, unbound, detached from, or otherwise separated from the substrate under appropriate conditions. An elutable substrate allows a biomolecule (e.g., peptide or nucleic acid) absorbed to the substrate to be removed and optionally recovered from substrate in part or substantially completely. Elutable, when used in reference substrate to which a biomolecule is "absorbed," therefore means that absorption of the biomolecule to the substrate is reversible, at least in part. Elution of a biomolecule from absorbed to an elutable substrate does not typically require that covalent bonds be broken between the substrate and biomolecule. An elutable substrate can be elutable with respect to one or more absorbed biomolecules, but need not be elutable with respect to all biomolecules that may be present in a sample.

The term "absorbed," and grammatical variations therefore (e.g., absorbtive, absorption, absorbing, etc.) refers to a biomolecule (e.g., peptide or nucleic acid) in contact with a substrate, wherein the biomolecule is or was present (dissolved or suspended) in a fluid in contact with the substrate. In the case of a porous or semi-porous substrate, a fluid (e.g., liquid) containing one or more biomolecules is drawn into the interstitial space of the pores present in the substrate. For example, a porous or semiporous substrate may be wetted with a liquid sample having one or more biomolecules (e.g., a peptide or a nucleic acid dissolved or suspended therein) so that the liquid penetrates into the substrate pores. After drying (if appropriate), the biomolecules remain inside the pores of the substrate without any necessary requirement for non-ionic, ionic or covalent binding between the biomolecule and the substrate. Thus, a biomolecule "absorbed" to a substrate does not require adsorptive binding between the biomolecule and the substrate: mere occupancy of the porous space within the substrate is sufficient for a biomolecule to be absorbed to the substrate.

More particularly, where a substrate has pores (e.g., porous or semi-porous substrate), the interstitial space can capture biomolecules by absorption. For example, a porous or semi-porous elastomeric substrate such as a sponge or foam can capture biomolecules in the interstitial spaces of the pores. The sponge pores essentially behave as a vessel when biomolecules become trapped inside the interstitial space by absorption. One method for introducing biomolecules into interstitial spaces is to formulate the biomolecules into a liquid which can be drawn into the substrate pores by wetting (e.g., water-surface interaction) or by suction (compression then release) of the sponge. After fluid-filling of the sponge, any moisture present can be substantially removed, for example, via evaporation of water from the liquid, thereby leaving biomolecule (e.g., peptide or nucleic acid) and other solutes as a "residue" which remains within the pores, but without the requirement for adsorptive binding to the pore surface. As a result, biomolecules absorbed to a porous or semi-porous substrate occupy the interstices of the substrate pores, without the need for any adsorptive binding.

The term "absorbed" can also be used herein to refer to a type of material or substance that is suitable as an elutable substrate as set forth herein. Thus, an elutable substrate capable of or suitable for "absorbing" a biomolecule (e.g., peptide or nucleic acid) is a porous or semiporous material that can take up a fluid such that a biomolecule suspended or dissolved in the fluid can remain within the porous space for the purpose of storing and optionally preserving the biomolecule. An "absorbed substrate" therefore refers to a substrate to which a biomolecule has been absorbed. Elutable porous or semiporous substrates capable of or suitable for absorbing a biomolecule allow the biomolecule to be eluted or recovered, at least in part, from the substrate, for example, at a future date. To elute or recover absorbed biomolecule, absorption can be reversed, i.e., the absorbed substrate can be hydrated (typically via addition of an aqueous liquid) followed by elution or recovery of the biomolecule from the substrate.

As used herein, the term "adsorbed," and grammatical variations thereof, when used to refer to a relationship between a substance, such as a biomolecule (e.g., peptide or nucleic acid) and a substrate, means that the substance binds to the substrate. There are three basic modes of adsorptive binding of biomolecules to substrates: physical non-ionic binding, ionic binding and covalent binding. Physical non-ionic binding is where the surface of the substrate has physical properties (hydrophobic areas, for example) that bind to the biomolecule via van der Walls forces, hydrogen bonds or other strong non-ionic or non-covalent interactions. The degree of non-ionic binding is a function of the physical properties of the biomolecule and the substrate. Ionic binding is where a biomolecule has a charge that interacts with an opposite charge on the surface of the substrate. The charge of the biomolecule will be influenced by the pH and salt content of the fluid, if present. Ionic binding is therefore influenced by pH and salt concentration. Ionic binding is a medium strength bond, stronger than physical non-ionic binding but weaker than covalent bonding. Covalent binding is a binding reaction in which a chemical reaction forms a covalent bond between the biomolecule and substrate. Any of these three may be involved in mediating adsorption of a biomolecule to surface of a substrate.

Adsorptive binding between a biomolecule and a substrate may therefore consist of specific binding, such as the binding that occurs between a ligand and its receptor or an antibody and its antigen; or consist of non-specific binding, wherein the interaction between the biomolecule and substrate is not specific to a particular class or type of biomolecule. Adsorptive binding includes binding that is direct, such as through direct covalent or non-covalent (non-ionic or ionic) binding between a biomolecule (e.g., peptide or nucleic acid) and the substrate, or indirect binding, wherein adsorption is mediated by biomolecule binding to an intermediate molecule that in turn engages the substrate surface through adsorptive binding. A substrate capable of biomolecule adsorption can therefore be a material having an intrinsic or innate affinity, or a material which has been provided or endowed with an adhesion, attachment or an ability to specifically or non-specifically adsorptively bind to a particular type of biomolecule, but need not bind to all biomolecules. A specific example of adsorptive binding is DNA bound to an elutable elastomeric substrate, such as polyester, as set forth herein.

A biomolecule absorbed to a substrate may therefore also be adsorbed to a substrate. However, adsorption of a biomolecule to a substrate is not required in order to absorb the biomolecule to the substrate, or to store the biomolecule in a recoverable or elutable form. Thus, the term "absorbed" as used herein does not exclude adsorption of the biomolecule to the substrate, nor does the term "absorbed" as used herein require adsorption of the biomolecule to the substrate. It is understood that, in certain embodiments, a biomolecule absorbed to a substrate may also be weakly or strongly adsorbed to the substrate through adsorptive binding.

Typical materials suitable as substrates that absorb biomolecules (e.g., peptide or nucleic acid) and allow the absorbed biomolecules to be at least partially eluted or recovered from substrate include hydrophilic biocompatible materials. As used herein, a "biocompatible material" is a material that is compatible with storage and recovery of biomolecules. Such materials have the ability to be wet by contact with a liquid and are typically water insoluble. Additionally, such materials typically do not present highly charged surfaces or surfaces that react to form covalent bonds with biomolecules, so that absorbed biomolecules may be eluted with adequate efficiency.

Materials to which protein or nucleic acid bind in a nearly irreversible fashion due to strong non-ionic, ionic or covalent bonds (i.e., adsorptive binding), include materials with highly charged surfaces or hydrophobic surfaces, are less desirable because peptide or nucleic acid absorbed to such materials generally are difficult to elute or recover. Specific examples of less desirable substrates due to poor elution or recovery, which therefore can be excluded, are ceramics (e.g., carbon-nitrides, silicon-carbides, etc.), glass, glass fiber, nylon, polyvinyl chloride, polybutylene, polypropylene, polyethylene, polycarbonate or other materials that may directly or indirectly, specifically or non-specifically, bind tightly to peptide or nucleic acid. Additional examples of less desirable materials are water soluble materials.

Specific non-limiting examples of materials useful as porous or semiporous substrates include cellulose (natural or cellulosic or synthetic polymer having various chain lengths), polyester, polystyrene, polyurethane (urethane) and cross-linked polyvinyl alcohol (PVA). Additional non-limiting examples of substrates include rag paper, FTA® (a modified cellulose material, Whatman, Inc., Fordham Park, N.J.), 903™ paper (Whatman, Inc., Fordham Park, N.J.), Iso-Code™ (Whatman, Inc., Fordham Park, N.J.) and Generation Capture Cards™ (Gentra Systems, Minneapolis, Minn.).

Modified, derivatized, functionalized, cross-linked and conjugated substrates are also included within the meaning of substrate, provided that the susbtrate so modified, derivatized, functionalized, cross-linked or conjugated is useful for its intended purpose. For example, a modified, derivatized, or functionalized substrate should not be so altered such that the substrate binds so tightly to a biomolecule desired to be eluted that the elution or recovery of the biomolecule from the altered susbtrate is difficult if not impossible. An additional example, for an elastomeric substrate, is that the substrate may be cross-linked provided that the cross-linking is not so extensive to render the material non-elastomeric. Another example are modifications that reduce pore size so as to substantially inhibit absorption of a desired biomolecule. Yet an additional example is where treatment of the substrate results in a surface that inhbits absorption of a desired biomolecule, for example, a substrate that is made oleophobic or hydrophobic, where it is desired to absorb a biomolecule present in an aqueous liquid. Of course, such a substrate is likely to be suitable for absorption of a biomolecule present in an oil or emulsion.

Derivatized and functionalized cellulose substrates include modification of one or more hydroxyl groups of the cellulose polymer. Particular non-limiting examples include polyethyleneimine-cellulose, cellulose with one or more side groups including 3,5 dimethylphenyl carbamate; 4-methylbenzoate; cinnimate; 4-methylphenyl carbamate; 4-chlorphenyl carbamate; phenyl carbamate; and benzoate. PVA derivatives include PVA-FEP. Conjugates of PVA include amino acid conjugates.

Functionalized substrates include modifications to the surface without altering the underlying structure of the substrate. For example, for an elastomeric substrate, the substrate surface can be functionalized without significantly reducing the elasticity of the substrate. Surfaces can be modified without altering the underlying physical or dimensional properties using a light-activated chemistry (see, for example, U.S. Patent Application Ser. No. 20050074478; SurModics, Inc., Eden Prarie, Minn.). Substrates with reactive groups including alcohols, acids, thiols, amines, amides, etc., can be derivatized or cross-linked.

As used herein, the terms "semipororus" and "porous," when used in reference to a "substrate" or an equivalent term for substrate (e.g., medium or support), means that the substrate has a permeable surface, interstitial space, interior cavities (pores) or channels that allow a fluid to penetrate or reside on or within the substrate surface. Such a substrate has the ability to sequester a fluid (e.g., a liquid having a biomolecule dissolved or suspended therein) within the porous interstitial space for the purpose of absorbing and storing a biomolecule (e.g., peptide or nucleic acid). A porous or semi-porous substrate also provides a greater effective surface area for adsorptive contact with a biomolecule than a non-porous substrate having the same or similar size. Thus, porous and semiporous substrates will typically have greater capacity for biomolecule (e.g., peptide or nucleic acid) adsorption than a comparably sized non-porous substrate. In addition, a three-dimensional porous or semiporous substrate will have a greater absorptive capacity than a two-dimensional substrate. To illustrate this difference in storage capacity, a 6 mm high×5 min wide three-dimensional elutable elastomeric porous substrate (sponge cylinder) can absorb a fluid volume of 150 ul. In contrast, a 6 mm non-elastomeric 2-dimensional paper disc can only absorb 10 ul of fluid. A particular example of a porous substrate is an open-cell sponge or foam.

Within a porous or semiporous substrate, interstitial spaces, cavities, pores or channels can be regularly or irregularly shaped, have different sizes, have uniform or nonuniform sizes, and have a regular, non-regular (random) or semi-regular distribution pattern in the substrate. Typically, pores are macroporous in size. Exemplary pores have an average size ranging from about 0.5 to 1000 microns ($\mu$m) or more, or any numerical value or range within such ranges. Typically, pores will have an average size range from about 10 to 100 microns ($\mu$m), more typically from 10 to 20 microns ($\mu$m), or any numerical value or range within such ranges. An exemplary pore size distribution has a mean 20 micron pore size with a standard deviation of +/−10 microns.

Porosity refers to the pore density, and can be expressed as the total volume occupied by pores per unit volume of substrate. Exemplary pore densities range between about 10 to 10,000 pores per linear centimeter (PPC), or any numerical value or range within such a range.

The term "semi-porous," when used in reference to a "substrate" or an equivalent term for substrate (e.g., medium or support), means that the substrate has more surface area available for biomolecule absorption in a given volume than a non-porous substrate of comparable physical size. A particular example of a semi-porous substrate is a combination of an open-cell and closed-cell sponge or foam.

Void volume is the volume of a porous or semiporous material that is not composed of the material itself, i.e., in a dried material it is the air or open space within the material. Void volume can be expressed as a percentage, the value representing the percent of the total volume of the material that is void. The void volume determines, at least in part, the absorptive capacity of the material. The term "porous," when used herein to refer to a substrate, means a substrate having a void volume of at least 25%, more typically greater than 25%, for example, 30%, 40%, 50%, 60%, 70%, 75%, 80%, 90%, or more, or any numerical value or range within such values. The term "semiporous," when used herein to refer to a substrate, means a substrate having a void volume of between 10-25%, or any numerical value or range within such a range.

Substrates may be rigid (e.g., non-elastomeric), semi-rigid, or malleable, conformable or deformable (e.g., elastomeric). Elastomeric substrates include deformable materials having elastic or sponge characteristics. Sponge characteristics include, for example, the ability to be stretched, compressed or expanded. Typically, an elastomeric substrate, after stretching, compressing or expanding, can return to the original or nearly the original size or shape of the substrate prior to stretching, compressing, expanding or other deformation.

One measure of the degree to which an elastomeric substrate can be deformed is referred to as compressibility or elongation. Compressibility and elongation values are typically expressed as a percentage of the physical size of the material in the compressed or expanded state relative to the physical size of the material in the uncompressed or unexpanded state. For example, a 50% compressibility means that the material can be compressed to half the physical size of the uncompressed or unexpanded state. A 200% elongation means that the material can be expanded to double the physical size of the uncompressed or unexpanded state. Typical non-limiting compressibility and elongation values for elastic, malleable, or deformable (e.g., elastomeric) substrates included in the invention range from 5-10% to 500-1000%, or any numerical value or range within such percent ranges. The skilled artisan can select appropriate elastomers and elastomeric materials for substrates having particular compressibility and elongation values.

Substrates generally, and elastomeric substrates in particular, can be any size, shape or dimension convenient for the intended biomolecule storage or preservation function. The size will be determined, in part, by the volume of biomolecule to be stored or preserved, and the desired format for storage or preservation, for example, a multi-well storage unit amendable to automation. The size will therefore be determined in part on the volume or quantity of sample to be absorbed to the substrate. In order to minimize the volume of elution or recovery liquid, typically substrate will have sufficient size to absorb the sample, but not be so large as to result in the undesirable dilution of the eluted or recovered biomolecule. Substrate size will therefore be determined at least in part by the amount of biomolecule to be absorbed and the concentration of the biomolecule desired in the elution or recovery liquid.

Substrate shape will be determined in part by any housing (e.g., vessel or tube) or storage unit containing the substrate. Exemplary sizes range from 0.01-1.0 $cm^2$, 1.0-5 $cm^2$, 5-10 $cm^2$ for two-dimensional substrates. For three-dimensional substrates, such as elastomeric substrates including sponges and foams, volumes will range from 1-5 $mm^3$, 5-10 $mm^3$, 10-20 $mm^3$, 20-30 $mm^3$, 30-50 $mm^3$, 50-100 $mm^3$, 100-200 $mm^3$, 200-500 $mm^3$, 500-1000 $mm^3$, 1-5 $cm^3$, 5-10 $cm^3$, 10-20 $cm^3$, 20-30 $cm^3$, 30-50 $cm^3$, 50-100 $cm^3$, 100-200 $cm^3$, 200-500 $cm^3$, or more, or any numerical value or range within such ranges. An exemplary elastomeric substrate is a 5 mm high×6 mm wide cylinder, which has a volume of about 150 $mm^3$. Exempary non-limiting substrate shapes include rectangular, square, cylindrical, circular, spherical and triangular.

Substrates can have various densities. For elutable porous or semi-porous substrates, typical densities will range from about ⅓ to 65 lbs/$ft^3$. For elastomeric substrates, typical densities will range from about ⅓-5 lbs/$ft^3$, more typically from about ½-1.5 lbs/$ft^3$.

Substrates include materials that inherently or have been modified to reduce, inhibit, delay or prevent degradation or loss of a biomolecule (e.g., peptide or nucleic acid). Thus, substrates can be used to store biomolecule such that the biomolecule is optionally also preserved. Appropriate substrates can be referred to as "storage substrates," or "storage media" since they are suitable for storing and optionally preserving a biomolecule (e.g., peptide or nucleic acid) for a subsequent application or analysis. The extent to which such a substrate preserves a biomolecule, i.e., reduces, inhibits, delays or prevents degradation or loss of the biomolecule (e.g., peptide or nucleic acid) is a function of the substrate material and any modifications or additives present on the absorbed substrate that affect degradation or loss of the absorbed biomolecule. The extent to which a substrate may function to preserve a biomolecule (e.g., peptide or nucleic acid) will also be a function of how labile the particular biomolecule absorbed to the substrate. For example, certain proteins are more labile than other proteins and, therefore, may degrade faster than less labile proteins, even when such proteins are preserved. Nevertheless, the substrates can at least partially protect or preserve such labile biomolecules from degradation, when absorbed, as compared to the same biomolecule that is not absorbed to the substrate.

Biomolecules can be preserved so as to maintain a native structure. However, preservation of a biomolecule does not require that the biomolecule retain the native secondary, tertiary or quateranary structure. Thus, a preserved peptide can be in its native form or be in a partially or completely denatured form. Of course, if a subsequent analysis requires or is not affected by degrading the stored biomolecule, the biomolecule secondary, tertiary or quateranary structure need not be maintained. For example, sequencing and proteomic studies, such as LC/MS and MALDI, the subject peptide is degraded with trypsin and as such, peptides used for such analysis need not be preserved in a folded state because the peptide will be subjected to denaturation and degradation for the analysis. For biomolecules in which it is desired to determine their presence in a stored sample using an antibody, for example, detection of a protein biomolecule, the protein can actually undergo degradation without preventing detecting by an appropriate antibody, particularly when the antibody was obtained for an unstructured peptide epitope.

Accordingly, the invention provides compositions in which a biomolecule (e.g., peptide or nucleic acid) is absorbed to a substrate. In particular aspects, degradation of the biomolecule is reduced, inhibited, delayed or prevented, i.e., the biomolecule is "resistant to" or "resists" degradation, or is "preserved," when it is absorbed to the substrate. In this aspect, preserved biomolecules absorbed to a substrate can subsequently be eluted or recovered from the substrate for a subsequent application or analysis, if desired. In alternative aspects, the biomolecule secondary, tertiary or quateranary structure need not be maintained, when absorbed to the substrate.

Biomolecule (e.g., peptide or nucleic acid) degradation can be detected or measured by a variety of qualitative and quantitative techniques. Exemplary techniques include, for example, determining the quantity of a peptide or a peptide fragment thereof or a nucleic acid or nucleic acid fragment thereof following elution and recovery from substrate as compared to an appropriate control, for example, an amount of peptide or nucleic acid frozen (e.g., at −20° C. or −70° C.) or fresh sample. Amounts of degraded peptide or nucleic acid can be determined using size fractionation (e.g., chromatography such as HPLC and FPLC, and gel fractionation by electrophoresis). Loss of peptide phosphorylation or prenylation can be used as a means to detect protein degradation. Immunoassays such as ELISA and RIA can be used to quantify or to detect specific proteins. Protein amounts in general can be determined using commercially available colorimetric or fluorimetric quantitative assays. Nucleic acid can also be calculated by UV spectroscopy or using commercially available colorimetric stains or intercalating agents (e.g., PicoGreen, Molecular Probes, Inc. Eugene Oreg.). Accordingly, the extent to which a biomolecule absorbed to substrate is preserved can be readily ascertained.

As a non-limiting example, a quantity of peptide (e.g., a biological sample such as blood) can be absorbed to substrate, subsequently eluted from the substrate after a period of time, and the peptide(s) recovered and quantified. The amount of recovered peptide is compared to an equivalent quantity of a freshly obtained or frozen sample of blood. Eluted or recovered peptide can also be qualitatively assessed, by fragmentation, for example, and the extent of fragmentation of recovered peptide compared to the extent of fragmentation of a same quantity of protein from a frozen (e.g., at −20° C. or −70° C.) or a freshly obtained sample (e.g., fresh blood). Peptide or nucleic acid fragmentation can be detected by a shift from higher molecular weight species to lower molecular weight species using various methods including column chromatography, gel electrophoresis, mass spectrometry and others known in the art. The resistance to degradation or amount of preservation can be expressed as the percentage of the amount of biomolecule (e.g., peptide or nucleic acid) present in a reference sample, such as an equivalent quantity of a stored or fresh sample, after adjustment for elution/recovery efficiency from substrate. Exemplary preservation percentages of biomolecules that resist degradation include, for example, a loss of no more than 50-75% of peptide or nucleic acid; 33-50% of peptide or nucleic acid; 25-33% of peptide or nucleic acid; 10-25% of peptide or nucleic acid; or 5-15% of peptide or nucleic acid, or any numerical value or range within such percent ranges. Exemplary preservation percentages of biomolecules that resist degradation include, for example, preserving 25-50% of peptide or nucleic acid; preserving 50-75% of peptide or nucleic acid; preserving 75-95% of peptide or nucleic acid; or preserving 90-95% of peptide or nucleic acid, or any numerical value or range within such percent ranges.

The biomolecules absorbed to the substrate can be preserved for any length of time, from short or long periods of time, including essentially indefinitely. Exemplary times include, for example, resistance to degradation for 5-10, 10-20, 20-30, 30-50, 50-90, 50-150, 150-365 days, weeks or months, or any numerical value or range within such ranges. Exemplary times further include, for example, resistance to degradation for 1, 2, 3, 4, 5, 6, 7, 8, 9, 10, 10-15, 15-20, 20-30 years, or more, or any numerical value or range within such ranges. As particular example, serum proteins absorbed to a polyester susbtrate are recoverable from substrate in an intact form after 6 months of room temperature storage.

The biomolecules absorbed to the substrate can be stored above, below or at ambient temperature. Exemplary storage temperatures include, for example, −70° C., −20° C., at about 4° C., at 4-10° C. at 10-20° C., at 20-30° C., at 30-40° C., at 40-50° C., at 50-60° C., at 60-70° C., at 70-80° C., or more, or any numerical value or range within such ranges.

The term "recoverable," and grammatical variations thereof, when used in reference to a substance such as a biomolecule (e.g., peptide or nucleic acid), and a substrate, means that at least a portion of the biomolecule absorbed to the substrate can be separated, removed, eluted, unbound or detached from the substrate under appropriate conditions in a form useful for or amenable to a subsequent analysis or application (e.g., sequencing, affinity or activity detection, mass spectrophotometry, amplification, cloning, etc., see, for example, Sambrook et al. (eds.), 1989, *Molecular Cloning: A Laboratory Manual*, Cold Spring Harbor Press, N.Y. and Ausubel et al. (eds.), 2000, *Current Protocols in Molecular Biology*, John Wiley & Sons, N.Y., which describes various applications directed towards peptide and nucleic acids). Typically, recovery occurs through hydration of the biomolecule-absorbed substrate. Exemplary hydrating conditions for recovering a peptide or a nucleic acid, separately from each other, sequentially, selectively, or in combination with each other, from substrate, are as set forth herein. Typical amounts of biomolecule recovered (the yield) range from 25% to 100% by mass, or any numerical value or range within such percent ranges. Recovery or yield of peptide or nucleic acid within the range of 30-35%, 35-40%, 40-45%, 45-50%, 50-60%, 60-65%, 65-70%, 70-75%, 75-80%, 80-85%, 85-90%, 90-95%, or more by mass, or any numerical value or range within such percent ranges, are also included. Typical recovery or yield of peptide from a substrate are 50% or more (e.g., 55%, 60%, 65, 70%, 75%, 80%, 85%, 90%, 95%, or more). For elution or recovery of nucleic acid from substrate with an alkaline liquid, typical yield is in the range of about 50% to about 100%, or more, for example, about 60% to about 90%, or about 70% to about 80%, of nucleic acid present in the sample absorbed to substrate. Percent recovery can refer to recovery of an individual peptide, a combination of peptides (i.e., a plurality of peptides), such as all protein absorbed to the substrate, or a subset of individual peptides (two or more) absorbed to the substrate. Percent recovery can also refer to recovery of an individual nucleic acid, a combination of nucleic acids (i.e., a plurality of nucleic acids), such as all nucleic acid absorbed to the substrate, or a subset of individual nucleic acids (two or more) absorbed to the substrate.

Partial recovery, when used in reference to biomolecule (e.g., peptide or nucleic acid) recovery and grammatical variations thereof, means that 25-50% or more, up to 75% of the total amount of a biomolecule (e.g., peptide or nucleic acid), or any numerical value or range within such percent ranges, that is absorbed to substrate is removed (eluted) or is removable (elutable) from the substrate in a form amenable to a subsequent analysis or application. The term "substantially complete" and grammatical variants thereof, when used in reference to recovery, means that 75-80% or more (e.g., 80-90%, or 90-95%) of the total amount of one or more biomolecules or any numerical value or range within such percent ranges absorbed to the substrate is removed (eluted) or recoverable from the substrate. Thus, for example, where an initial amount of peptide absorbed to a substrate is 10 micrograms (jig), recovery of the peptide in part from the substrate would result in obtaining 2.5 to 5.0 micrograms peptide free of substrate. Peptide recovery that is substantially complete would result in recovering 7.5 to 8.0 micrograms or more peptide (8.0 to 9.0 micrograms, 9.0 to 9.5 micrograms, etc.) free of substrate. The unrecovered portion either remains absorbed or adsorbed to the substrate or is no longer available for recovery due to degradation.

The concentration of a biomolecule eluted or recovered from an elutable elastomeric substrate will typically be greater than the concentration of the biomolecule eluted or recovered from an elutable non-elastomeric substrate. The reason for this difference is that an elastomeric substrate having a biomolecule absorbed thereto can be hydrated with a fluid, and the fluid expelled from the substrate by compression of the substrate (e.g., compression via force applied by a centrifugal field or a pistion). The fluid volume used for elution or recovery from an elastomeric substrate can be less than for a non-elastomeric substrate. The volume difference for an equivalent amount of absorbed biomolecule can be as much as 5-100-fold or more. That is, for an equal amount of a biomolecule initially absorbed to a substrate, the biomolecule eluted from an elutable elastomeric substrate will be 5-100-fold or more concentrated than the same biomolecule eluted from an elutable non-elastomeric substrate. When an elution liquid is applied to a porous or semiporous non-elastomeric substrate, the pores or interstitial space is retained as an unstirred solvent layer. In other words, fluid flow from the pores to the external space, where the liquid can be recovered, is inefficient due to the inability to induce mixing by compression or other means. In contrast, the ability to compress an elutable elastomeric substrate leads to expelling the elution liquid from the substrate, thereby facilitating biomolecule elution and recovery at a higher concentration and in a smaller volume.

As a particular example, proteins in a 150 ul serum sample absorbed to a 5 mm high.times 6 mm wide cylindrical elutable elastomeric porous substrate can be eluted and recovered from this substrate with the same volume of elution or recovery liquid as the original sample volume (i.e., 150 ul). The concentration of protein eluted or recovered from an elutable elastomeric porous substrate will typically be about 50-95% of the protein concentration in the original sample. In contrast, the volume of elution or recovery liquid needed to elute or recover protein from a 10 ul serum sample absorbed to an elutable non-elastomeric porous substrate will be signicantly more, for example, 400 ul or more, depending on the desired protein yield. Consequently, the concentration of protein eluted or recovered from an elutable non-elastomeric porous substrate will typically be less than that of an elutable elastomeric porous substrate, on the order of about 1-10% of the protein concentration in the original sample.

Typical concentrations of biomolecules eluted or recovered range from about 1 ng/ml to about 1 mg/ml, or any numerical value or range within this range. For peptides, typical elution and recovery concentrations from absorbed substrate are from sub-nanogram to milligrams per mL, or any numerical value or range within such a range. For serum peptides, typical elution and recovery concentrations from absorbed substrate are approximately equivalent to (e.g., 90% or more) or less than the original serum protein concentration, i.e., serum has 10% (100 mg/mL) protein. For nucleic acid eluted or recovered from substrate following peptide elution as set forth herein, typical elution and recovery is approximately 50% or more of the original amount of nucleic acid absorbed to substrate.

For nucleic acid, typical concentrations range from about 0.01 ng/ml to 1 ng/ml, or greater. Nucleic acid concentration of 1 ug/ml or more is suitable for certain analysis without the need for concentration. Nucleic acid can be eluted or recovered at a concentration of 10 ng/ml to about 50 ng/ml, 50 ng/ml to about 100 ng/ml, 100 ng/ml to about 250 ng/ml, 250 ng/ml to about 500 ng/ml, 500 ng/ml to about 1000 ng/ml, 1000 ng/ml to about 1500 ng/ml, 1500 ng/ml to about 2000 ng/ml, 2000 ng/ml to about 2500 ng/ml, 2500 ng/ml to about 3000 ng/ml, 3000 ng/ml to about 3500 ng/ml, 3500 ng/ml to about 4000 ng/ml, 4000 ng/ml to about 4500 ng/ml, 4500 ng/ml to about 5000 ng/ml, 5000 ng/ml to about 5500 ng/ml, 5500 ng/ml to about 6000 ng/ml, 6000 ng/ml to about 6500 ng/ml, 6500 ng/ml to about 7000 ng/ml, 7000 ng/ml to about 8000 ng/ml, 8000 ng/ml to about 9000 ng/ml, 1 µg/ml to about 50 µg/ml, 50 µg/ml to about 100 µg/ml, 100 µg/ml to about 250 µg/ml, 250 µg/ml to about 500 µg/ml, 500 µg/ml to about 1000 µg/ml, 1000 µg/ml to about 1500 µg/ml, 1500 µg/ml to about 2000 µg/ml, 2000 µg/ml to about 2500 µg/ml, 2500 µg/ml to about 3000 µg/ml, 3000 µg/ml to about 3500 µg/ml, 3500 µg/ml to about 4000 µg/ml, 4000 µg/ml to about 4500 µg/ml, 4500 µg/ml to about 5000 µg/ml, 5000 µg/ml to about 5500 µg/ml, 5500 µg/ml to about 6000 µg/ml, 6000 µg/ml to about 6500 µg/ml, 6500 µg/ml to about 7000 µg/ml, 7000 µg/ml to about 8000 µg/ml, 8000 µg/ml to about 9000 µg/ml, or about 10 mg/ml nucleic acid, or any numerical value or range within such ranges.

Exemplary techniques for determining quantity or concentration of a peptide or nucleic acid using size fractionation (e.g., chromatography such as HPLC and FPLC, and gel fractionation by electrophoresis) and peptide or nucleic acid colorimetric stains (e.g., PicoGreen, Molecular Probes, Inc. Eugene Oreg.). Inimunoassays such as ELISA and RIA can be used to quantify or detect specific proteins. Nucleic acid can also be calculated by UV spectroscopy. Accordingly, the yield of biomolecule following elution or recovery from substrate can be readily ascertained using various techniques known in the art.

Substrates generally, and elastomeric substrates in particular, can be any size, shape or dimension convenient for the intended biomolecule storage or preservation function. The size will be determined, in part, by the volume of biomolecule to be stored or preserved, and the desired format for storage or preservation, for example, a multi-well storage unit amendable to automation. The size will therefore be determined in part on the volume or quantity of sample to be absorbed to the substrate. In order to minimize the volume of elution or recovery liquid, typically substrate will have sufficient size to absorb the sample, but not be so large as to result in the undesirable dilution of the eluted or recovered biomolecule. Substrate size will therefore be determined at least in part by the amount of biomolecule to be absorbed and the concentration of the biomolecule desired in the elution or recovery liquid.

Substrate shape will be determined in part by any housing (e.g., vessel or tube) or storage unit containing the substrate. Exemplary sizes range from 1-5 $cm^2$, 5-10 $cm^2$ for two-dimensional substrates. For three-dimensional substrates, such as elastomeric substrates including sponges and foams, volumes will range from 1-5 $mm^3$, 5-10 $mm^3$, 10-20 $mm^3$, 20-30 $mm^3$, 30-50 $mm^3$, 50-100 $mm^3$, 100-200 $mm^3$, 200-500 $mm^3$, 500-1000 $mm^3$, 1-5 $cm^3$, 5-10 $cm^3$, 10-20 $cm^3$, 20-30 $cm^3$, 30-50 $cm^3$, 50-100 $cm^3$, 100-200 $cm^3$, 200-500 $cm^3$, or more, or any numerical value or range within such ranges. An exemplary elastomeric substrate is a 5 mm high×6 mm wide cylinder. Exempary non-limiting substrate shapes include rectangular, square, cylindrical, circular, spherical and triangular.

A "recoverable" biomolecule refers to a biomolecule that is amenable to a subsequent analysis or application. Thus, where a subsequent analysis involves sequencing a recovered nucleic acid, it is desirable that the substrate inhibit degradation of the nucleic acid so that the sequence can be accurately determined without purification following recovery. However, where an analysis is not affected by biomolecule unfolding or degradation, there is no need for the substrate to preserve the absorbed biomolecule in its native form. The recovery of a such a biomolecule from substrate, when expressed as a percent, reflects the amount of biomolecule recovered that is amenable to a subsequent analysis or application. Typical recovery percents for degraded biomolecules can therefore reflect the inclusion of fragments and degradation products of the recovered biomolecule.

The term "recoverable" also refers to a biomolecule absorbed to a substrate that can be selectively or preferentially eluted or removed from substrate under certain conditions without eluting or removing substantial amounts of one or more other biomolecules absorbed to the substrate. For example, peptide absorbed to a substrate can be eluted from the substrate without eluting substantial amounts of a nucleic acid absorbed to the substrate. Thus, a peptide absorbed to a substrate can, at least in part, be recovered from the substrate while a majority of a nucleic acid absorbed to the substrate remains absorbed to the substrate. Elutable substrates therefore include materials in which a biomolecule can be eluted from the substrate selectively, preferentially, simultaneously or sequentially—e.g., an absorbed peptide is eluted first from the substrate followed by subsequent nucleic acid elution from the substrate, or both absorbed protein and adsorbed nucleic acid are eluted from substrate simultaneously. As an example, an aqueous liquid such as water is applied to the substrate and absorbed protein eluted and recovered from substrate, followed by applying an alkaline solution to the same substrate, which in turn elutes absorbed nucleic acid from the substrate. Conditions for selective, preferential (e.g., differential) or sequential, as well as simultaneous elution of peptide and nucleic acid are as set forth herein.

Biomolecules (e.g., peptide or nucleic acid) can be eluted or recovered from substrate by fluid hydration. Hydration techniques include addition of a liquid to a substrate, referred to herein as an "elution liquid," or "elution solution," "recovery liquid," or "recovery solution." Elution/Recovery liquids or solutions include, for example, liquids suitable for elution or recovery of peptide from substrate and liquids suitable for elution or recovery of nucleic acid from substrate. Liquids suitable for biomolecule elution can be the same or different from liquids suitable for biomolecule recovery. Liquids suitable for elution or recovery of peptide can be the same or different composition than liquids suitable for elution or recovery of nucleic acid. If both peptide and nucleic acid are present on the substrate, and selective, preferential or differential (separate) elution of peptide and nucleic acid from substrate is desired, the elution liquids for peptide and nucleic acid typically differ from each other; although preferential or differential recovery/elution of peptide and nucleic acid from substrate can be achieved by varying other parameters, such as hydration technique, temperature, and incubation time, and in the case of liquids suitable for elution or recovery, the composition, pH, temperature, and incubation time of liquid and substrate.

Thus, in another embodiment, the invention provides a biomolecule (e.g., peptide) and an elutable elastomeric substrate, wherein the composition is substantially free of moisture and the biomolecule (e.g., peptide) is absorbed to the elastomeric substrate, wherein the biomolecule (e.g., peptide) optionally resists degradation as compared to unabsorbed peptide, wherein at least a portion of the peptide is recoverable or elutable from said elastomeric substrate, and an aqueous liquid. The invention further provides, in another embodiment, a composition including biomolecules (e.g., peptide and a nucleic acid) and an elutable substrate, wherein the composition is substantially free of moisture and the biomolecules (e.g., peptide and a nucleic acid) are absorbed or absorbed to the substrate, wherein one of the biomolecules (e.g., peptide or nucleic acid) optionally resists degradation as compared to unabsorbed biomolecules (e.g., peptide or nucleic acid), wherein at least a portion of the biomolecule (e.g., peptide or nucleic acid) is recoverable or elutable from said substrate, and an aqueous liquid. In various aspects, the aqueous liquid is suitable for elution or for recovery of at least a portion of the peptide or at least a portion of the nucleic acid from the elutable substrate. In additional aspects, the aqueous liquid is suitable for selective, preferential (e.g., differential) sequential, or simultaneous elution or recovery of at least a portion of the peptide or at least a portion of the nucleic acid from the elutable substrate.

Exemplary elution/recovery liquids are aqueous. A non-limiting example is water, which can be used to elute or recover peptide absorbed to a substrate. Such liquids can be a water-based solution that can but need not be pH buffered to maintain pH within a given range. A particular non-limiting example is a pH buffered liquid having a pH within about 5 to 9, or any numerical value or range within such ranges (e.g., pH 5 to 8, 6 to 8, 7 to 8, or within these ranges, e.g., 7.2 to 7.8, 7.4 to 7.6) which can be used to elute or recover peptide from a substrate without eluting substantial amounts of nucleic acid from substrate.

An additional non-limiting example of an elution/recovery liquid is an alkaline liquid, for example, an aqueous alkaline solution having a pH of about 10-12 (i.e., 9.8-12.2), or any numerical value or range within such ranges more particularly, having a pH within a range of pH 10 to 12, pH 11 to 12, pH, 11.3 to 11.8, or pH 11.4 to 11.7, most particularly an alkaline solution having a pH of 11.4, 11.5, 11.6, 11.7, or 11.8. Such an alkaline liquid is suitable for elution or recovery of nucleic acid absorbed to substrate. Such an alkaline liquid is also suitable for elution or recovery of peptide absorbed to substrate.

Elution and recovery of biomolecules can be performed above, below or at ambient (room) temperature. Exemplary non-limiting temperatures include, for example, 5-10° C., 10-15° C., 15 to 20° C., 20-25° C., 25-32° C., 30-40° C., 40-50° C., 50-60° C., 60-70° C., 70-80° C., or more, or any numerical value or range within such ranges.

In the non-limiting example of a peptide absorbed to an elastomeric elutable substrate (e.g., sponge/foam), the substrate can be hydrated, e.g., an appropriate quantity of water is applied or contacted to peptide absorbed sponge (e.g., a volume equal to the sponge void volume), sufficient to contact the sponge surface area and permeate the sponge. The hydrated sponge is optionally incubated for a period of time in the presence of water and optionally compressed (squeezed) or centrifuged one or more times in order for the water to elute peptide from the sponge substrate. The elution solution containing peptide can be withdrawn while the sponge is compressed or following centrifugation, and the recovered peptide can be subjected to a subsequent analysis, if desired.

Nucleic acid, if also present on the elastomeric elutable substrate (e.g., sponge/foam) with peptide, can be eluted from substrate after elution of peptide from the substrate. If it is desired to elute peptide from the same substrate in which it is desired to elute nucleic acid, peptide can be eluted selectively or preferentially from the substrate first, as described herein for example, the peptide recovered, which is followed by subsequent elution of nucleic acid from the substrate as described herein.

In the non-limiting example of a nucleic acid absorbed to an elastomeric elutable substrate (e.g., sponge/foam), the substrate can be hydrated, e.g., an appropriate quantity of liquid suitable for elution of nucleic acid is applied to or contacted with the sponge, sufficient to contact the sponge surface area and permeate the sponge. For example, an alkaline liquid (e.g., an aqueous alkaline solution having a pH of about 10-12, i.e., 9.8-12.2, or any numerical value or range within such ranges) can be applied or contacted to nucleic acid absorbed sponge. The hydrated sponge is optionally incubated for a period of time in the presence of alkaline liquid and optionally compressed (squeezed) or centrifuged one or more times in order for the liquid to elute nucleic acid from the sponge substrate. The alkaline elution solution containing nucleic acid can be withdrawn while the sponge is compressed or following centrifugation, and the recovered nucleic acid can be subjected to a subsequent analysis, if desired.

Peptide absorbed to substrate is typically eluted with water having a pH between about 6 and 8. However, peptide absorbed to substrate can also be eluted with an alkaline liquid having a pH of about 10-12. Thus, peptide absorbed to substrate can also be eluted from substrate with water or an alkaline liquid. Where both peptide and nucleic acid are absorbed to a substrate, if it is desired to elute peptide selectively or preferentially from substrate, without also eluting substantial amounts of nucleic acid, peptide can be eluted and recovered from substrate prior to eluting or recovering nucleic acid. Alternatively, where both peptide and nucleic acid are absorbed to a substrate, if it is desired to elute both peptide and nucleic acid, peptide and nucleic acid can be eluted from substrate with an alkaline liquid having a pH of about 10-12.

More particularly, DNA can be eluted from substrate by hydration with an elution liquid having a pH of between about 10 and about 12 at ambient (room) temperature, without toxic materials or organic solvents, which is a process that is automation-compatible. The recovered nucleic acid is typically high-quality and is amenable to a subsequent application or analysis. Eluting nucleic acids absorbed to a substrate can include one or more of 1) providing an elutable substrate having absorbed to the substrate a nucleic acid or sample containing nucleic acid; 2) hydrating the absorbed substrate with an elution liquid (i.e., applying or contacting the substrate with an elution liquid) having a pH of between about 10.0 and about 12.0 (e.g., a pH of between 9.8-12.2, more particularly about 11.4 and about 11.8), and eluting nucleic acid from the hydrated substrate; and 3) optionally recovering the eluted nucleic acid. This process can be repeated using the same substrate using the same or a different elution or recovery liquid.

Without being limited to any particular theory, alkaline pH may function to neutralize the absorbed nucleic acid by deprotonation, such that the electrostatic interaction between the nucleic acid and the substrate is weakened and the nucleic acid can be eluted. Alternately, the alkaline pH may act by a different mechanism, as it should be noted that increasing the pH of the solution may also increase charge on nucleic acids, primarily due to ionization of G and T residues, which may alter the interaction between nucleic acids and any substrate to which they are absorbed.

Nucleic acid eluted with an elution liquid having a pH of between about 10 and about 12 are double stranded, or single stranded, or in a mixture. The form of the eluted nucleic acid depends on various factors including, but not limited to, pH of the elution buffer, buffer strength, properties of the substrate, and quality of the nucleic acid-containing sample. Room temperature elution using an elution liquid having a pH of about pH 10, elutes nucleic acid that is predominantly in a double stranded form (e.g., dsDNA). Room temperature elution using an elution buffer having a pH of about pH 12, elutes nucleic acid that is predominantly in a single stranded form (e.g., ssDNA). Without wishing to be limited by any theory, it appears that elution at more alkaline pH, (e.g., above about pH 12.0), elutes nucleic acids that are predominantly in single stranded form; a subsequent neutralization of the eluate may permit or facilitate pairing of any complementary strands to generate double-stranded nucleic acid.

In order to reduce exposure of eluted or recovered nucleic acid to alkaline pH, the alkaline liquid can optionally be "quenched." A "quench" is a process undertaken to reduce the pH. For example, pH can be reduced by adding an acidifying agent or performing a buffer exchange with a buffer having a pH of between about 5.0 and 10.0 pH units, or between about 8.0 and 9.0 pH. The "quench" may occur as part of a subsequent analysis or application. For example, the pH is reduced, for example, by acidification, desalting, or buffer exchange as part of a protocol to achieve a desired pH or buffer composition for carrying out a subsequent analysis.

Incubation of an elution or recovery liquid with substrate can be brief, for example, on the order of 1-5, 5-25, 25-60, 60-120 seconds, or any numerical value or range within such ranges; an intermediate amount of time, for example, 1-5, 5-25, 25-60, 60-120 minutes, or any numerical value or range within such ranges, or an extended period of time, for example, 1-5, 5-25, 25-60, 60-120 hours, or any numerical value or range within such ranges. Incubation times are typically less where the elutable substrate is elastomeric since the biomolecule can be recovered by hydrating the substrate and agitating or rapidly compressing the substrate one or more times.

As used herein, the term "hydrate" or grammatical variations thereof, when used in reference to a substrate, a biomolecule or a substrate to which a biomolecule has been absorbed, means a process in which moisture is added to substrate, a biomolecule or a substrate to which a biomolecule has been absorbed. Hydration can occur by applying or contacting substrate, biomolecule or a substrate to which a biomolecule has been absorbed with an aqueous or other liquid.

As used herein, the term "apply" and grammatical variations thereof, when used in the context of a liquid (e.g., an elution or recovery liquid) and a substrate, a biomolecule or a substrate to which a biomolecule has been absorbed or adsorbed, means that the liquid comes into physical contact with the substrate, biomolecule or a substrate to which a biomolecule has been absorbed or adsorbed. Where the liquid is applied to substrate to which a biomolecule has been absorbed or adsorbed, this physical contact allows a biomolecule (e.g., peptide or nucleic acid) to be at least partially removed, detached (eluted) or recovered from the substrate, provided appropriate elution conditions are used. Thus, in this context the terms "apply" and "contact" are equivalent.

The volume of liquid sufficient to adequately hydrate an elutable substrate to elute or recover a biomolecule absorbed to the substrate will be determined by the substrate material and the subsequent application or analysis to which the biomolecule is subjected. In the particular embodiment of an elutable elastomeric substrate, elution or recovery liquid volumes can range from a volume equivalent to the volume of the substrate in a compressed state, to the volume of the elutable elastomeric substrate in an uncompressed state, or more. Thus, in order to minimize the volume of elution or recovery liquid, an elutable elastomeric substrate may be a more appropriate substrate than a non-elastomeric elutable substrate. A minimal volume of liquid to elute or recover a biomolecule absorbed to an elutable elastomeric substrate involves the use of a volume equivalent to the compressed volume of the elastomeric substrate. Minimizing the volume of elution or recovery liquid provides a more concentrated form of eluted or recovered biomolecule.

For elution of nucleic acid, in one embodiment, the absorbed substrate is hydrated with an alkaline elution buffer, which releases nucleic acid from the substrate into the elution liquid. Optionally, the nucleic acid-containing eluate (nucleic acid in elution liquid) is then separated from the substrate and recovered. The eluate is optionally neutralized with equilibration buffer (quenched) to stabilize the nucleic acid for storage in solution. The nucleic acid-containing eluate can be used directly for subsequent analysis, or nucleic acid may be recovered and/or separated from the elution buffer, e.g., by standard buffer exchange methods, by precipitation, or by binding to a nucleic acid-binding material. Elution from substrate can be repeated one or more times, and the nucleic acid-containing eluates combined to enhance the yield of nucleic acid.

As used herein, the term "substantially free," and grammatical variations thereof, when used in reference to moisture content of a substrate, means that the substrate has less than about 25% moisture content (i.e., 23-27%) by mass, relative to the total mass of the absorbed substrate. Typically, moisture content will be less than 25%, for example, less than 20-25%, 15-20%, 10-15%, 5-10%, or less than 2-5%, e.g., 1-2%, or any numerical value or range within such percent ranges. Moisture content can be determined using a standard Karl Fischer titration (see, for example, U.S. Pat. No. 5,102, 804).

As used herein, the term "biomolecule" refers to any molecule typically found or produced by a living or non-living organism, or a sample containing such a material. Biomolecules therefore include organic molecules, such as peptides (protein), nucleic acid (polynucleotides), carbohydrates, sugars, fatty acids, lipids, as well as combinations thereof and in combination with inorganic molecules. Typically, a sample present or produced by a living or non-living organism includes a plurality of such biomolecules. A biomolecule can therefore be a part of a larger sample, which can include one or more peptide, nucleic acid, carbohydrate, sugar, fatty acid and lipid alone or in any combination. Thus, a peptide or nucleic acid absorbed to a substrate may or may not include one or more additional biomolecules absorbed to the substrate. Consequently, a given biomolecule absorbed to a substrate may be alone or in a combination with one or more additional biomolecules absorbed to the substrate. For example, a "sample" from a living or non-living organism will typically contain a plurality of biomolecules, unless the sample has been subjected to enrichment or purification. Biomolecules include liquid samples in which one or more molecules are dissolved or suspended in the liquid sample.

Biomolecules can be obtained, isolated or derived from, inter alia, living or non-living organisms, or anything produced by living or non-living organisms. Specific non-limiting examples include mammalian animals (e.g., primates including humans, apes, chimpanzees, gibbons; and farm and domestic animals including canine, feline, bovine, equine and porcine), which are typically warm-blooded, and non-mammalian animals (e.g., reptilian and avian), which are typically cold-blooded. Biomolecules can be isolated or obtained from tissues, organs, cells. Biomolecules can be isolated or obtained from microorganisms, including, for example, bacteria, fungi, parasites, virus and mycoplasma.

Biomolecules can include mixtures of cells (e.g., a tissue or organ biopsy), a particular cell type (e.g., hematopoetic cells), or a part of a cell, such as a protein or nucleic acid extract from a mixture of cells or particular cell type. The biomolecule can therefore be from or derived from any kind of cell, including prokaryotic and eukaryotic cells. A substrate may therefore have absorbed thereto any type of prokaryotic or eukaryotic cell, a part of a cell, and may include a mixture or collection of cells.

Cells include unicellular eukaryotes, multicellular eukaryotes, or a sample of cells (e.g, a tissue or organ sample or biopsy) from a multicellular eukaryote. The eukaryotic cell can be, for example, a blood cell or a tissue cell. Prokaryotic cells include eubacteria and archaebacteria, and gram-positive and gram-negative bacteria. The prokaryote can be a pathogenic or non-pathogenic organism. Biomolecules include a sample or material from a single or individual organism (e.g., a human subject), a single species (e.g., a subpopulation of human subjects), a plurality of organisms, or a plurality of species.

Biomolecules include a sample, also referred to as material, obtained from an organism. Biomolecules include a sample obtained from a subject. Biomolecules include tissue, blood, serum, plasma, cerebral spinal fluid, hair, fur, saliva, sputum, semen, urine, stool, mucous, skin, a benign or malignant tumor or growth, biopsied organ, tissue or any other type of cell, organ or tissue sample or material, optionally in solution or in suspension.

The term "subject" as used herein refers to animals, typically mammalian animals, such as a human, non human primates (apes, gibbons, chimpanzees, orangutans, macaques), domestic animals (dogs and cats), farm animals (horses, cows, goats, sheep, pigs), and experimental animals (mouse, rat, rabbit, guinea pig). Subjects include animal disease models. Subjects further include animals having or at risk of having a disease. A sample obtained from a subject can be stored for subsequent screening for a genetic disease or physiological disorder, or a predisposition towards a genetic disease or physiological disorder. Specific non-limiting examples of genetic diseases or physiological disorders include a genetic disorder, a hyperproliferative disorder, an immunological disorder or a microbial infection. A sample obtained from a subject that is incarcerated, has been incarcerated or is at risk of incarceration (has been previously incarcerated or convicted) can be stored for subsequent screening for identification of for forensic purposes.

Biomolecules can be derived or obtained from a plant or plant part, for example, leaf, stem, stalk, pollen, root, branch, flower, seed, bulb, spore or other plant material. Biomolecules are present in food, forensic samples, agricultural samples and products as well as environmental samples (e.g., soil, dirt, fresh water, salt water or waste water, landfill material, garbage or waste).

Biomolecules can also be artificial or synthetically produced. For example, synthetic methods of producing peptides, nucleic acids, fats, lipids, carbohydrates are known in the art.

The term "peptide," refers to any length of two-or more amino acids linked by an amide bond. A peptide can also be referred to herein, inter alia, as a protein, polypeptide, or an amino acid sequence. Peptides can form intra or intermolecular disulfide bonds. Peptides can also form multimers with the same or different peptides, or other biomolecules. Peptides can be modified, for example, phosphorylated, glycosylated, ubiquitinated, or methylated. A peptide can have one or more non-natural or derivatized amino acid residues linked to the two-or more amide linked amino acids. Peptides include chimeric proteins in which two or more amino acid sequences are linked together that do not naturally exist in nature. Peptides include any length of two-or more amino acids bound by an amide bond that has been conjugated to a distinct moiety.

Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and a-anomeric forms thereof. The two or more purine- and pyrimidine-containing polymers are typically linked by a phosphoester bond or analog thereof. Phosphoester bonds can be substituted with a structure that enhances stability of the oligonucleotide. Specific non-limiting examples of such substitutions include phosphorothioate bonds, phosphotriesters, methyl phosphonate bonds, short chain alkyl or cycloalkyl structures, short chain heteroatomic or heterocyclic structures and morpholino structures (see, for example, U.S. Pat. Nos. 5,034,506; 5,223,618; and 5,378, 825).

Nucleic acid includes linear or circular DNA and RNA, single strand, double or triplex forming, in any conformation, such as zDNA. Double or triplex forming nucleic acid include DNA-RNA hybrids. Nucleic acids also include protein nucleic acids (PNA) formed by conjugating bases to an amino acid backbone (Hyrup et al., Bioorg. Med. Chem. 4:5 (1996)). The neutral backbone of PNAs allows specific hybridization to DNA and RNA under conditions of low ionic strength. The synthesis of PNA oligomers can be performed using standard solid phase peptide synthesis protocols (see, e.g., Perry-O'Keefe et al., Proc. Natl. Acad. Sci. USA 93:14670 (1996)). PNAs hybridize to complementary DNA and RNA sequences in a sequence-dependent manner, following Watson-Crick hydrogen bonding.

Nucleic acids can be wild-type, including polymorphisms, mutant, or synthetic, either sense or antisense. Nucleic acids further include eukaryotic and prokaryotic genes, plasmids and vectors, artificial chromosomes, as well as viral DNA or RNA. Whenever an oligonucleotide is represented by a sequence of letters, such as "ATGCCTG," the nucleotides are in a 5' to 3' orientation, from left to right.

DNA refers to deoxyribonucleic acid containing deoxyribose and phosphate groups, such as naturally occurring adenine (A), thymine (T), guanine (G) and cytosine (C). DNA includes genomic, cDNA, EST (expressed sequence tag) and organellar DNA (e.g., mitochondrial and chloroplast DNA). DNA bases may be modified by, e.g., alkylation (e.g., methylation) or deamination, generating modified bases such as N-6-hydroxylaminopurine (HAP), 5-methylcytosine, formamidopyrimidines, 8-hydroxyguanine, and 5,6 hydrated thymines.

RNA refers to ribonucleic acid containing ribose and phosphate groups, such as naturally occurring adenine (A), cytosine (C), guanine (G) and uracil (U). RNA includes transcript, message (mRNA), ribosomal (rRNA), transfer RNA (tRNA), and small RNAs such as small nuclear RNA (snRNA), small nucleolar RNA (snoRNA), and micro-RNA (miRNA) including small interfering (siRNA) and small temporally regulated RNA (stRNA). RNA bases can be modified by, e.g., generating modified bases such as N2,2,7, tri-methylguanosine (m3G), 2'-O-methyladenosine (A3), 2'-O-methylcytosine (C3), 2'-O-methylguanosine (G3), 2'-O-methyluridine (U3), pseudouridine (F), N6-methyladenosine (A6), 2-methylguanosine (G2).

Synthetic bases can be included in nucleic acid. Specific non-limiting examples include xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil, 5-trifluoro cytosine and tritylated bases.

Samples including biomolecules, such as peptide or nucleic acid eluted or recovered from substrate, can subsequently be used for any analytical, functional or structural analysis or application, if desired. As used herein, "subsequent analysis" or "subsequent application" means any analytical, functional or structural procedure or protocol which may be performed on a biomolecule eluted or recovered from substrate. Subsequent analysis means that an eluted or recovered biomolecule be amenable to such analysis. Of course, this is not to say that biomolecules need be eluted or recovered in order to be amenable to a subsequent analysis or application. For example, a biomolecule absorbed or adsorbed to a substrate can be analyzed in situ, wherein the biomolecule is analyzed without elution or recovery from the substrate. As an example, elution liquid added to peptide or nucleic acid absorbed to the substrate, and regents for subsequent analysis (e.g. colorimetric reagents) are added to the same vessel housing the substrate. Thus, a subsequent analysis or application does not require elution or recovery of a biomolecule from substrate, but if a biomolecule is eluted or recovered from substrate, it will be in a form amenable to a subsequent analysis or application.

Non-limiting examples of subsequent analysis which may be performed on biomolecules include enrichment, purification, sequencing, molecular weight analysis, isoelectric point analysis, charge density analysis, structural analysis or crystallization. Additional examples of subsequent analysis include functional assays, such as binding affinity or enzymatic or catalytic activity.

Non-limiting examples of subsequent analysis which may be performed on eluted or recovered peptide or nucleic acid include electrophoresis, purification, sequencing (e.g., cDNA or genomic), molecular weight analysis, structural analysis, functional assays, such as binding or hybridization. Additional examples of nucleic acid subsequent analysis include genotyping, fingerprinting, expression of recovered nucleic acid (transcription or translation), cloning or other genetic manipulation. Further examples of nucleic acid subsequent analysis include synthesis or amplification (e.g., polymerase chain reaction, PCR, ligase chain reaction, LCR, reverse transcriptase initiated PCR, rtPCR and whole genomic amplification via PCR-based or isothermal amplification methods), DNA or RNA hybridization techniques including restriction fragment length polymorphism, RFLP, sequencing, STR and SNP analysis, and applications to microarrays, gene chips, and any high-throughput or automated application, analysis or process.

Biomolecules can optionally be enriched or purified, and subjected to a subsequent analysis or application. For example, nucleic acid can be purified prior to cloning, amplification or other genetic manipulation. Biomolecules can also be subjected to labeling reactions, such as peptide or nucleic acid labeled with a radioisotope for use as a probe or a primer. More specifically, for example, nucleic acid or peptide recovered from a blood sample absorbed to a substrate may be sequenced or size fractionated on an agarose or polyacrylamide gel for purification, enrichment or for analysis.

"Enrichment" and grammatical variations thereof refers to increasing the proportion of one or more biomolecules in a sample relative to other substances or materials present in the sample. Thus, an enriched biomolecule is present in a greater proportion relative to other substances, as compared to the unenriched form of the biomolecule. "Purification" and grammatical variations thereof refers to separating a biomolecule from one or more other substances or materials, including biomolecules that may be present in a sample. Purification can also refer to separating or fractionating biomolecules in a sample, for example, to select a nucleic acid having a desired characteristic such as a particular sequence, size, structure or conformation. The terms therefore differ with respect to the relative proportion of the referenced biomolecule(s), a purified biomolecule(s) being in a greater proportion relative to other substances than an enriched biomolecule(s).

Biomolecule enrichment and purification techniques are known in the art. For example, using chromatography, eluted or recovered nucleic acid or peptide can be fractionated on an agarose or polyacrylamide gel to separate on the basis of size, structure or conformation. Eluted or recovered nucleic acid or peptide can be separated or purified using affinity chromatography, e.g., Sephadex, polyA, or antibody-affinity columns.

Nucleic acid can be purified following elution or recovery of human blood absorbed to substrate (e.g., an elastomeric substrate such as a sponge, or FTA®, rag paper or IsoCode™), using commercially available technologies including DNA-binding magnetic beads, phenol:chloroform extraction, or nucleic acid-binding chromatography columns (e.g., available from Qiagen and Gentra Corporation). Hybridization can enrich or purify nucleic acid according to sequence, and any nucleic acid hybridized thereto recovered. These, and other, methods for purification, separation, or fractionation of nucleic acid and peptide are known in the art.

Substrates may include or exclude additional components so that a biomolecule (e.g., peptide or nucleic acid) eluted or recovered from a substrate is enriched or purified relative to the absorbed or adsorbed biomolecule. For example, an elutable substrate may be modified to include a binding agent, such as an antibody that binds to an antigen. This antibody can be linked directly to the substrate surface via standard linkage chemistries (as described herein, for example, and others known in the art). Absorbing a biological sample that contains an antigen which binds to the antibody bearing substrate results in binding of the antigen to the antibody, and adsorption of the antigen to the substrate. Under appropriate elution or recovery conditions, the process of absorption is reversed, absorbed biomolecule is eluted from the substrate, while the antigen which binds to the antibody bearing substrate remains bound. In this manner, the antigen that binds to the antibody-bearing substrate is removed or depleted from any eluted or recovered biomolecule. By modifying elutable substrates to include one or more binding agents, contaminating substances such as other biomolecules that are undesirable or interfere with a subsequent application or analysis, can be retained by the substrate, leading to removal of such substances from the eluted or recovered biomolecule. Accordingly, biomolecules and biological samples eluted from substrate modified to include one or more binding agents can be enriched or purified relative to the biomolecule sample absorbed to the substrate. Of course, specifically excluding one or more binding agents from substrate will allow for elution or recovery of a biomolecule that binds to the excluded binding agent under appropriate conditions.

The term "binding agent" refers to a molecule having a selective or non-selective affinity for other substances. Non-selective binding agents may be used to bind a genus of substances, such as protein or nucleic acid. A particular non-limiting example of a non-selective binding agent includes protein A, which binds to immunoglobulins. A sample absorbed to protein A conjugated substrate, when eluted from the protein A conjugated substrate, will contain less immunoglobulin.

Yet another particular non-limiting example of a non-selective binding agent includes a mixture of single strand nucleic acid, such as a fragmented genomic or cDNA library, which can be attached to a substrate via a covalent or other high-affinity bond such that it is not eluted by the elution or recovery liquid. The nucleic acid attached to a substrate can hybridize to nucleic acid present in a sample absorbed to the substrate. A sample eluted from such a substrate will contain less nucleic acid than the original sample absorbed to the substrate.

Selective binding agents include antibodies, ligands, receptors and specific nucleic acid sequences that hybridize to a target nucleic acid sequence that may be present in a sample absorbed to a substrate. Particular non-limiting examples of selective binding agents include anti-immunoglobulin antibodies, which can selectively remove or deplete immunoglobulins (e.g., IgG, IgA, IgM, IgE, or IgD) from an eluted or recovered sample; anti-albumin antibodies which can selectively remove or deplete albumin from an eluted or recovered sample; and anti-clotting factor antibodies which can selectively remove or deplete clotting factors (e.g., Factors I-X) from an eluted or recovered sample, to name a few.

Binding agents may be attached to elutable substrates using a variety of methods. For example, ionic or covalent linkages can be used to attach the binding agent (e.g., antibody, ligand, receptor, etc.) to the substrate. Covalent linkages can be formed with a number of functional groups on synthetic and biological materials. Particular non-limiting examples of such functional groups include amino groups, carboxyl groups, sulphydryl groups, hydroxyl groups, imidazole groups, phenolic groups, thiol groups, threonine groups and indole groups. Particular non-limiting examples of chemical reactions resulting in a covalent linkage include diazotization (Substrate-N=N-Binding Agent); amide bond formation (Substrate-CO—NH-Binding Agent); alkylation or arylation (Substrate-$CH_2$—NH-Binding Agent and Substrate-$CH_2$—S-Binding Agent); Schiff's base formation (Substrate-CH=N-Binding Agent); amidation (Substrate-CNH—NH-Binding Agent); thio-disulphide interchange (Substrate-S—S-Binding Agent); and carrier binding with bifunctional reagents (Substrate-O($CH_2$)$_2$—N+CH($CH_2$)$_3$ CH=N-Binding Agent). Carrier binding with bifunctional reagent produces a "leash" that allows the binding agent (e.g., antibody) to rotate in three-dimensional space with less restriction so that binding can take place at a lower energy. The "leash" concept can be applied to any covalent or ionic method with suitable modification of the surface of the substrate. Other methods such as UGI (Uracil Glycosylase Inhibitor), mercury-antibody interchange, and radiation induced coupling have been used to attach binding agents, such as antibodies and nucleic acids, to surfaces.

Substrates and biomolecules (e.g., peptide or nucleic acid) as well as elution and recovery liquids can include or exclude particular treatments or additives set forth herein, depending on the desired storage, preservation, elution, recovery or other characteristics, or the particular subsequent analysis or application that the biomolecule is or is likely to be subjected. Exemplary treatments and additives include, for example, buffers, such as pH stabilizing agents; chelating agents; denaturing agents; detergents; reducing agents; antioxidants; preservatives and stabilizing agents including protease inhibitors or nuclease inhibitors; proteases or nucleases; anti-microbials (e.g., antibiotics, anti-virals, anti-fungals and anti-parasitics); and low-water uptake saccharides (e.g., non-reducing sugars).

Buffers can maintain pH within a particular range, for example, between 1 and 12, and are also referred to as pH stabilizing agents. More typically, pH will range within about pH 5.0 to about pH 12.0. A particular example of a pH stabilizing agent is a zwitterion. Specific non-limiting examples of pH stabilizing agents include Tris (hydroxymethyl) aminomethane hydrochloride (TRIS), N-(2-hydroxyethyl)piperazine-N'-2-ethanesulfonic acid (HEPES), 3-(N-morpholino) propanesulfonic acid (MOPS), 2-(N-morpholino) ethanesulfonic acid (MES), N-tris [hydroxymethyl]methyl-2-aminoethanesulfonic acid (TES), N-[carboxymethyl]-2-aminoethanesulfonic acid (ACES), N-[2-acetamido]-2-iminodiacetic acid (ADA), N,N-bis[2-hydroxyethyl]-2-aminoethanesulfonic acid (BES), N-[2-hydroxyethyl]piperazine-N'-[2-hydroxypropoanesulfonic acid] (HEPPSO), N-tris[hydroxymethyl]methylglycine (TRICINE), N,N-bis[2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino) ethanesulfonic acid (CHES), N-(2-hydroxyethyl)piperazine-N'-(3-propanesulfonic acid) (EPPS), piperazine-N,N'-bis(2-ethanesulfonic acid (PIPES), [(2-hydroxy-1,1-bis[hydroxymethyl]ethyl) amino]-1-propanesulfonic acid (TAPS), N-tris (hydroxymethyl) methyl-4-aminobutane sulfonic acid (TABS), 2-amino-2-methyl-1-propanol (AMP), 3-[(1,1-dimethyl-2-hydroxyethyl)amino]-2-hydroxypropanesulfonic acid (AMPSO), ethanolamine and 3-amino-1-propanesulfonic acid. Additional specific non-limiting examples of pH stabilizing agents include potassium chloride, citric acid, potassium hydrogenphthalate, boric acid, potassium dihydrogenphosphate, Diethanolamine, sodium citrate, sodium dihydrogenphosphate, sodium acetate, sodium carbonate, sodium tetraborate, cacodylic acid, imidazole and 2-Amino-2-methyl-1-propanediol.

Substrates, biomolecules, elution and recovery liquids can include or exclude these or other buffers, such buffers further known in the art (see, for example, Sigma-Aldrich, St. Louis Mo.). Buffers can be used in combination with other buffers.

For elution or recovery of nucleic acid, with or without elution or recovery of peptide, a buffer that can maintain a pH in a range, for example, between a pH of about 10-12 (i.e., 9.8-12.2), or any numerical value or range within such ranges more particularly, a pH within a range of pH 10 to 12, pH 11 to 12, pH, 11.3 to 11.8, or pH 11.4 to 11.7, or any numerical value or range within such ranges, most particularly a pH of 11.4, 11.5, 11.6, 11.7, or 11.8, can be present in an elution or recovery liquid. Specific non-limiting examples of buffers that can maintain pH within such ranges include TABS, AMPSO, CHES, CAPSO, AMP, CAPS and CABS.

Buffers having alkylsulfonate moiety connected through a secondary amine linkage appear to be particularly useful for eluting or recovering nucleic acid. Without wishing to be limited to such particular buffers, it is possible that such buffers may fit into the DNA minor groove, which could contribute to destabilizing adsorbed DNA, in turn leading to elution of DNA from substrate. In addition, certain buffers, such as Tris and ethanolamine, perform well at pH values wherein the buffer is not charged. Thus, in order to elute or recover DNA, it does not appear to be necessary that the buffer is in a charged state. Based upon the foregoing, one of skill in the art can identify other buffers suitable for eluting or recovering nucleic acid.

Buffers or pH stabilizing agents are typically used in a range of about 0.1 mM to about 500 mM, in a range of about 0.5 mM to about 100 mM, in a range of about 0.5 mM to about 50 mM, in a range of about 1 mM to about 25 mM, or in a range of about 1 mM to about 10 mM. More particularly, buffers can have a concentration of about (i.e., within 10% of) 1 mM, 2 mM, 5 mM, 10 mM, 15 mM, 20 mM, 25 mM, 30 mM, 40 mM, or 50 mM. For elution or recovery of a biomolecule absorbed to a substrate, such ranges and buffer concentrations for elution and recovery liquids are appropriate.

Chelating agents typically form multiple bonds with metal ions, and are multidentate ligands that can sequester metals. Metal sequestration can in turn reduce or prevent microbial growth or degradation of biomolecules (e.g., peptide or nucleic acid), which in turn can improve preservation of biomolecules absorbed to a substrate. Specific non-limiting examples of chelating agents include EDTA (Ethylenediamine-tetraacetic acid), EGTA (Ethyleneglycol-O,O'-bis(2-aminoethyl)-N,N,N',N'-tetraacetic acid), GEDTA (Glycoletherdiaminetetraacetic acid), HEDTA (N-(2-Hydroxyethyl)ethylenediamine-N,N',N'-triacetic acid), NTA (Nitrilotriacetic acid), Salicylic acid, Triethanolamine and porphines. Typical concentrations of chelating agents are in a range of about 0.1 mM to about 100 mM, in a range of about 0.5 mM to about 50 mM, or in a range of about 1 mM to about 10 mM.

The term "chelating agent" also refers to chelating resins. Specific non-limiting examples of chelating resins include cross-linked polystyrene beads (e.g., CHELEX™), cross-linked agarose beads with tris(2-aminoethyl)amine, iminodiacetic acid, Duolite™ C-467, Duolite™ GT73. Chelating resins are typically used at a concentration in a range of about 0.01% (w/v) to about 1% (w/v), in a range of about 0.025% (w/v) to about 0.5% (w/v), or in a range of about 0.05% (w/v) to about 0.2% (w/v).

Denaturing agents and detergents typically form a chemical bridge between hydrophobic and hydrophilic environments, which in turn disrupts or diminishes the hydrophobic forces required to maintain native protein structure. Particular non-limiting chemical classes of denaturing agents and detergents include anionic surfactants, nonionic surfactants, cationic surfactants and ampholytic surfactants. Specific non-limiting examples of detergents include guanidinium thiocyanate, SDS, Sodium lauryl sulfate, NP40, triton X-100, Tween, Sodium cholate, Sodium deoxycholate, Benzethonium chloride, CTAB (Cetyltrimethylammonium bromide), Hexadecyltrimethylammonium bromide, and N,N-Dimethyldecylamine-N-oxide.

Reducing agents and antioxidants typically inhibit microbial growth and reduce biomolecule oxidation. Particular non-limiting classes of such agents include free radical scavenging agents. Specific non-limiting examples of reducing agents and anti-oxidants include DTT (dithiothreitol), dithioerythritol, urea, uric acid, 2-mercaptoethanol, dysteine, vitamin E, vitamin C, dithionite, thioglycolic acid and pyrosulfite.

Preservatives or stabilizing agents can be used if it is desired to inhibit or delay degradation of a biomolecule, either prior to or following absorption of a biomolecule a substrate, or after elution or recovery of a biomolecule from a substrate. Such preservatives and stabilizing agents can be used to improve the efficiency of elution or recovery of the native form of the biomolecule from substrate. Specific non-limiting examples of preservatives and stabilizing agents include sodium azide and polyethylene glycol (PEG). Typical concentrations of preservatives and stabilizing agents range from about 0.05% to about 1%.

Protease inhibitors inhibit peptide degradation. Particular non-limiting classes of protease inhibitors include reversible or irreversible inhibitors of substrate (e.g., peptide) binding to the protease. Particular non-limiting classes of protease inhibitors include serine and cysteine protease inhibitors. Specific non-limiting examples of protease inhibitors include PMSF, PMSF Plus, APMSF, antithrombin III, Amastatin, Antipain, aprotinin, Bestatin, Benzamidine, Chymostatin, calpain inhibitor I and II, E-64, 3,4-dichloroisocoumarin, DFP, Elastatinal, Leupeptin, Pepstatin, 1,10-Phenanthroline, Phosphoramidon, TIMP-2, TLCK, TPCK, trypsin inhibitor (soybean or chicken egg white), hirustasin, alpha-2-macroglobulin, 4-(2-aminoethyl)-benzenesulfonyl fluoride hydrochloride (AEBSF) and Kunitz-type protease inhibitors.

Nuclease inhibitors inhibit degradation of nucleic acid. Particular non-limiting classes of nuclease inhibitors include ribonuclease inhibitor (e.g., RNaseOUT™, Invitrogen Catalog #10777-019; RNase Block™, Stratagene Catalog #300151), diethyl pyrocarbonate and aurintricarboxylic acid (ATA).

Proteases, also referred to as proteinases, degrade peptides. Proteases can be specific or non-specific for their substrate (peptide). Specific non-limiting examples of proteases include, for example, collagenases such as collagenase A, B, D, H, and collagenase/Dispase; dispases such as dispase I and II; liberases such as liberase HI and RH; papain; pepsin; plasmin; plasminogen; pronase; proteinase K; trypsin; carboxypeptidases such as carboxypeptidase A, B, P and Y; chymotrypsin; elastase; endoproteinases such as endoproteinase Arg-C, Asp-N, Glu-C (V8 protease) and Lys-C; Factor Xa; gelatinase; subtilisin; thermolysin; thrombin; and cathepsin C.

Nucleases may specifically or non-specifically degrade nucleic acid either at the 5' or 3' end or internally. Nucleases may specifically or non-specifically degrade single or double strand sequences. Nucleases that specifically degrade nucleic acid include restriction enzymes, which digest nucleic acid having particular nucleotide sequences. Nucleases that non-specifically degrade nucleic acid include, for example, DNase I, exonuclease III, lambda-exonuclease, Bal 31 nuclease, mung bean nuclease, microccal nuclease, nuclease P1, Nuclease S1, nuclease S7 and uracil-DNA glycosylase. Nucleases specific for RNA (ribonucleases) include, for example, RNase, RNase A, RNase CL3, RNase H, RNase Phy M, RNase T1, RNase U2, RNase V1 and RNase I.

Anti-microbials inhibit growth or proliferation of microorganisms. Particular non-limiting classes of anti-microbials include anti-biotics, anti-virals, anti-fungals or anti-parasitic agents.

Specific non-limiting examples of anti-microbials include beta-lactams; semisynthetic penicillins; monobactams; carboxypenems; aminoglycosides; glycopeptides; glucan synthesis inhibitors; Lincomycins; macrolides; polypeptides; allylamines; azoles; polyenes; sulfonamides; pyrimidines; tetraenes; thiocarbamates; benzoic acid compounds, complexes and derivatives thereof; rifamycins; and tetracyclines. Additional specific non-limiting examples of anti-microbials include penicillin, cephalosporin, ampicillin, amoxycillin, aztreonam, clavulanic acid, imipenem, streptomycin, gentamycin, vancomycin, clindamycin, polymyxin, erythromycin, bacitracin, amphotericin, nystatin, rifampicin, tetracycline, chlortetracycline, doxycycline and chloramphenicol.

Specific non-limiting examples of anti-fungals include ammolfine, butenafine, naftifine, terbinafine, ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, undecylenate, silver sulfadiazine, undecylenic acid, undecylenic alkanolamide and Carbol-Fuchsin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir and ganciclovir.

Additional treatments or additives that also may be included or excluded with substrate, biomolecule, elution or recovery liquid, and so forth, are low-water uptake saccharides (sugars). Such saccharides include reducing and non-reducing sugars. Such saccharides can be either a mono- or a di-saccharide. Such saccharides can be either L- or D-forms. Specific non-limiting examples are trehalose and fucose. An additional non-limiting example is a malodextrin. Analogues and derivatives of saccharides also may be included or excluded. A specific non-limiting example of a trehalose analogue is 6-azido-6-deoxytrehalose. A specific non-limiting example of a trehalose derivative is trehalose-6-phosphate.

Low water uptake saccharides typically will have a relatively high glass transition temperature. As used herein, the term "glass transition temperature," when used in reference to a material such as a saccharides, means the temperature range where a crystalline material (e.g. a sugar) changes from a solid to a liquid. This transition occurs when the material is warmed, and reflects the softening and eventual conversion to a fluid. The transition therefore occurs over a temperature range. Specific non-limiting examples of relatively high glass transition temperatures are greater than about 60° C., greater than about 65° C., greater than about 70° C., or greater than about 75° C.

Low water uptake saccharides will typically have a relatively low hydroscopicity. The term "hydroscopicity" refers to the mass of moisture present in a given substance at a given temperature and relative humidity. Hydroscopicity values therefore reflect the sugars tendency to absorb or retain water. For low water uptake saccharides, hydroscopicity is typically less than about 15% (% weight gain at 25° C. at 94% estimated relative humidity), but can be less, for example, less than about 10%, less than about 5%, or less than about 1%.

Additional treatments or additives that may be included or excluded with substrate, biomolecule, elution or recovery liquid, and so forth, are polyhydric compounds. In various particular aspects, a substrate or biomolecule has not been treated with a polyhydric compound. In various additional particular aspects, a substrate or biomolecule is substantially free of a polyhydric compound. The term "substantially free," when used in reference to an excluded treatment or additive, such as a polyhydric compound, means that the biomolecule or substrate contains no more than 5% (e.g., 5%, 4%, 3%, 2%, 1% or less), of treatment or additive, such as a polyhydric compound relative to the total mass of the adsorbed substrate (w/w). In various particular aspects, a substrate or biomolecule has less than 0.50% or less than 0.25% of a polyhydric compound by total mass (w/w). Additional specific non-limiting examples of treatments and additives that may be included or excluded are alcohol (e.g., a vinyl alcohol or a polymer thereof), glycerol, sucrose, carrageenan, xanthum gum and pectin.

Materials that may be included or excluded with substrate, biomolecule, elution or recovery liquid, and so forth, are glass or glass fibers. In various particular aspects, a substrate or biomolecule is substantially free of glass or glass fibers. The term "substantially free," when used in reference to glass or glass fibers, means that the glass or glass fiber is no more than 5% (e.g., 5%, 4%, 3%, 2%, 1% or less), of the total mass of the adsorbed substrate (w/w).

The relative amounts of any included or excluded treatment or additive relative to each other or other substances or materials, such as biomolecules or substrate, can optionally be represented by their molar or mass ratio. For example, the relative amount of a peptide or a nucleic acid and any treatment or additive can be represented as a ratio, e.g., 1:0.0005, 1:0.005, 1:0.05, 1:0.5, 1:1, 1:10, 1:100, and so forth. In one aspect, peptide or nucleic acid can be in a molar ratio or mass ratio of about 1:0.5 to about 1:10 with a low-water uptake saccharide, such as trehalose.

The invention provides kits including invention compositions (e.g., "absorbed substrate units," which as set forth herein, include, inter alia, a biomolecule such as a peptide or nucleic acid absorbed to an elutable substrate which is elutable or recoverable, at least in part, from the substrate). In one embodiment, a kit includes an absorbed substrate unit, which includes a peptide and an elutable elastomeric substrate substantially free of moisture, wherein the peptide is absorbed to the elastomeric substrate, wherein the peptide resists degradation as compared to unabsorbed peptide, and wherein at least a portion of the peptide is recoverable or elutable from the elastomeric substrate, packaged into suitable packaging material. In another embodiment, a kit includes an absorbed substrate unit, which includes a nucleic acid absorbed to the substrate to which the peptide is absorbed. In a further embodiment, a kit includes an absorbed substrate unit, which includes a peptide, a nucleic acid and an elutable substrate substantially free of moisture, wherein the peptide and the nucleic acid is absorbed to the substrate, wherein the peptide or the nucleic acid resists degradation as compared to unabsorbed peptide or nucleic acid, and wherein at least a portion of the peptide or the nucleic acid is recoverable or elutable from the substrate.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention. Kits of the invention therefore can additionally include labels or instructions for using one or more of the kit components in a method of the invention. Instructions can include instructions for practicing any of the methods of the invention described herein. The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical disk such as CD- or DVD-ROM/RAM, DVD, MP3, magnetic tape, or an electrical storage media such as RAM and ROM and hybrids of these such as magnetic/optical storage media.

Kits further include a plurality (two or more) of absorbed substrate units. In one aspect, each absorbed substrate unit includes a peptide and an elutable elastomeric substrate substantially free of moisture, wherein the peptide is absorbed to the elastomeric substrate, wherein the peptide resists degradation as compared to unabsorbed peptide, and wherein at least a portion of the peptide is recoverable or elutable from the elutable elastomeric substrate. In another aspect, each absorbed substrate unit includes a peptide, a nucleic acid and an elutable substrate substantially free of moisture, wherein the peptide and the nucleic acid is absorbed to the substrate, wherein the peptide or the nucleic acid resists degradation as compared to unabsorbed peptide or nucleic acid, and wherein at least a portion of the peptide or the nucleic acid is recoverable or elutable from the elutable substrate.

An additional example of an invention kit includes a package having one or more compartments and an elutable elastomeric substrate, each compartment having a physical size sufficient for holding the elutable elastomeric substrate, wherein the elutable elastomeric substrate comprises a material suitable for absorbing a biomolecule (e.g., peptide or nucleic acid) and for elution or recovery of the absorbed biomolecule from the elutable elastomeric substrate; and, instructions for absorbing a biomolecule (e.g., peptide or nucleic acid) to the elutable elastomeric substrate. Accordingly, invention kits include elutable elastomeric substrate suitable for absorbing a biomolecule (e.g., peptide or nucleic acid) in which a biomolecule (e.g., peptide or nucleic acid) has not yet been absorbed to the elutable elastomeric substrate present in the kit.

Kits of the invention may contain an elution or recovery liquid, an optional wash solution, and one or more other additional components useful for elution or recovery of biomolecules. Kits of the invention may contain an elution or recovery liquid, an optional wash solution, and one or more other additional components useful for analysis of the eluted or recovered nucleic acid. A kit may further include one or more reagents useful for amplifying a nucleic acid of interest, including but not limited to, one or more amplification primers, one or more dioxy nucleotide triphosphates (e.g., a mixture of dATP, dGTP, dCTP and/or dUTP or dTTP) one or more polymerizing enzymes (e.g., DNA polymerase), etc. A kit may include one or more additional reagents useful for sequencing a nucleic acid of interest, for example, one or more sequencing primers (labeled or unlabeled, or covalently modified), one or more deoxynucleotide triphosphates (e.g., a mixture of dATP, dGTP, dCTP and dUTP or dTTP), one or more labeled or unlabeled dideoxynucleotide triphosphate terminators (e.g., ddATP, ddGTP, ddCTP and ddUTP or ddTTP) or one or more polymerizing enzymes (e.g., DNA polymerase, Taq polymerase, Pfu, elongase). A kit may include one or more reagents useful for labeling an isolated nucleic acid, e.g., one or more labeled deoxynucleotide triphosphates, one or more polymerizing enzymes, or one or more labeled or unlabeled primers.

Individual absorbed substrate units can be included within a storage unit. A storage unit is a structure (container or housing) that can be used to house or store one or more (e.g., a plurality) substrate units. Thus, a storage unit can contain single or multiple compartments for elutable substrates or absorbed substrate units. In one embodiment, the storage unit includes one or more absorbed substrate units in which peptide is absorbed to an elutable elastomeric substrate, which is substantially free of moisture, wherein the peptide resists degradation as compared to unabsorbed peptide, and wherein at least a portion of the peptide is recoverable or elutable from the elutable elastomeric substrate. In another embodiment, a storage unit includes one or more absorbed substrate units in which a nucleic acid is absorbed to an elutable elastomeric substrate, which is substantially free of moisture, wherein the nucleic acid resists degradation as compared to unabsorbed nucleic acid, and wherein at least a portion of the nucleic acid is recoverable or elutable from the elastomeric substrate. In yet another embodiment, a storage unit includes one or more absorbed substrate units in which a peptide and a nucleic acid are absorbed to an elutable substrate, which is substantially free of moisture, wherein the peptide or the nucleic acid resists degradation as compared to unabsorbed peptide or nucleic acid, and wherein at least a portion of the peptide or the nucleic acid is recoverable or elutable from the substrate. In particular aspects, a storage unit includes two or more absorbed substrate units (e.g., 3, 4, 5-10, 10-25, 25-50, 50-100, 100-500, 500-1000, 1000-5000, 5000-10,000, or any numerical value or range within such ranges), each of which have a different peptide or a different nucleic acid. In additional particular aspects, a storage unit includes two or more absorbed substrate units (e.g., 3, 4, 5-10, 10-25, 25-50, 50-100, 100-500, 500-1000, 1000-5000, 5000-10,000, or any numerical value or range within such ranges), each of which have a different biological sample.

Elutable substrates can be included with a storage unit. In one embodiment, a storage unit has a plurality of compartments each having a physical size sufficient for housing an elutable elastomeric substrate and one or more elutable elastomeric substrates, in which the elutable elastomeric substrate is suitable for absorbing a biomolecule. Typically, the elutable elastomeric substrate is a material suitable for storing or preserving a biomolecule (e.g., peptide or nucleic acid) and for elution or recovery of the biomolecule from the elutable elastomeric substrate. Such storage units can also include instructions for absorbing a biomolecule (peptide or nucleic acid) to the elutable elastomeric substrate, instructions for elution or recovery of the absorbed biomolecule from the elutable elastomeric substrate, or instructions for preparing an aqueous liquid for eluting or recovering the absorbed biomolecule from the elutable elastomeric substrate. Accordingly, invention storage units include units housing elutable elastomeric substrate suitable for absorbing a biomolecule (e.g., peptide or nucleic acid), in which a biomolecule (e.g., peptide or nucleic acid) has not yet been absorbed to the elutable elastomeric substrate present in the unit.

A kit or storage unit typically includes a label or packaging insert including a description of the components or instructions for use. Exemplary instructions include, instructions for eluting or recovering at least a portion of one or more biomolecules such as peptide or nucleic acid alone or in combination, either preferentially, sequentially or simultaneously; instructions for eluting or recovering at least a portion of a peptide alone or in combination with at least a portion of the nucleic acid, either preferentially, sequentially or simultaneously; or instructions for absorbing a biomolecule, such as peptide or nucleic acid or sample thereof, to an elutable substrate.

Additional optionally included or excluded components of invention kits and storage units include, for example, a liquid suitable for elution or recovery of a biomolecule absorbed to a substrate. In one aspect, the liquid is aqueous, and is suitable for elution or recovery of a peptide or a nucleic acid from an elutable substrate. In additional aspects, kits and storage units include liquid suitable for elution or for recovery preferentially, sequentially or simultaneously a biomolecule (e.g., peptide or nucleic acid) from an elutable substrate, or at least a portion of a biomolecule (e.g., peptide or nucleic acid) from an elutable substrate. In yet additional aspects, kits and storage units include instructions for preparing an aqueous liquid for eluting or recovering a biomolecule (e.g., peptide or nucleic acid) from one or more of the plurality of elutable elastomeric substrates.

A kit or storage unit can contain additional components, for example, a device (vessel or holder) having a physical size sufficient for holding an elutable substrate, and optionally suitable for eluting or recovering at least a portion of the peptide from an absorbed substrate unit, at least a portion of the nucleic acid, or at least a portion of the peptide in combination with at least a portion of the nucleic acid from the substrate unit. In one aspect, the device (vessel or holder) has a physical size sufficient for introducing or holding an elutable elastomeric substrate, the device having an open end, an openable end or a removable end, and wherein the device (vessel or holder) has physical dimensions suitable for inserting a plunger therein so as to cause compression of the elutable elastomeric substrate. In one particular aspect, the device (vessel or holder) is substantially represented by the illustration in FIGS. 2 and 3. In another particular aspect, the device (vessel or holder) has a physical size sufficient for introducing or holding an elutable substrate, in a physical configuration, such as a tube or spin column, suitable for insertion into a centrifuge tube. A plurality of such devices each having a physical size sufficient for introducing or holding one or more substrate units can also be included in a kit. A plurality of such devices (vessels or holders) is amenable to automated handling of multiple substrate units for elution or recovery of biomolecules from each substrate unit.

Kits may further include tools for manipulating elements for biomolecule elution or recovery, vessels or holders for collecting eluted or recovered biomolecules, materials for purifying biomolecules. For example, columns or cartridges for peptide or nucleic acid purification from a solution, affinity media such as beads for peptide or nucleic acid purification from a solution, or chromatographic media for purification or separation of peptide or nucleic acid can be included in a kit. Materials for subsequent purification of eluted nucleic acids include, but are not limited to, magnetic beads for nucleic acid purification, and nucleic acid purification columns.

Individual storage units (containers or housings) can comprise any physical configuration suitable for housing one or more elutable substrates, including an absorbed substrate unit as set forth herein, having a stored or preserved biomolecule. Each of the absorbed substrate units can have a defined location, position or address within the storage unit. In one embodiment, a storage unit comprises a multi-well plate. In particular aspects, a multi-well plate comprises 2-6, 6-12, 12 to 24, 24-96, or more compartments. In additional particular aspects, one or more of the wells of the multi-well plate has a volume of about 10-50 µl, 50-100 µl, 100-250 µl, 250-500 µl, 0.5-1.0 ml, 1.0-2.0 ml, 2.0-3.0 ml, 3.0-5.0 ml, or 5.0-10.0 ml, more particularly, 50 µl, 100 µl, 200 µl, 250 µl, 500 µl, or any numerical value or range within such ranges.

Storage units also refer to a plurality of two or more individual storage units. Thus, as used herein a storage unit also refers to a plurality of individual apparatus or container for housing one or more elutable substrates. For example, a storage unit can include two or more multi-well plates, two or more devices as represented by the illustration in FIGS. 2 and 3, two or more tubes or spin columns, etc. In one embodiment, a storage unit houses a plurality of stored or preserved peptides, each peptide individually adsorbed to an elutable elastomeric substrate substantially free of moisture, wherein at least a portion of said peptide is recoverable or elutable from said elutable elastomeric substrate.

A storage apparatus can be used to house or store adsorbed substrate units, elutable elastomeric substrates suitable for adsorbing a biomolecule, kits or storage units. In one embodiment, a storage apparatus is capable of maintaining the absorbed substrate unit, elutable elastomeric substrate suitable for adsorbing a biomolecule, kit or storage unit at a temperature at about −20° C., at about 4° C., at 4-10° C., at 10-20° C., at 20-30° C., at 30-40° C., at 40-50° C., at 50-60° C., at 60-70° C., or at 70-80° C.

The invention provides libraries. The term "library" as used herein refers to a collection of two or more compositions, such as absorbed substrate units, elutable substrates, storage units, etc. Libraries can include a collection of biomolecules, such as peptides or nucleic acids; a collection of samples, such as biological samples; a collection of absorbed substrate units; or combinations thereof. The absorbed substrate units of the library can comprise any stored or preserved biomolecule or biological sample in which an absorbed biomolecule is elutable or recoverable from the substrate (e.g., an elutable elastomeric substrate). In one particular embodiment, a library includes at least two elutable substrates, each of which have a different peptide or a different nucleic acid absorbed to the substrate. In another particular embodiment, a library includes at least two elutable substrates, each of which have one or more different biological samples absorbed to the substrate.

The library can be any size. In various embodiments, a 10-50, 50-100, 100-500, 500-2500, 2500-10,000, 10,000-50,000, 50,000-250,000 different biomolecules (e.g., peptides or nucleic acids), each of which is absorbed to an elutable substrate.

Libraries can be in an array, in which the array has positioned thereon, typically in a discrete region, a biomolecule, a biological sample or an absorbed substrate unit. The position of one or more biomolecules, biological samples or adsorbed substrate units of the array may be known (i.e., have a defined position, a unique location or an address) so that the particular sample at the position can be retrieved or analyzed. In addition, since the position of each sample in the array is known, the identities of the samples can be determined. Arrays typically comprise two- or three-dimensional surfaces or supports. An array of absorbed substrate units each unit placed in a vessel positioned on the array can be used in a manual or automated system for storage, retrieval, elution or recovery of a biomolecule adsorbed thereon, and a subsequent analysis or application.

An array can have any density appropriate for the application. The density is determined, at least in part, by the total number of samples (e.g., absorbed substrate unit) on the surface or support. Minimal array densities will be determined, at least in part, by the size of the sample. For example, an absorbed substrate unit having a size of 1 cm.sup.3 will require at least this volume in order to have a discrete position on the array.

A "microarray" typically has a high density of discrete regions on a two-dimensional solid or semi-sold surface or support, in which the discrete regions are in the micron size range. Typical densities for a microarray are at least 25-50/$cm^2$, more typically at least 50-100/$cm^2$, even more typically at least about 100-500 $cm^2$. Most typically, density is at least about 1,000/$cm^2$.

The invention provides methods of producing a stabilized or preserved biomolecule (e.g., peptide or nucleic acid). The stabilized or preserved biomolecule (e.g., peptide or nucleic acid) is absorbed to a substrate in an elutable or recoverable form.

In one embodiment, a method includes providing an elutable elastomeric substrate, wherein the elutable elastomeric substrate allows elution of an amino acid sequence adsorbed thereto; contacting the elutable elastomeric substrate with a peptide under conditions allowing absorption of the peptide to the substrate; and optionally reducing moisture from the contacted elutable elastomeric substrate to less than about 5%, 5-10%, 10-15%, 15-20%, or 20-25% moisture by mass, thereby producing a stabilized or preserved peptide. In another embodiment, a method includes providing an elutable porous or semi-porous elastomeric substrate, wherein the substrate allows elution of an amino acid sequence absorbed thereto; contacting the elutable porous or semi-porous elastomeric substrate with a peptide under conditions allowing absorption of the peptide to the substrate; and optionally reducing moisture from the contacted substrate to less than about 5%, 5-10%, 10-15%, 15-20%, or 20-25% by mass. The absorbed peptide is typically stabilized or preserved in an elutable or recoverable form, or the absorbed peptide is stored in an elutable or recoverable form, without any requirement for preserving the peptide. In particular aspects, the substrate has not been treated with an alcohol, glycerol, sucrose, carrageenan, xanthum gum or pectin.

The invention also provides methods of storing a biomolecule (e.g., peptide or nucleic acid) in an elutable or recoverable form. In one embodiment, a method includes providing an elutable elastomeric substrate, wherein the elutable elastomeric substrate allows elution of an amino acid sequence absorbed thereto; contacting the elutable elastomeric substrate with a peptide under conditions allowing absorption of the peptide to the substrate; and optionally reducing moisture from the contacted elutable elastomeric substrate to less than about 5%, 5-10%, 10-15%, 15-20%, or 20-25% by mass, thereby producing a stored peptide in an elutable or recoverable form. In another embodiment, a method includes providing an elutable porous or semi-porous elastomeric substrate, wherein the substrate allows elution of an amino acid sequence absorbed thereto; contacting the elutable porous or semi-porous elastomeric substrate with a peptide under conditions allowing absorption of the peptide to the substrate; and optionally reducing moisture from the contacted substrate to less than about 5%, 5-10%, 10-15%, 15-20%, or 20-25% by mass, thereby producing a stored peptide in an elutable or recoverable form. The absorbed peptide stored in an elutable or recoverable form can but need not be stabilized or preserved. In particular aspects, the substrate has not been treated with an alcohol, glycerol, sucrose, carrageenan, xanthum gum or pectin.

In yet further embodiments, an elutable substrate (e.g., an elastomeric substrate) having absorbed thereto a first biomolecule (e.g., a peptide) is contacted with a second biomolecule (e.g., nucleic acid) either prior to, simultaneously with or following absorption of the first biomolecule, under conditions allowing absorption of the second biomolecule (e.g., nucleic acid) to the substrate. The absorbed first or second biomolecule (e.g., peptide or nucleic acid) is in a stabilized or preserved form that is in an elutable or recoverable form, or the absorbed first or second biomolecule (e.g., peptide or nucleic acid) is stored in an elutable or recoverable form but neither the first nor second biomolecule need be stabilized or preserved. In various aspects, the elutable substrate is porous or semi-porous.

The invention additionally provides methods of eluting and methods for recovering a biomolecule (e.g., peptide or nucleic acid) absorbed to an elutable elastomeric substrate. In one embodiment, a method includes providing a peptide absorbed to an elutable elastomeric substrate, the substrate substantially free of moisture; hydrating the elutable elastomeric substrate with a liquid under conditions that elute at least a portion of the peptide from the substrate; and agitating, incubating or compressing the hydrated elutable elastomeric substrate to elute at least a portion of the peptide from the substrate, thereby eluting a peptide absorbed to the elutable elastomeric substrate. In another embodiment, a method includes providing a peptide absorbed to an elutable elastomeric substrate, the substrate substantially free of moisture; hydrating the elutable elastomeric substrate with a liquid under conditions that elute at least a portion of the peptide from the substrate; agitating, incubating or compressing the elutable elastomeric substrate to elute at least a portion of the peptide from the substrate; and collecting the eluate, thereby recovering the peptide absorbed to an elutable elastomeric substrate. In additional embodiments, an elutable elastomeric substrate has a second biomolecule, third or subsequent (e.g., a nucleic acid) absorbed thereto. In particular aspects, at least a portion of the second, third or subsequent biomolecule absorbed to the elutable elastomeric substrate is eluted or recovered from the substrate. The second, third or subsequent biomolecule can be eluted or recovered with or without, prior to, simultaneously with or following elution or recovery of a first biomolecule. In further aspects, the elutable elastomeric substrate is porous or semi-porous.

A first, second or a subsequent biomolecule absorbed to elutable elastomeric substrate can be contacted with an aqueous liquid under conditions to elute at least a portion of the nucleic acid from the substrate. For example, the absorbed elutable elastomeric substrate can optionally be agitated, incubated or compressed in the presence of the aqueous liquid to elute or recover at least a portion of the first, second or a subsequent biomolecule (e.g., a peptide or nucleic acid) from the substrate, thereby eluting or recovering the first, second or a subsequent biomolecule from the elutable elastomeric substrate.

An optional substrate wash, prior to applying recovery/elution liquid (e.g., peptide or nucleic acid elution liquid) to substrate, may include contacting substrate with a wash buffer prior to contacting the substrate with elution liquid. A wash step can be performed in order to remove unwanted cellular debris, or other contaminants. A wash step can also be used to remove components of previously used reagents, such as detergents or chelating agents. Wash steps also serve to wet the substrate and the biomolecule absorbed thereto prior to elution or recovery, although sufficient hydration is accomplished by the elution or recovery liquid alone.

As used herein, "wash" refers to an aqueous or non-aqueous liquid, more typically an aqueous, detergent, solvent, or enzymatic wash solution. A "wash solution" or "wash buffer" may include aqueous or non-aqueous solvents, or a combination of such solvents. Non-aqueous solvents include, but are not limited to, ethanol, acetone, phenol, chloroform, acetonitrile, dimethylsulfoxide, or any polar or nonpolar non-aqueous solvent suitable for use in accordance with the invention. A wash solution may contain one or more additional components including, but not limited to, a buffer, salt, detergent (e.g., Triton, Tween, SDS, CHAPS, etc.), protein, preservative, or stabilizer. Wash solutions may contain one or more different proteins, e.g., enzymes to carry out certain reactions, or proteins for blocking or buffering the solution. Wash solutions may contain enzymes including, but not limited to, protease, nuclease, kinase, or methylase, and may contain lysis buffer or digestion buffer. Wash solutions may contain bovine serum albumin (BSA), casein (or milk), or denatured proteins for blocking or buffering. Wash buffers can be removed by means including, but not limited to, centrifugation, aspiration, or absorption.

One of skill in the art can determine the particular composition of a wash solution suitable for the application, and whether one or more wash steps are suitable for a particular embodiment. For example, an exemplary wash buffer includes 10 mM Tris and 0.1 mM EDTA at a pH of about 8.0, which may optionally include a detergent, such as Triton X-100 or Tween 20, for example at 1%. Such a wash is appropriate to wash a substrate absorbed with nucleic acid. However, should peptide be absorbed to the substrate, such a buffer will likely elute the absorbed peptide. Thus, such a wash buffer can elute peptide absorbed to substrate. In a particular embodiment, a wash buffer includes a pH buffering agent, optionally a chelating agent and optionally a detergent.

The invention provides methods of producing libraries, including libraries of stored or preserved biomolecules (e.g., peptide or nucleic acid). In one embodiment, a library includes a plurality of stored peptides, and a method includes contacting an elutable elastomeric substrate with a first peptide under conditions allowing absorption of the first peptide to the substrate; optionally reducing moisture from the contacted substrate to less than about 5%, 5-10%, 10-15%, 15-20%, or 20-25% by mass, thereby producing a stored first peptide; and repeating steps a) and b) at least one time with a second or subsequent peptide absorbed to a different elutable elastomeric substrate, thereby producing a library including a plurality of stored peptides. In another embodiment, at least a portion of the first or second peptide is recoverable from said elutable elastomeric substrate. In yet another embodiment, the first or second peptide resists degradation following absorption to the substrate, as compared to the first or second peptide not absorbed to the substrate. In particular aspects, the elutable elastomeric substrate is porous or semiporous.

Biomolecules and other samples for storing in an elutable or recoverable form, for stabilizing or preserving in an elutable or recoverable form, for eluting or recovering from an elutable substrate, or for a library, are as set forth herein. Exemplary biomolecules include, for example, peptides and nucleic acids. Exemplary biomolecules also include, for example, a biological sample (e.g., whole blood, serum, plasma, biopsied cells or tissue, sputum, mucus, cerebrospinal fluid, urine, stool, semen, etc.). Liquid samples can contain biomolecules dissolved or suspended therein. Exemplary biomolecules further include, for example, cells, bacteria, virus, yeast, or mycoplasma.

As further as set forth herein biological samples, liquid or solid, can be obtained from a subject, including mammals (e.g., humans). Candidate subjects include subjects in which it is desired to screen for a genetic disease or physiological disorder, or a predisposition towards a genetic disease or physiological disorder. Candidate subjects also include subjects having or at risk of having a disease or physiological disorder (e.g., a genetic disorder, a hyperproliferative disorder, an immunological disorder or a microbial infection).

Candidate subjects further include subjects that have been incarcerated or are at risk of incarceration. An example of subject at risk of incarceration is subject on parole or a subject previously incarcerated, who is at high risk of recidivism.

The invention compositions (absorbed substrate units, kits, storage units, housings, libraries and methods (e.g., producing absorbed substrate units, producing stored or stabilized peptide or nucleic acid, eluting or recovering stored or stabilized peptide or nucleic acid, as set forth herein) are suitable for use as part of automated system or high throughput processes. As used herein, an "automated system" includes "automatic elution or recovery systems" including hand-held and robotic elution or recovery systems.

Typically, automatic elution or recovery systems are devices that dispense and remove liquids to and from individual wells of multi-well reaction plates. Hand-held automatic elution or recovery systems comprise a single plunger handle with multiple fluid aspirating and dispensing ends to simultaneously aspirate and dispense liquid of a liquid reaction system from single or multiple liquid reaction vessels simultaneously. Robotic automatic systems are computer operated rather than hand-held and include such products as, for example, BIOMEK 2000 (Beckman Instruments, Fullerton, Calif.), Zymark Benchmate (Zymark, Hopkinton, Mass.), ROSYS PLATO (Rapperswil, Switzerland) and others.

The invention compositions and methods are suitable for use as part of an automated archive and analysis system. Exemplary applicable systems include, for example, the systems described in U.S. Patent Application Publication Ser. Nos. 200300886571; 20030129755; 20030087425; 20030215369; 20030087455; 20030129755; and 20040101966.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a biomolecule" includes a plurality of biomolecules such as two or more peptides, two or more nucleic acids, a peptide and a nucleic acid, a biological sample, etc.

The invention is generally disclosed herein using affirmative language to describe the numerous embodiments. However, the invention specifically includes embodiments in which particular subject matter is excluded, in full or in part, such as substances or materials, method steps and conditions, protocols, procedures, assays or analysis disclosed herein. Thus, even though the invention is generally not expressed herein in terms of what the invention does not include, aspects that are not expressly included in the invention are nevertheless expressly or inherently disclosed herein. As an example, the invention includes affirmatively described embodiments in which specific subject matter disclosed herein is excluded from the affirmatively described embodiments. Furthermore, the invention includes embodiments which exclude subject matter, expressly or inherently disclosed herein or known in the art that, in view of the subject matter and relevant technology, would be incompatible with one or more embodiments of the invention.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This Example describes studies indicating that peptide absorbed to substrate with trehalose alone, and in combination with other materials, increases peptide stability at room temperature as well as at higher temperatures.

Table 1A shows ferritin stability, as assessed by a standard ferritin immunoassay, over an 84 day period with plasma proteins stored on a variety of substrates and with a variety of additives. Polyester and cellulose (S&S 903™) paper substrates when untreated or treated with trehalose, and dithiothreitol showed significant stability for ferritin over the 84 day storage period.

TABLE 1A

Ferritin Stability Study

| Well # | Solid support | n = 47 | n = 49 | n = 52 | n = 57 | n = 63 | n = 70 | n = 88 | n = 31 | n = 119 |
|---|---|---|---|---|---|---|---|---|---|---|
| | | | | | Biorad Immuno Plus Level 3 Control | | | | | |
| | | control: | control: | control: | control: | control: | control: | control: | control: | control: |
| | | | | | Human Pooled plasma | | | | | |
| | | 444.02 | 445.49 | 447.21 | 444.02 | 444.02 | 444.02 | 449.7 | 450.52 | 448.17 |
| | | | | | Day: | | | | | |
| | | 1 av | 3 av | 7 av | 14 av | 21 av | 28 av | 43 av | 56 av | 84 av |
| C1, D1 | treated polyester, no additive | 521 | 438 | 426 | 426 | 458 | 488 | 319 | 504 | 623 |
| C2, D2 | treated polyester, 0.01 mg/ml DTT | 632 | 482 | 483 | 414 | 465 | 485 | 477 | 512 | 597 |
| C3, D3 | treated polyester, 2 mM uric acid | 724 | 502 | 501 | 511 | 504 | 461 | 491 | 485 | 513 |
| C4, D4 | treated polyester, 1% Vitamin E | 680 | 485 | 463 | 468 | 436 | 497 | 436 | 485 | 494 |
| C5, D5 | treated polyester, 2% Vitamin E | 578 | 413 | 421 | 461 | 443 | 466 | 437 | 381 | 404 |
| C6, D6 | treated polyester, 160 mg/ml Fucose | 648 | 457 | 440 | 397 | 347 | 287 | 285 | 291 | 260 |
| C7, D7 | treated polyester, 320 mg/ml Fucose | 536 | 431 | 421 | 471 | 345 | 359 | 280 | 287 | 274 |
| C8, D8 | treated polyester, 160 mg/ml Trehalose | 445 | 516 | 527 | 597 | 525 | 529 | 507 | 539 | 613 |
| C9, D9 | treated polyester, 320 mg/ml Trehalose | 667 | 529 | 558 | 587 | 504 | 562 | 522 | 532 | 515 |
| C10, D10 | treated polyester, 0.1 mM cysine | 682 | 485 | 480 | 556 | 426 | 527 | 501 | 514 | 583 |
| C11, D11 | treated polyester, 1 mM cystine | 667 | 504 | 519 | 566 | 529 | 542 | 508 | 505 | 577 |
| C12, D12 | treated polyester, no additive | 783 | 502 | 495 | 521 | 541 | 516 | 454 | 487 | 561 |
| E1, F1 | untreated S&S 903 ™, no additive | 575 | 483 | 511 | 573 | 377 | 413 | 389 | 428 | 511 |
| E2, F2 | untreated S&S 903 ™, 0.01 mg/ml DTT | 578 | 511 | 437 | 636 | 393 | 421 | 387 | 437 | 526 |
| E3, F3 | untreated S&S 903 ™, 2 mM uric acid | 544 | 508 | 574 | 574 | 344 | 406 | 385 | 428 | 562 |
| E4, F4 | untreated S&S 903 ™, 1% Vitamin E | 555 | 527 | 504 | 654 | 449 | 361 | 382 | 432 | 534 |
| E5, F5 | untreated S&S 903 ™, 2% Vitamin E | 559 | 458 | 704 | 616 | 457 | 420 | 380 | 420 | 517 |
| E6, F6 | untreated S&S 903 ™, 160 mg/ml Fucose | 517 | 507 | 550 | 412 | 363 | 303 | 185 | 76 | 28 |
| E7, F7 | untreated S&S 903 ™, 320 mg/ml Fucose | 543 | 451 | 617 | 523 | 397 | 334 | 246 | 230 | 159 |
| E8, F8 | untreated S&S 903 ™, 160 mg/ml Trehalose | 559 | 529 | 632 | 622 | 515 | 457 | 406 | 507 | 601 |
| E9, F9 | untreated S&S 903 ™, 320 mg/ml Trehalose | 545 | 547 | 608 | 642 | 508 | 437 | 425 | 474 | 615 |
| E10, F10 | untreated S&S 903 ™, 0.1 mM cystine | 549 | 407 | 581 | 624 | 480 | 424 | 388 | 393 | 514 |
| E11, F11 | untreated S&S 903 ™, 1 mM cystine | 586 | 528 | 608 | 665 | 459 | 416 | 410 | 415 | 548 |
| E12, F12 | untreated S&S 903TM | 575 | 523 | 553 | 619 | 497 | 400 | 371 | 403 | 481 |
| G1 | untreated polyester, no additive | 670 | 413 | 511 | 475 | 440 | 473 | 555 | 646 | 779 |
| G2 | untreated polyester, 0.01 mg/ml DTT | 690 | 484 | 864 | 460 | 448 | 475 | 591 | 615 | 824 |
| G3 | untreated polyester, 2 mM uric acid | 559 | 215 | 837 | 235 | 433 | 468 | 582 | 606 | 111 |
| G4 | untreated polyester, 1% Vitamin E | 637 | 349 | 970 | 391 | 448 | 477 | 544 | 597 | 726 |
| G5 | untreated polyester, 2% Vitamin E | 511 | 468 | 797 | 486 | 497 | 457 | 266 | 109 | 42 |
| G6 | untreated polyester, 160 mg/ml Fucose | 690 | 468 | 901 | 446 | 304 | 67 | 357 | 337 | 222 |
| G7 | untreated polyester, 320 mg/ml Fucose | 604 | 402 | 899 | 82 | 406 | 346 | 597 | 759 | 846 |
| G8 | untreated polyester, 160 mg/ml Trehalose | 728 | 457 | 440 | 535 | 548 | 444 | 473 | 440 | 515 |

TABLE 1A-continued

Ferritin Stability Study

| | | n = 47 | n = 49 | n = 52 | n = 57 | n = 63 | n = 70 | n = 88 | n = 31 | n = 119 |
|---|---|---|---|---|---|---|---|---|---|---|
| | | | | | Biorad Immuno Plus Level 3 Control | | | | | |
| | | control: | control: | control: | control: | control: | control: | control: | control: | control: |
| | | | | | Human Pooled plasma | | | | | |
| | | 444.02 | 445.49 | 447.21 | 444.02 | 444.02 | 444.02 | 449.7 | 450.52 | 448.17 |
| | | | | | Day: | | | | | |
| Well # | Solid support | 1 av | 3 av | 7 av | 14 av | 21 av | 28 av | 43 av | 56 av | 84 av |
| G9 | untreated polyester, 320 mg/ml Trehalose | 584 | 351 | 464 | 502 | 533 | 504 | 493 | 491 | 515 |
| G10 | untreated polyester, 0.1 mM cysine | 633 | 306 | 482 | 353 | 482 | 504 | 195 | 464 | 575 |
| G11 | untreated polyester, 1 mM cystine | 630 | 473 | 486 | 506 | 442 | 515 | 448 | 493 | 637 |
| G12 | untreated polyester, no additive | 619 | 147 | 413 | 519 | 453 | 517 | 151 | 471 | 457 |
| H1 | treated S&S 903 ™, no additive | 537 | 456 | 377 | 379 | 300 | 294 | 294 | 288 | 370 |
| H2 | treated S&S 903 ™, 0.01 mg/ml DTT | 488 | 437 | 585 | 345 | 373 | 253 | 220 | 214 | 253 |
| H3 | treated S&S 903 ™, 2 mM uric acid | 502 | 376 | 661 | 439 | 373 | 299 | 271 | 243 | 245 |
| H4 | treated S&S 903 ™, 1% Vitamin E | 537 | 419 | 548 | 519 | 382 | 293 | 246 | 179 | 146 |
| H5 | treated S&S 903 ™, 2% Vitamin E | 519 | 397 | 559 | 496 | 417 | 263 | 256 | 296 | 203 |
| H6 | treated S&S 903 ™, 160 mg/ml Fucose | 445 | 450 | 354 | 371 | 165 | 148 | 71 | 65 | 43 |
| H7 | treated S&S 903 ™, 320 mg/ml Fucose | 407 | 427 | 373 | 436 | 316 | 226 | 189 | 240 | 217 |
| H8 | treated S&S 903 ™, 160 mg/ml Trehalose | 470 | 479 | 601 | 614 | 508 | 419 | 434 | 460 | 528 |
| H9 | treated S&S 903 ™, 320 mg/ml Trehalose | 568 | 490 | 642 | 598 | 517 | 456 | 447 | 491 | 604 |
| H10 | treated S&S 903 ™, 0.1 mM cystine | 631 | 353 | 618 | 576 | 448 | 379 | 322 | 339 | 260 |
| H11 | treated S&S 903 ™, 1 mM cystine | 519 | 411 | 602 | 576 | 451 | 374 | 339 | 374 | 348 |
| H12 | treated S&S 903 ™, no additive | 521 | 371 | 627 | 508 | 433 | 313 | 300 | 237 | 257 |

TABLE 1B

| Well # | Solid support | Day 1 av | Day 3 av | Day 7 av | Day 14 av |
|---|---|---|---|---|---|
| A1, B1 | IsoCode ™, no additive | 34 | 23 | 33 | 38 |
| A2, B2 | IsoCode ™, 0.01 mg/ml DTT | 38 | 21 | 25 | 36 |
| A3, B3 | IsoCode ™, 2 mM uric acid | 32 | 28 | 26 | 27 |
| A4, B4 | IsoCode ™, 1% Vitamin E | 30 | 28 | 32 | 34 |
| A5, B5 | IsoCode ™, 2% Vitamin E | 25 | 21 | 31 | 32 |
| A6, B6 | IsoCode ™, 160 mg/ml fucose | 28 | 21 | 24 | 22 |
| A7, B7 | IsoCode ™, 320 mg/ml fucose | 32 | 25 | 23 | 21 |
| A8, B8 | IsoCode ™, 160 mg/ml trehalose | 31 | 25 | 27 | 31 |
| A9, B9 | IsoCode ™, 320 mg/ml trehalose | 28 | 20 | 27 | 22 |
| A10, B10 | IsoCode ™, 0.1 mM cystine | 36 | 22 | 28 | 28 |
| A11, B11 | IsoCode ™, 1 mM cystine | 35 | 25 | 35 | 32 |
| A12, B12 | IsoCode ™, no additive | 28 | 25 | 28 | 28 |

TABLE 1C

| ***** | Change in Rows A and B | Day 5 av | Day 12 av | Day 27 av | Day 40 av | Day 68 av | Day 99 av |
|---|---|---|---|---|---|---|---|
| A1, B1 | FTA ®, no additive | 406 | 395 | 345 | 339 | 296 | 237 |
| A2, B2 | FTA ®, 0.01 mg/ml DTT | 452 | 454 | 345 | 343 | 313 | 277 |
| A3, B3 | FTA ®, 2 mM uric acid | 421 | 465 | 375 | 363 | 318 | 257 |
| A4, B4 | FTA ®, 1% Vitamin E | 473 | 474 | 377 | 340 | 303 | 252 |
| A5, B5 | FTA ®, 2% Vitamin E | 447 | 445 | 392 | 313 | 285 | 224 |
| A6, B6 | FTA ®, 160 mg/ml fucose | 440 | 403 | 270 | 191 | 129 | 100 |
| A7, B7 | FTA ®, 320 mg/ml fucose | 454 | 434 | 332 | 252 | 227 | 169 |
| A8, B8 | FTA ®, 160 mg/ml trehalose | 471 | 487 | 445 | 420 | 445 | 389 |
| A9, B9 | FTA ®, 320 mg/ml trehalose | 497 | 504 | 497 | 421 | 437 | 386 |
| A10, B10 | FTA ®, 0.1 mM cystine | 465 | 452 | 407 | 347 | 336 | 298 |
| A11, B11 | FTA ®, 1 mM cystine | 495 | 494 | 392 | 364 | 361 | 311 |
| A12, B12 | FTA ®, no additive | 450 | 463 | 385 | 335 | 331 | 287 |

The study above demonstrates that sensitive proteins such as ferritin can be stored at room temperature under adverse conditions but still be recovered from the adsorbed substrate. Trehalose, in combination with components of FTA®, appears to be a superior combination for 6 preserving peptide.

Table 1B shows typically poor results with any combination of additives with S&S IsoCode™ substrate and Table 1C shows that FTA® substrate with trehalose provides the greatest stability under these conditions.

Figure 31:
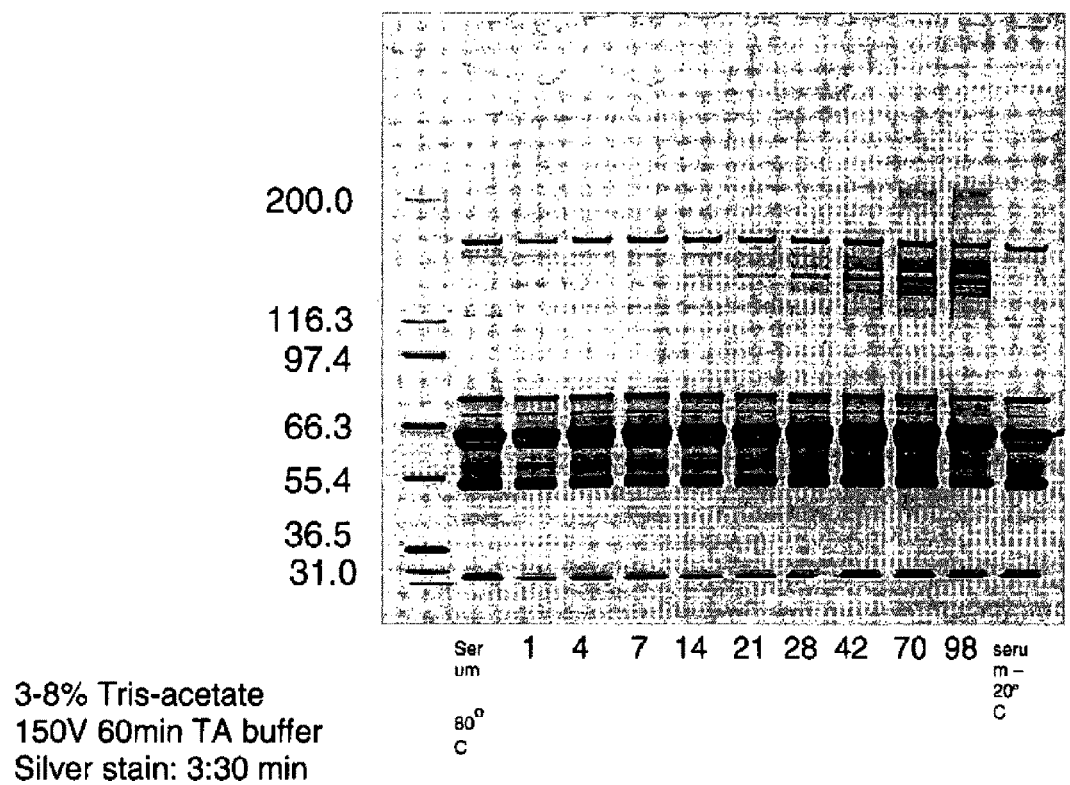
FIG. 31 is a gel electrophoresis, as visualized by silver staining of recovered samples that had been absorbed to substrate and stored at room temperature at intervals up to 98 days. Serum protein samples stored at −20° C. and at −80° C. are shown for comparison.
Figure 32:
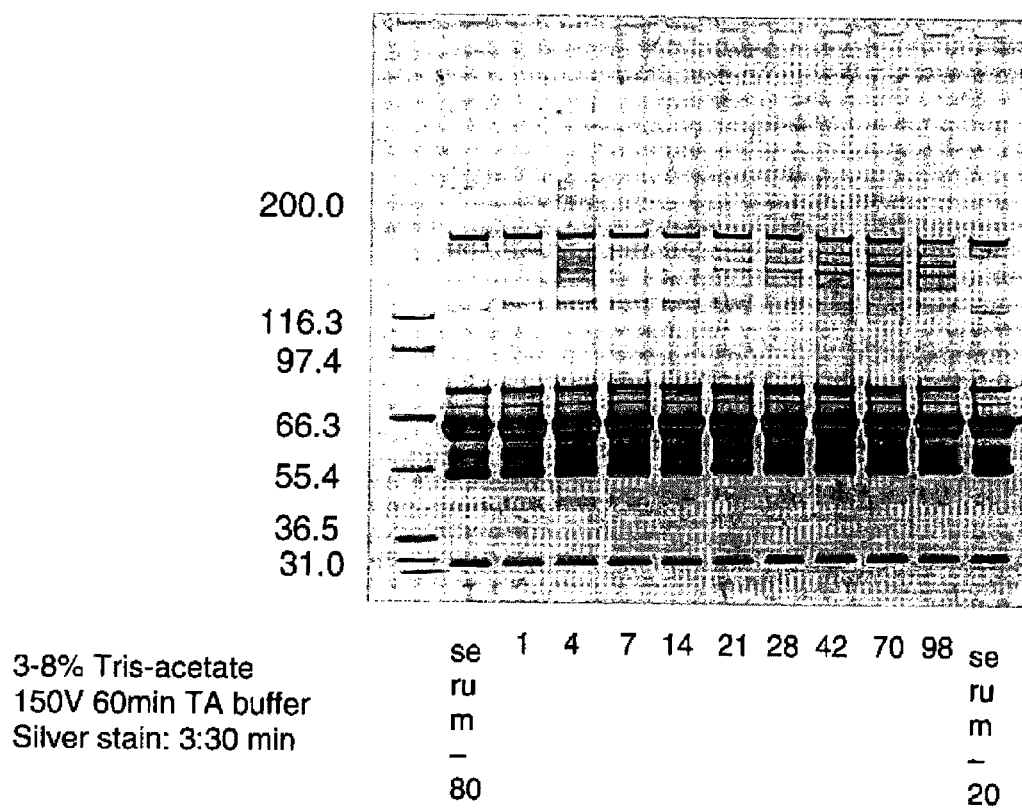
FIG. 32 is a gel electrophoresis, as visualized by silver staining of recovered samples that had been absorbed to substrate and stored at 37° C. at intervals up to 98 days. Serum protein samples stored at −20° C. and at −80° C. are shown for comparison.
Figure 33:
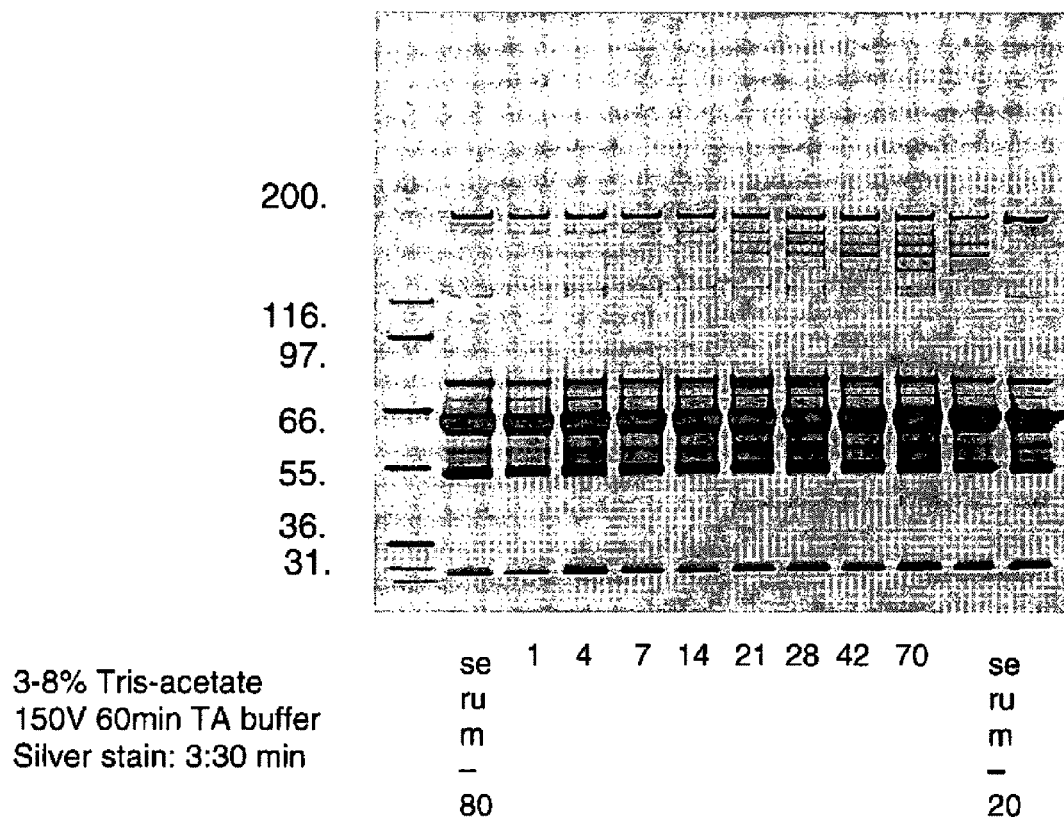
FIG. 33 is a gel electrophoresis, as visualized by silver staining of recovered samples that had been absorbed to substrate and stored at 50° C. at intervals up to 98 days. Serum protein samples stored at −20° C. and at −80° C. are shown for comparison.

FIGS. 31, 32 and 33, are gel electrophoresis, as visualized by silver staining of recovered samples that had been absorbed to substrate and stored at room temperature, 37° C., and 50° C., at intervals up to 98 days. Serum protein samples stored at −20° C. and at −80° C. are shown for comparison.

The results indicate that all of the bands shown in the original samples are present after 98 days in all cases. Some new bands, probably due to breakdown of the large proteins, have begun to appear within several days of initiation of room temperature or hotter storage. Based upon the ferritin data described above, it is not believed that the additional bands represent significant degradation of the proteins, nor are they likely to interfere with proteomic studies, such as LC/MS, MALDI, and other conventional techniques where the proteins are deliberately degraded prior to analysis.

Example 2

This example describes protein storage studies with FTA® substrate and other components.

Sixty 6 mm diameter samples of FTA® paper were treated as follows: 15 with no additive, 15 with 1% vitamin E, 15 with 1 mM cystein, and 15 with 320 mg Trehalose. All of the FTA® samples were absorbed with blood plasma and five samples of the plasma were stored frozen for future use. The total protein in the unfrozen plasma sample was measured using the standard fluorimetric BCA method, and was approximately 1000 μg. The FTA® substrate and frozen samples were the assayed on days 1, 28, 42, 70 and 98. One set of the FTA® substrate samples was store at room temperature (25° C.), one set at 37° C. and one set at 50° C. The results are shown in Table 2. The data demonstrate that samples stored with trehalose show significant, nearly complete protein recovery after 98 days of dry storage at 25° C., 37° C. or 50° C.

Example 3

This example describes additional protein storage studies with different treatments to stabilize protein.

The standard six mm disk of substrate media was used in studies designed to show the efficacy of a combination of substrate media and additives for protein storage. Samples of FTA®, IsoCode™, and untreated cellulose based paper substrate were used in combination with no additive, fucose and trehalose additives. Ten microliters of human blood serum were aliquoted onto each substrate element, allowed to dry and stored. After a designated storage period, the 6 absorbed substrate units were vortexed with 400 microliters of water and the liquid analyzed for protein content. Protein content was compared to samples analyzed for protein prior to absorption onto the substrate elements. The results in Table 3 indicate that trehalose treatment was a superior preservative of peptide as compared to no additive and fucose for long-term storage of proteins.

TABLE 2

Results of storage of Plasma Proteins frozen
and adsorbed to FTA ® at Various Temperatures
Values Indicate Protein recovered in μg

| Temp ° C. | Sample | Day 1 | Day 28 | Day 42 | Day 70 | Day 98 |
| --- | --- | --- | --- | --- | --- | --- |
| 25 | Frozen | 1014 | 1176 | 952 | 1080 | 1039 |
| 25 | FTA ® | 1008 | 808 | 398 | 350 | 285 |
| 25 | FTA ® + 1% Vit E | 798 | 668 | 530 | 429 | 402 |
| 25 | FTA ® + 1 mM Cystine | 1131 | 987 | 896 | 717 | 663 |
| 25 | FTA ® + 320 mg Treh. | 1115 | 994 | 921 | 986 | 1059 |
| 37 | FTA ® | 715 | 411 | 672 | 268 | 312 |
| 37 | FTA ® + 1% Vit E | 494 | 452 | 433 | 323 | 375 |
| 37 | FTA ® + 1 mM Cystine | 1036 | 910 | 770 | 600 | 648 |
| 37 | FTA ® + 320 mg Treh. | 1073 | 1166 | 1017 | 891 | 1233 |
| 50* | FTA ® | 838 | 394 | 486 | 248 | 258 |
| 50* | FTA ® + 1% Vit E | 949 | 487 | 651 | 312 | 295 |
| 50* | FTA ® + 1 mM Cystine | 1561 | 954 | 1093 | 762 | 526 |
| 50* | FTA ® + 320 mg Treh. | 1333 | 1243 | 1279 | 925 | 1201 |

*Days 1, 28, and 42 at 50° C. include the total of a first and second wash to remove protein.

TABLE 3

Results of Additives on Dry, Room Temperature Protein Storage
Serum Protein Stability Study - total protein assay: BCA method (0.4 ml)

| | | Concentration in µg/ml | Day 1 | Day 28 | Day 42 | Day 70 | Day 98 |
|---|---|---|---|---|---|---|---|
| room temp | 1 | FTA ®, no additives | 2519 | 2020 | 996 | 875 | 711 |
| room temp | 3 | FTA ® + 1% Vit E | 1995 | 1671 | 1325 | 1073 | 1005 |
| room temp | 5 | FTA ® + 1 mM cystine | 2828 | 2467 | 2239 | 1793 | 1656 |
| room temp | 7 | FTA ® + 320 mg trehalose | 2787 | 2484 | 2303 | 2464 | 2647 |
| room temp | 9 | S&S 903 ™ with "super-goop" (SG) | 2103 | 1651 | 1101 | 550 | 495 |
| room temp | 11 | S&S 903 ™ + SG + 1% Vit E | 2168 | 1967 | 1312 | 864 | 735 |
| room temp | 13 | S&S 903 ™ + SG + 1 mM Cystine | 2459 | 1743 | 1101 | 512 | 502 |
| room temp | 15 | S&S 903 ™ + SG + 320 mg/ml trehalose | 2275 | 2407 | 2171 | 1909 | 1971 |
| 37° C. | 17 | FTA ®, no additives | 1787 | 1028 | 1681 | 671 | 779 |
| 37° C. | 19 | FTA ® + 1% Vit E | 1236 | 1131 | 1083 | 807 | 936 |
| 37° C. | 21 | FTA ® + 1 mM cystine | 2591 | 2275 | 1924 | 1499 | 1618 |
| 37° C. | 23 | FTA ® + 320 mg trehalose | 2682 | 2914 | 2542 | 2228 | 3080 |
| 37° C. | 25 | S&S 903 ™ with "super-goop" (SG) | 2134 | 1643 | 1171 | 1115 | 1599 |
| 37° C. | 27 | S&S 903 ™ + SG + 1% Vit E | 2755 | 1675 | 1398 | 1503 | 1398 |
| 37° C. | 29 | S&S 903 ™ + SG + 1 mM cystine | 2528 | 1808 | 1452 | 1353 | 1345 |
| 37° C. | 31 | S&S 903 ™ + SG + 320 mg/ml trehalose | 2328 | 2257 | 2211 | 2009 | 2226 |
| 50° C. | 33 | FTA ®, no additives | 1370 | 680 | 608 | 621 | 646 |
| 50° C. | 35 | FTA ® + 1% Vit E | 1694 | 793 | 935 | 780 | 736 |
| 50° C. | 37 | FTA ® + 1 mM cystine | 3132 | 1480 | 2079 | 1904 | 1313 |
| 50° C. | 39 | FTA ® + 320 mg trehalose | 2821 | 2646 | 2737 | 2313 | 3002 |
| 50° C. | 41 | S&S 903 ™ with "super-goop" (SG) | 1888 | 738 | 794 | 574 | 460 |
| 50° C. | 43 | S&S 903 ™ + SG + 1% Vit E | 2348 | 886 | 1025 | 712 | 722 |
| 50° C. | 45 | S&S 903 ™ + SG + 1 mM cystine | 2274 | 1093 | 1121 | 818 | 658 |
| 50° C. | 47 | S&S 903 ™ + SG + 320 mg/ml trehalose | 2052 | 2045 | 1998 | 1929 | 2213 |

SG = 160 mM Tris, 10 mM EDTA, 2% NP40 detergent.
S&S 903 ™ is 100% Rag Cellulose paper from Schleicher & Schuell SG treated paper substrate in combination with trehalose provides excellent protein stability and protein recovery. This combination excludes the uric acid used in FTA® for a free radical trap, which is not necessary for preserving stored protein. Phosphatase and protease inhibitors may also be added to reduce the incidence of protein degradation by those agents. It is likely that the detergent and EDTA used may well inhibit most enzymes by either denaturing them or by removing the metal ions used as cofactors or active centers in metalloenzymes.

Example 4

This example describes an exemplary protocol for absorbing and subsequently eluting and recovering a sample (serum or blood) from an elutable elastomeric substrate (polyester sponge). This example also describes an exemplary protocol for absorbing and subsequently recovering nucleic acid from an elutable elastomeric substrate (polyester sponge). This example additionally describes an exemplary protocol for absorbing and subsequently recovering peptide from an elutable elastomeric substrate (polyester sponge), followed by subsequent nucleic acid elution and recovery from the same substrate.

A. Protocol for Protein Recovery from Blood Absorbed to Sponge
Sample Application:
1. Prepare a sample of blood, serum or plasma.
2. Dispense 150 µL of sample into each well of a plate bearing the elastomeric substrate
3. Allow the substrate to dry in a controlled atmosphere.
4. Seal each sample container with a pierceable seal material for storage.
5. Place the plate into a storage unit for archiving.
Protein Recovery:
1. Remove selected plates of stored plasma protein from the storage unit and place the desired number of sample vials containing stored plasma protein into the Study Plate.
2. Add 150 µL of water to each vial and compress the elastomeric substrate several times with the cap plunger to ensure hydration of substrate.
3. Allow the elastomeric substrate to incubate with water at room temperature for ten minutes and then push in the plunger completely on each sample to expel the plasma protein from the substrate and into the hollow barrel of the plunger.
4. Recover the water containing plasma protein for study by piercing the top seal on the plunger with a needle or pipette tip to withdraw the desired amount.

B. Protocol for Nucleic Acid Recovery from a Sample Absorbed to Sponge
Sample Application:
1. Insert a sponge into a suitable vessel, such as the vessel illustrated in FIGS. 2 and 3, and apply a volume of nucleic acid sample (e.g., 150 ul) to sponge. NOTE: Sample may not absorb into sponge immediately.
2. Allow nucleic acid sample to absorb onto sponge for 5 minutes. Using a trimmed 200 ul pipette tip (trim the first 5 mm off with a clean razor blade), compress the sponge up and down several times to ensure that the nucleic acid is completely adsorbed into the sponge.
3. Let sample air-dry overnight in a safety hood. NOTE: It may be necessary to increase the drying time in humid conditions.
Nucleic Acid Recovery:
1. Add 150 µL of alkaline recovery liquid at pH 11.7-11.8 to the sponge to the substrate and compress the sponge several times with the cap plunger to ensure hydration of substrate.
2. Allow the substrate to incubate with the alkaline recovery liquid at room temperature for ten minutes and then push in the plunger completely on each sample to expel the nucleic acid from the substrate and into the hollow barrel of the plunger.
3. Recover the alkaline liquid containing nucleic acid for study using a pipette tip to withdraw the desired amount.

4. Optionally repeat steps 1-3 for a total of 2 cycles.
5. Combine all eluate solutions C. Protocol for Two Step Protein then Nucleic Acid Recovery from Blood Absorbed to Sponge Sample Application:
1. Insert a sponge into a suitable vessel, such as a spin column (e.g., a spin column comparable to the BioRad microspin column, cat#732-6204), and apply 150 ul of well-mixed blood (whole, plasma or serum) to sponge. NOTE: Sample may not absorb into sponge immediately.
2. Allow blood to absorb onto sponge for 5 minutes. Using a trimmed 200 ul pipette tip (trim the first 5 mm off with a clean razor blade), compress the sponge up and down several times to ensure that the blood is completely adsorbed into the sponge.
3. Let sample air-dry overnight in a safety hood.
NOTE: It may be necessary to increase the drying time in humid conditions. A completely dried sample will be difficult to compress and be noticeably darker in color.

Sample Recovery:
A. Protein
1. Cap the bottom of the spin column during the elution process.
2. Place whole assembly into clean 2 ml microfuge tube.
3. Add 150 ul of ultra pure water to sponge.
4. Compress 20 times with trimmed 200 ul pipette tip and incubate at room temperature for 10 minutes.
5. Repeat step 4 twice for a total of 3 cycles.
6. Remove bottom cap from tube and centrifuge in a microcentrifuge for 1 minute at 10,000×g.
7. Recover eluate fluid for subsequent protein studies.
8. Retain sponge in spin column for DNA recovery.

B. DNA
9. Re-cap the bottom of the spin column, and keep capped during the elution process.
10. Place spin column assembly into clean 2 ml microfuge tube.
11. Add 150 μl of Proteinase K (stock at 20 ug/ul) in a lysis buffer (such as Qiagen ATL buffer) at a final concentration of 100 μg/ml.
12. Heat at 56° C. for 20 minutes
13. Remove bottom cap from tube and centrifuge in a microcentrifuge for 1 minute at 10,000×g and retain liquid
14. Cap the bottom of the spin column, and keep capped during the elution process.
15. Place whole assembly into clean 2 ml microfuge tube
16. Add 200 ul of alkaline Recovery liquid at pH 11.7-11.8 to the sponge.
17. Compress 20 times with trimmed 200 ul pipette tip and incubate at room temperature for 30 minutes.
18. Compress 20 times after the incubation.
19. Remove bottom cap from tube and centrifuge in a microcentrifuge for 1 minute at 10,000×g.
20. Add 10 ul of Tris-HCL to neutralize the high pH and retain liquid.
21. Cap the bottom of the spin column, and keep capped during the elution process.
22. Place whole assembly into clean 2 ml microfuge tube.
23. Repeat steps 7-12 for a total of 2 cycles.
24. Combine all retained solutions (steps B.5, B.12-twice) and complete the recovery process with the a magnetic bead procedure (e.g., Invitrogen DRI magnetic bead purification kit or QIAmp micro and mini kits available from Qiagen).

Example 5

This example describes an exemplary vessel storage unit. The storage unit (vessel or tube) is suitable for housing the substrate, absorbing a sample to the substrate, storing absorbed substrate, and for elution or recovery of the absorbed sample from the substrate.

Figure 3:
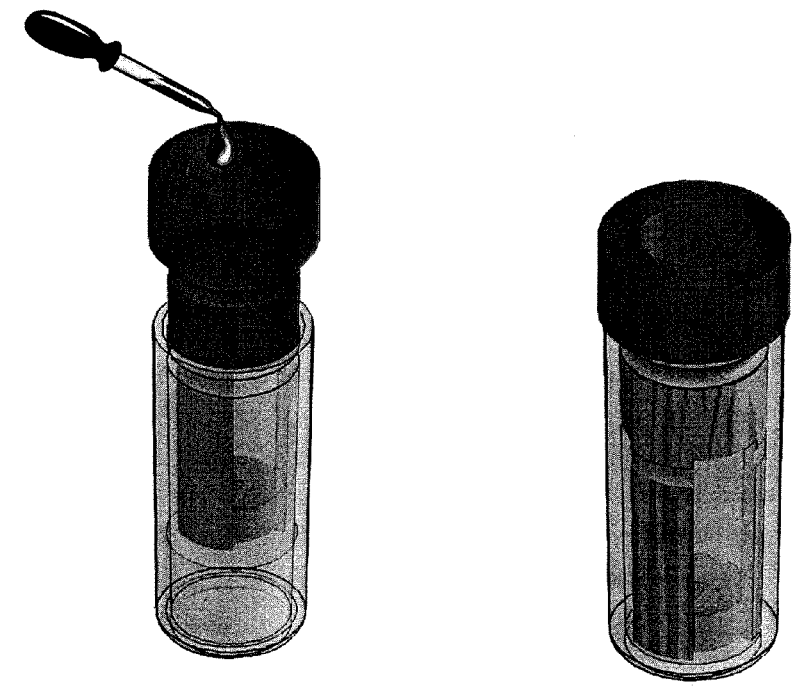
FIG. 3 is a schematic diagram of sample hydration and recovery from substrate (sponge) housed in a vessel (storage unit, vial) after selection of the approriate stored sample. The sponge to which sample (e.g., serum or plasma) has been absorbed is hydrated and a cap/plunger assembly is used to compress the sponge thereby eluting the sample from the sponge, which in turn can be recovered and subjected to a subsequent analysis or application.
Figure 4:
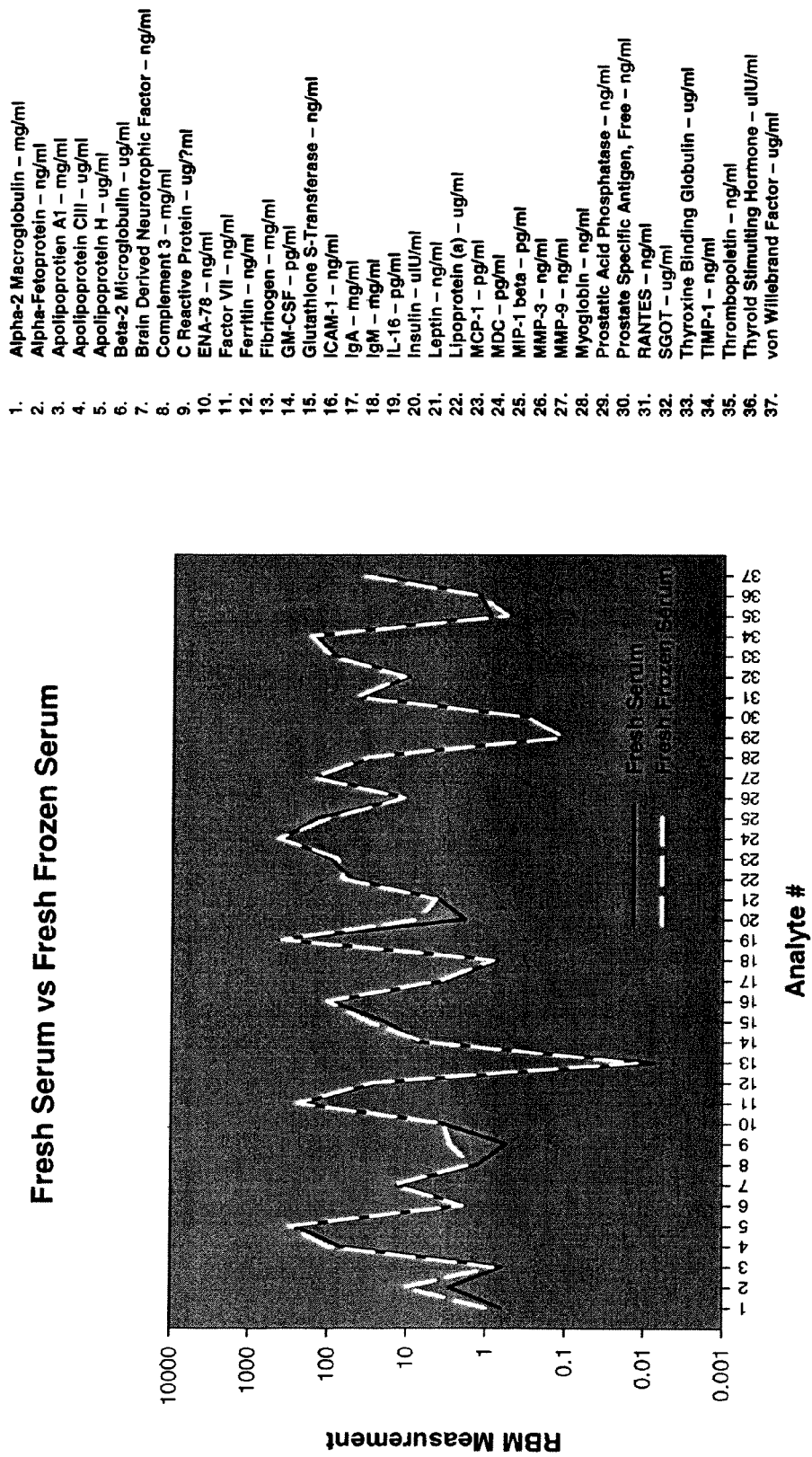
FIG. 4 is a graphical illustration of the quantity of various serum analytes in fresh vs. frozen serum (seven days).
Figure 5:
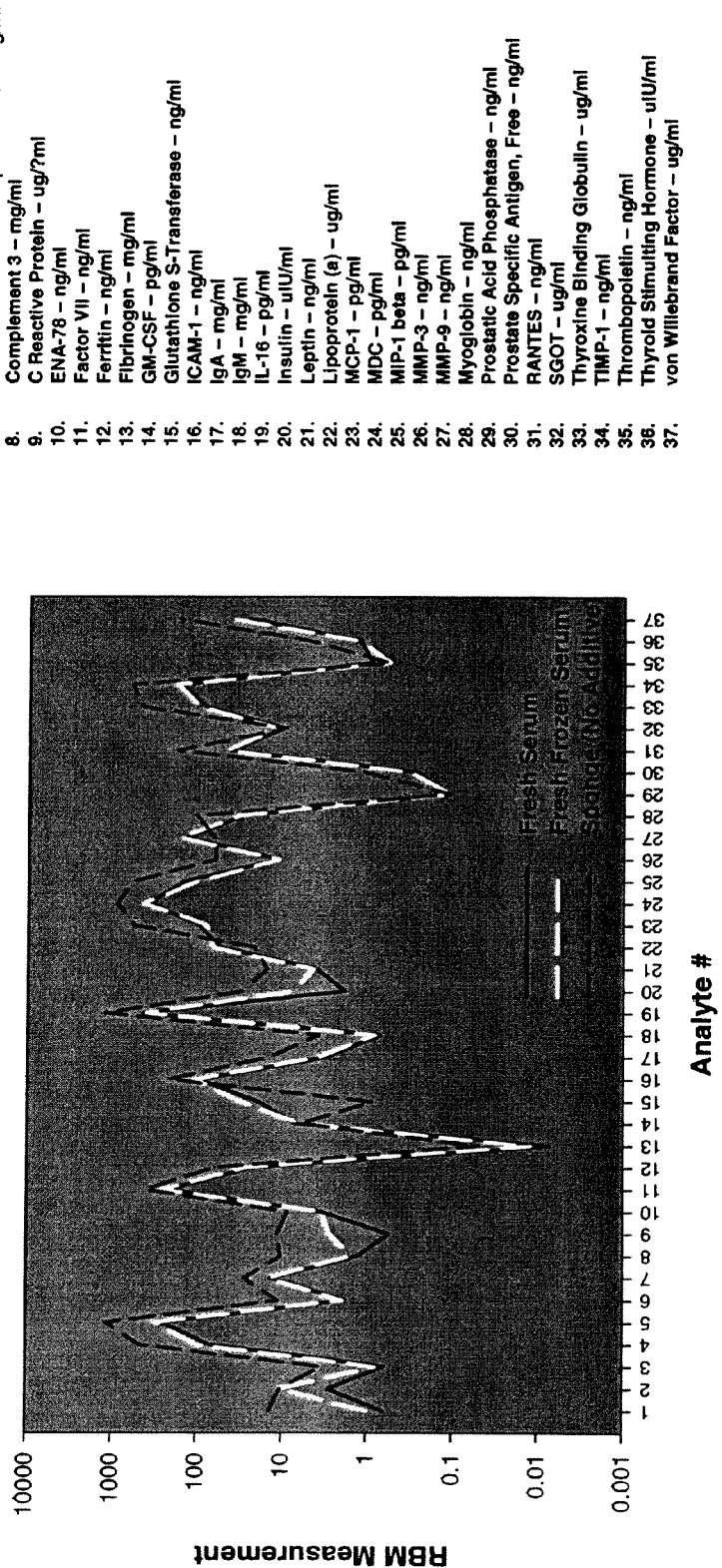
FIG. 5 is a graphical illustration of the quantity of various serum analytes stored on sponge (no treatment) at room temperature after seven days, vs fresh and frozen serum (see the data presented in Tables 5-7).
Figure 7:
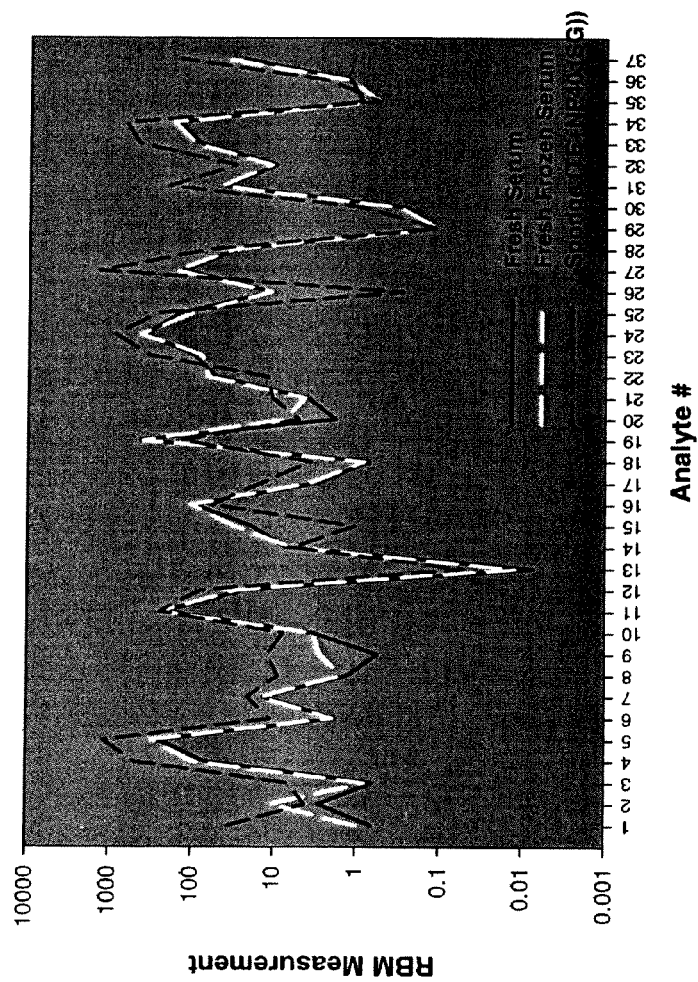
FIG. 7 is a graphical illustration of the quantity of various serum analytes stored on sponge (TE+NP40) at room temperature after seven days, vs. fresh and frozen serum (see the data presented in Tables 5-7).
Figure 8:
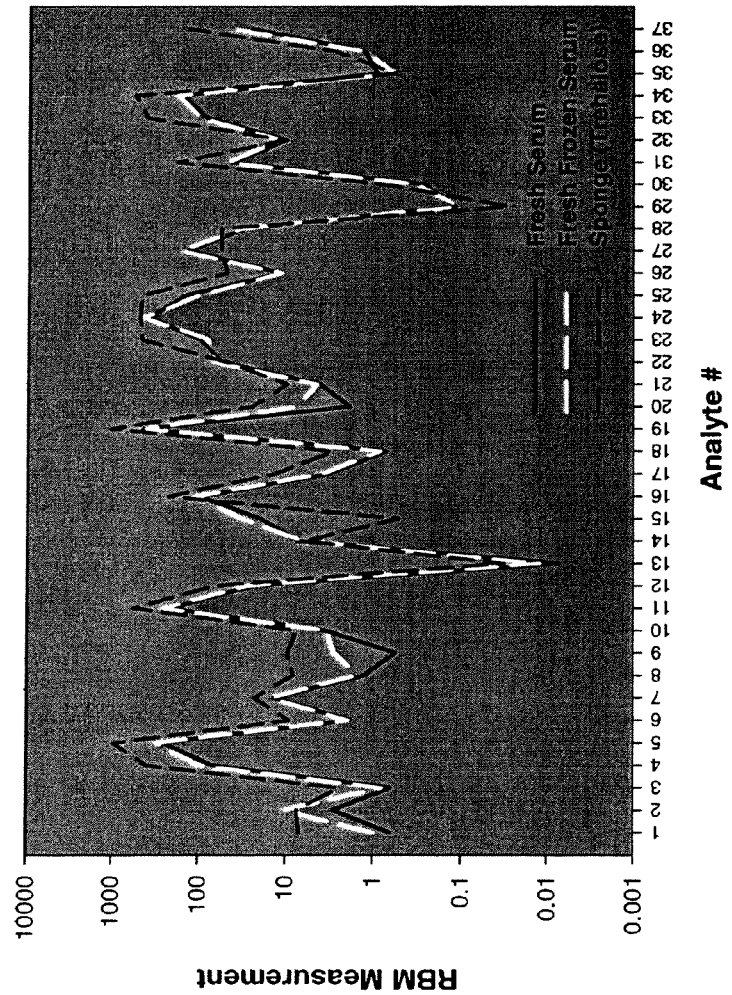
FIG. 8 is a graphical illustration of the quantity of various serum analytes stored on sponge (Trehalose) at room temperature after seven days, vs. fresh and frozen serum (see the data presented in Tables 5-7).
Figure 9:
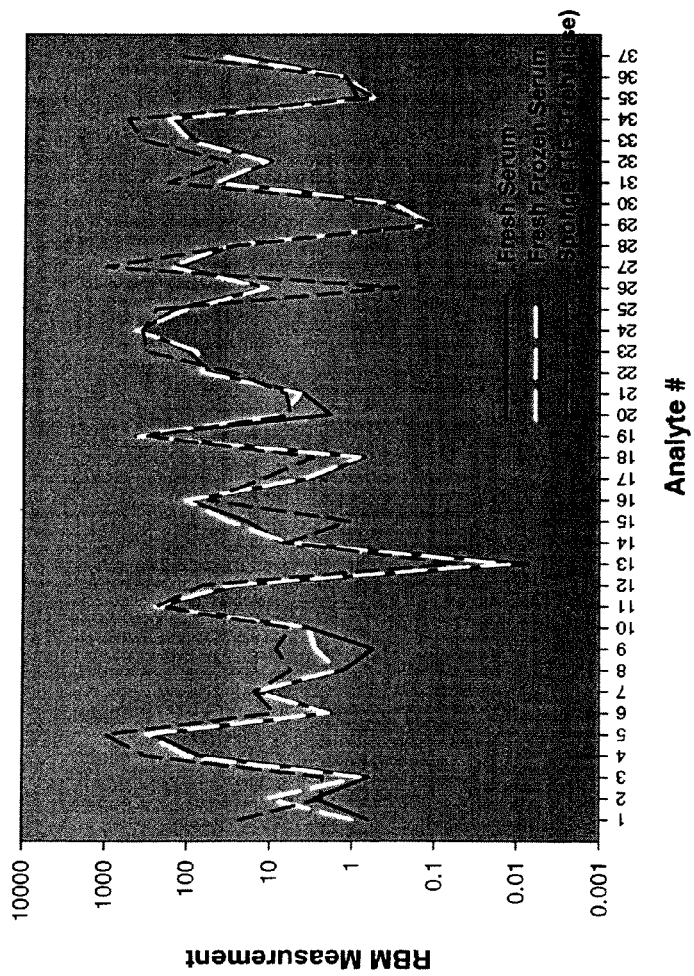
FIG. 9 is a graphical illustration of the quantity of various serum analytes stored on sponge (TE+Trehalose) at room temperature after seven days, vs. fresh and frozen serum (see the data presented in Tables 5-7).
Figure 10:
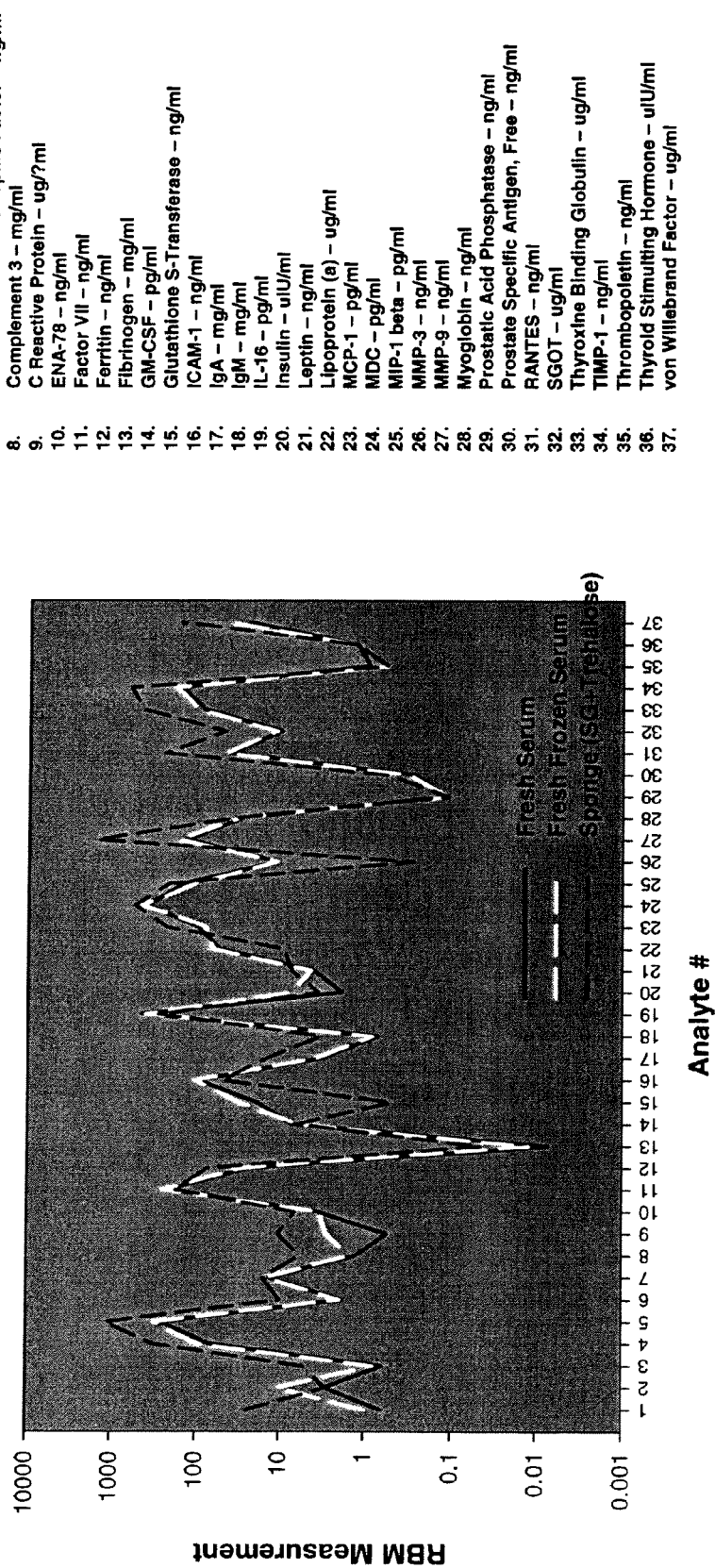
FIG. 10 is a graphical illustration of the quantity of various serum analytes stored on sponge (TE+Trehalose+NP40) at room temperature after seven days, vs. fresh and frozen serum (see the data presented in Tables 5-7).
Figure 11:
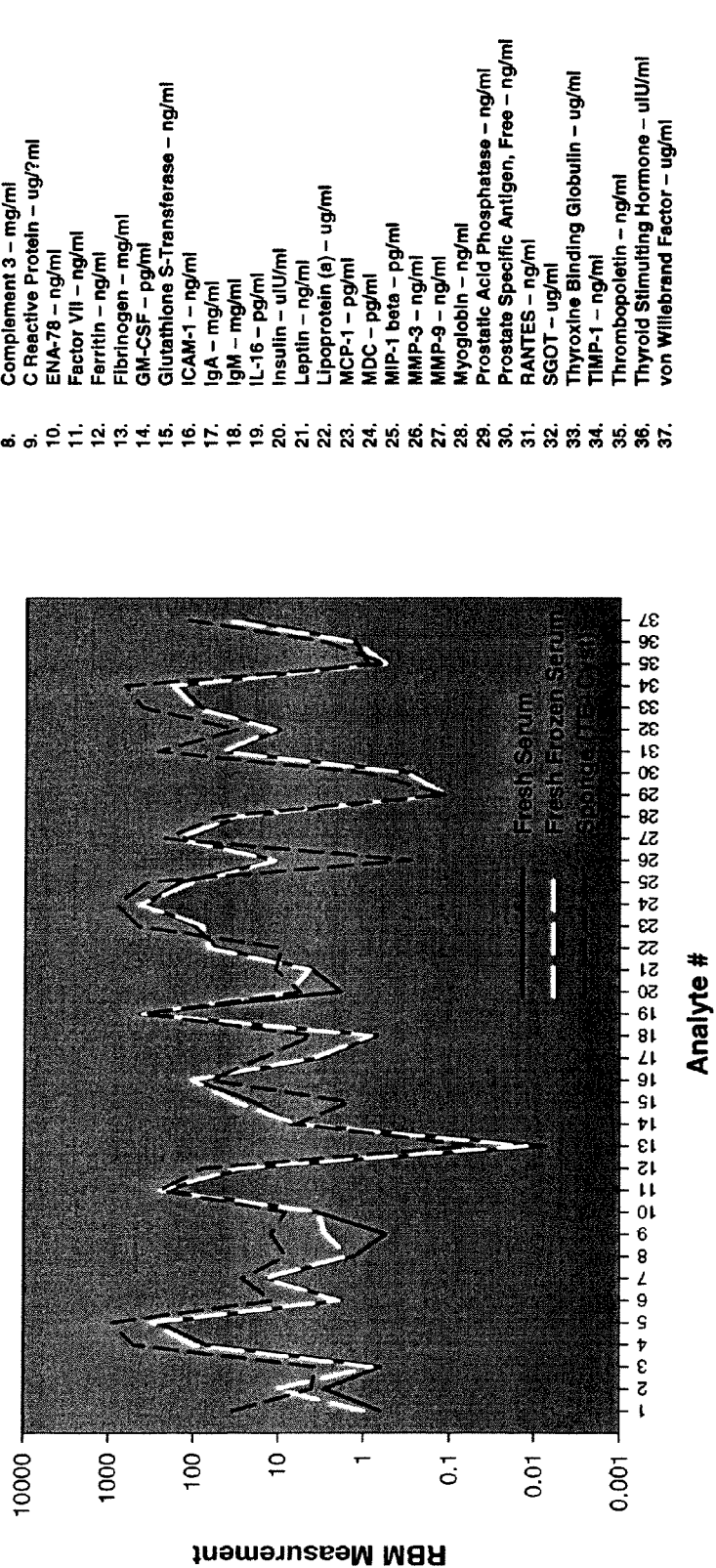
FIG. 11 is a graphical illustration of the quantity of various serum analytes stored on sponge (TE+Cysteine) at room temperature after seven days, vs. fresh and frozen serum (see the data presented in Tables 5-7).
Figure 12:
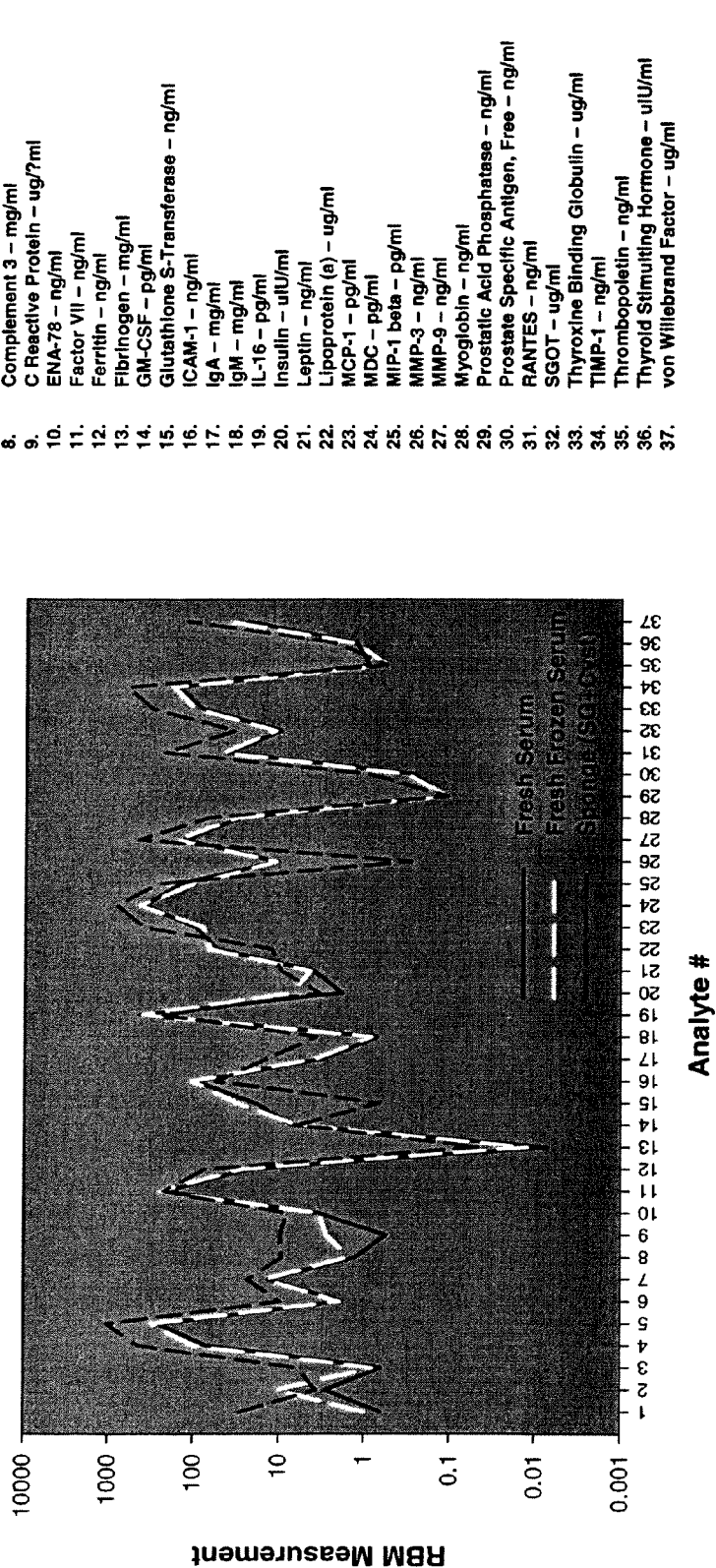
FIG. 12 is a graphical illustration of the quantity of various serum analytes stored on sponge (TE+Cysteine+NP40) at room temperature after seven days, vs. fresh and frozen serum (see the data presented in Tables 5-7).
Figure 14:
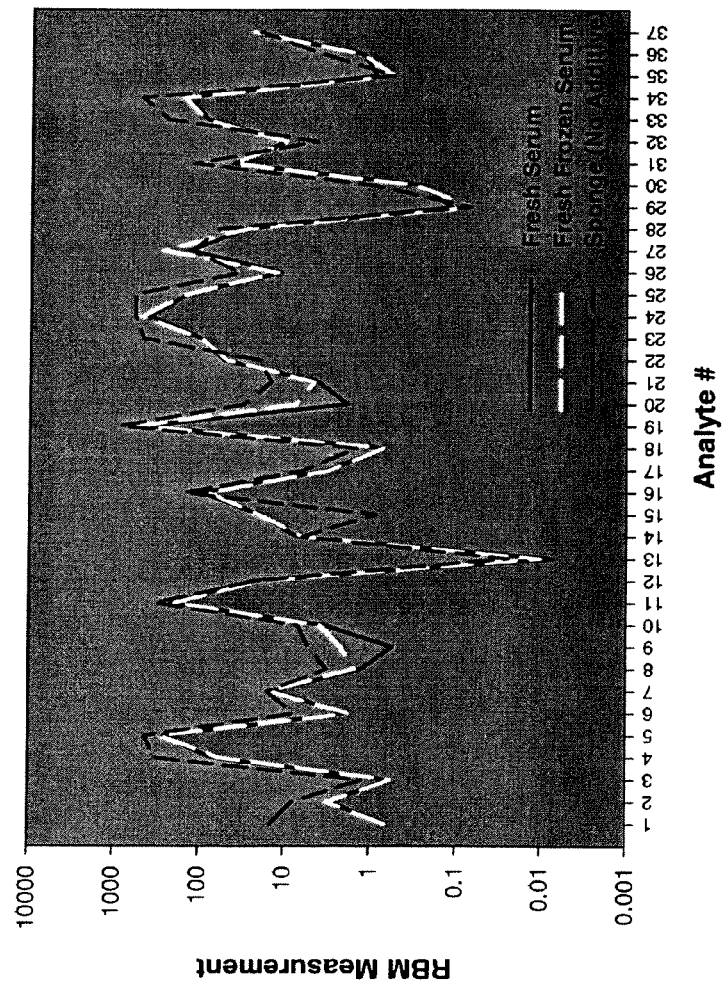
FIG. 14 is a graphical illustration of the quantity of various serum analytes stored on sponge (no treatment) at room temperature after 55 days, vs. fresh and frozen serum (see the data presented in Tables 5-7).
Figure 15:
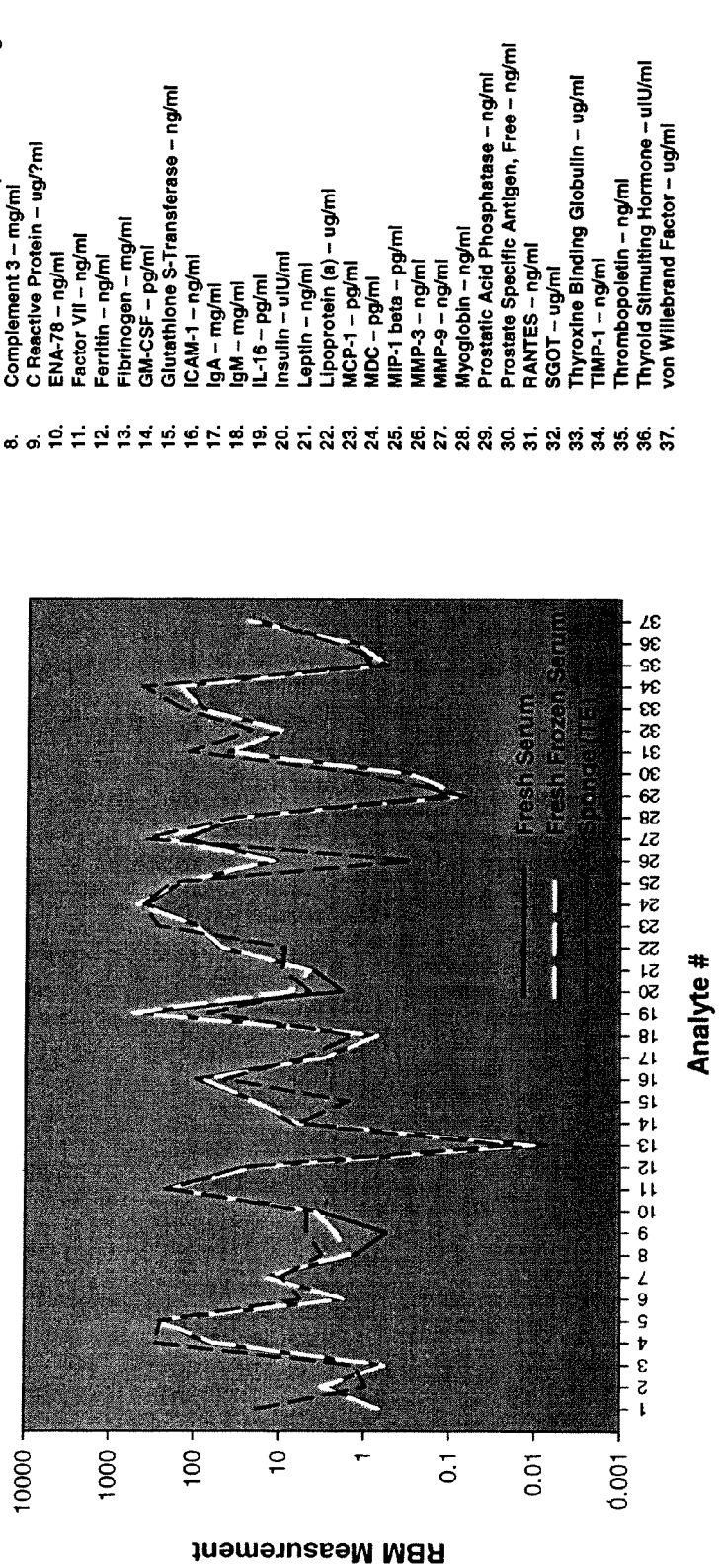
FIG. 15 is a graphical illustration of the quantity of various serum analytes stored on sponge (TE) at room temperature after 55 days, vs. fresh and frozen serum (see the data presented in Tables 5-7).
Figure 16:
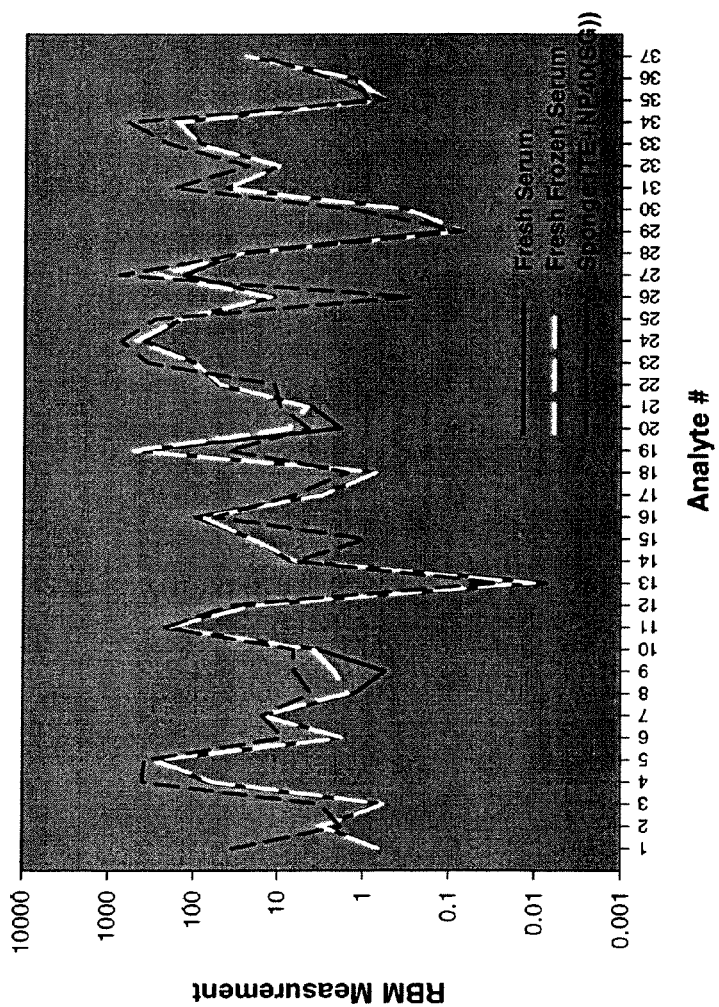
FIG. 16 is a graphical illustration of the quantity of various serum analytes stored on sponge (TE+NP40) at room temperature after 55 days, vs. fresh and frozen serum (see the data presented in Tables 5-7).
Figure 17:
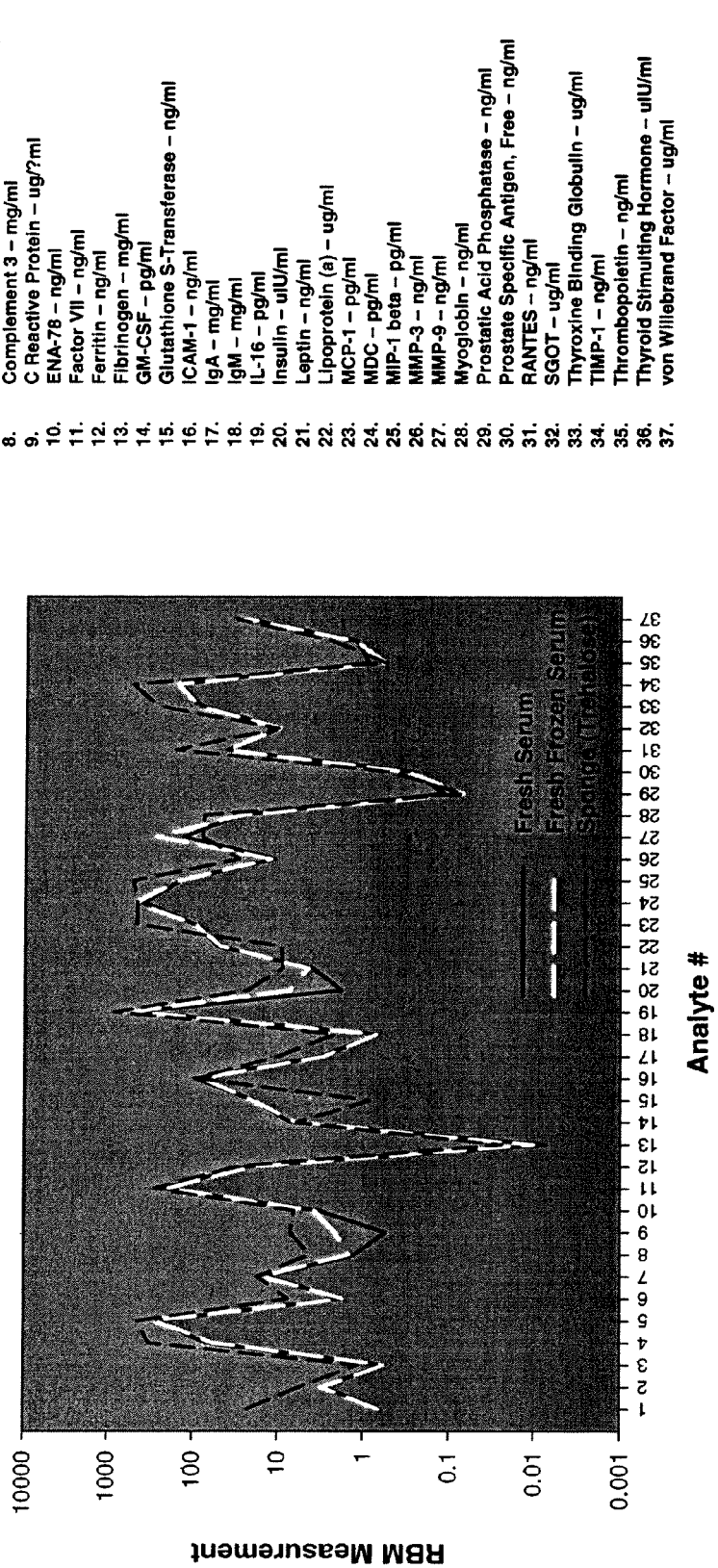
FIG. 17 is a graphical illustration of the quantity of various serum analytes stored on sponge (Trehalose) at room temperature after 55 days, vs. fresh and frozen serum (see the data presented in Tables 5-7).
Figure 18:
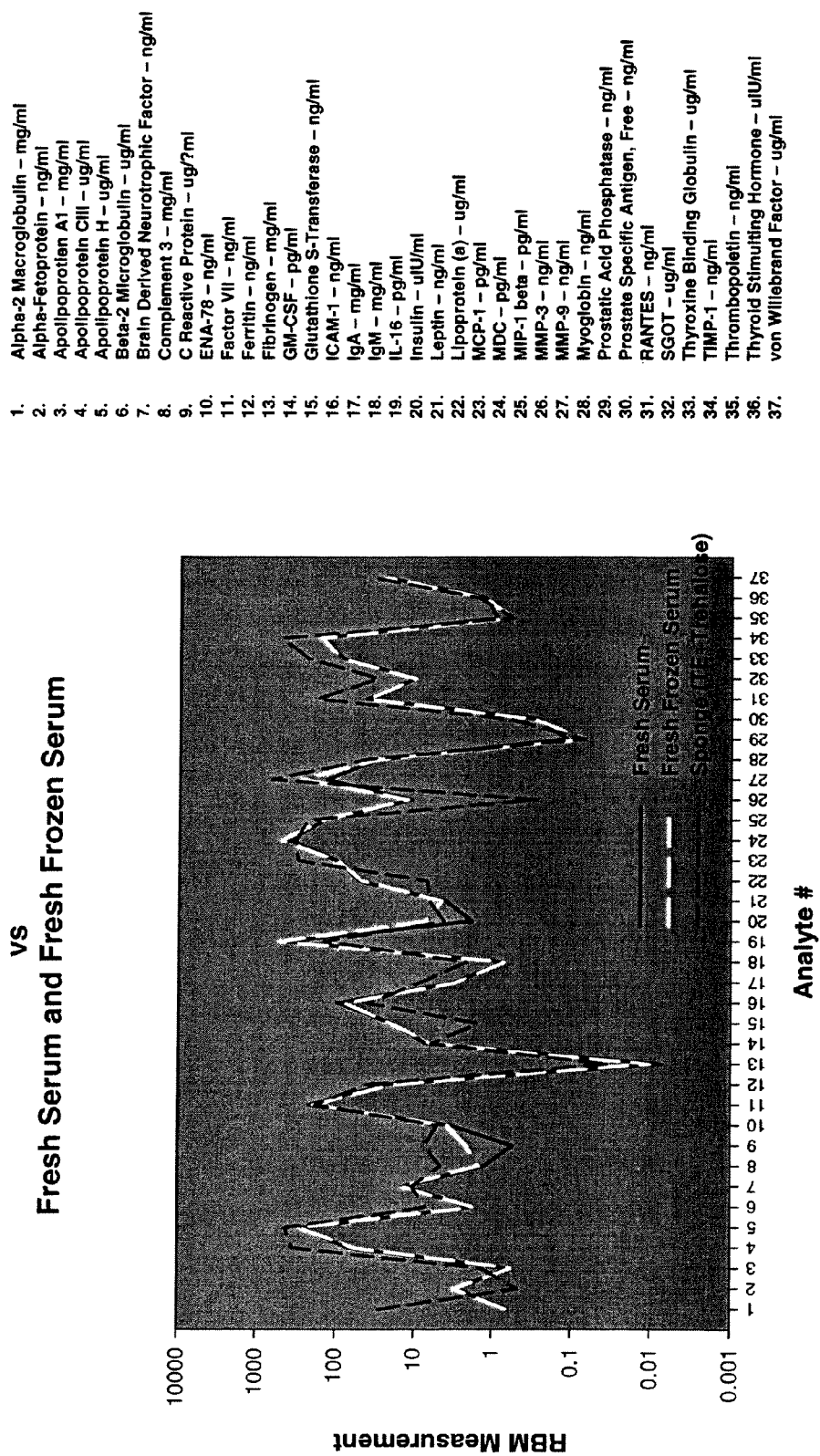
FIG. 18 is a graphical illustration of the quantity of various serum analytes stored on sponge (TE+Trehalose) at room temperature after 55 days, vs. fresh and frozen serum (see the data presented in Tables 5-7).
Figure 19:
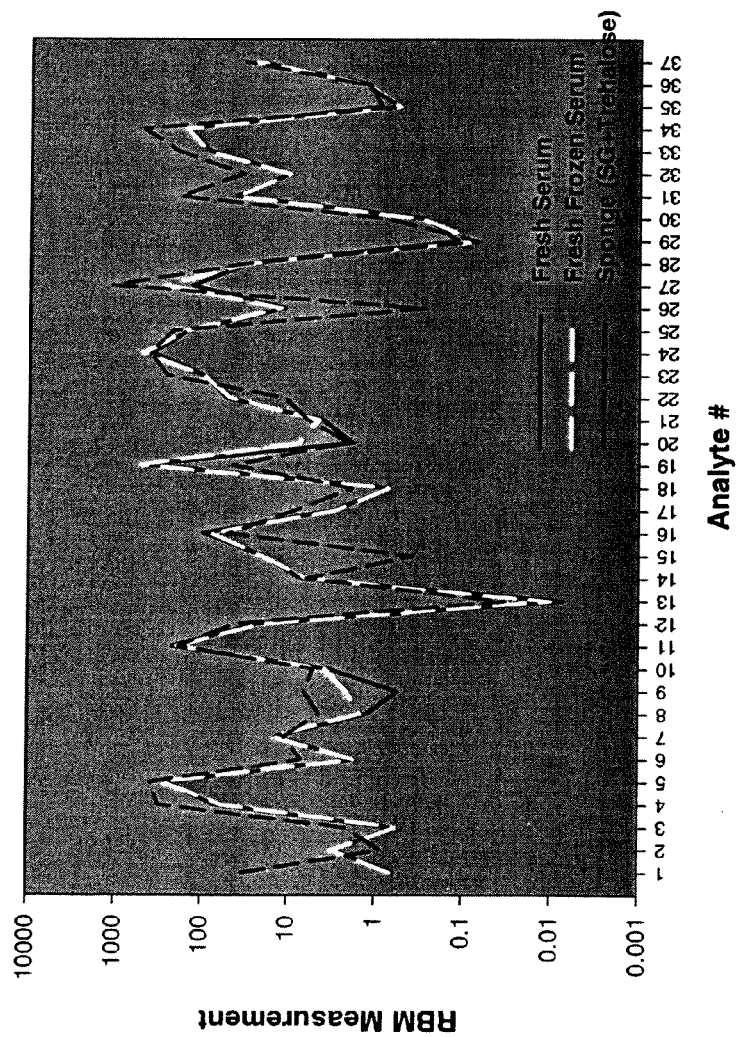
FIG. 19 is a graphical illustration of the quantity of various serum analytes stored on sponge (TE+Trehalose+NP40) at room temperature after 55 days, vs. fresh and frozen serum (see the data presented in Tables 5-7).
Figure 20:
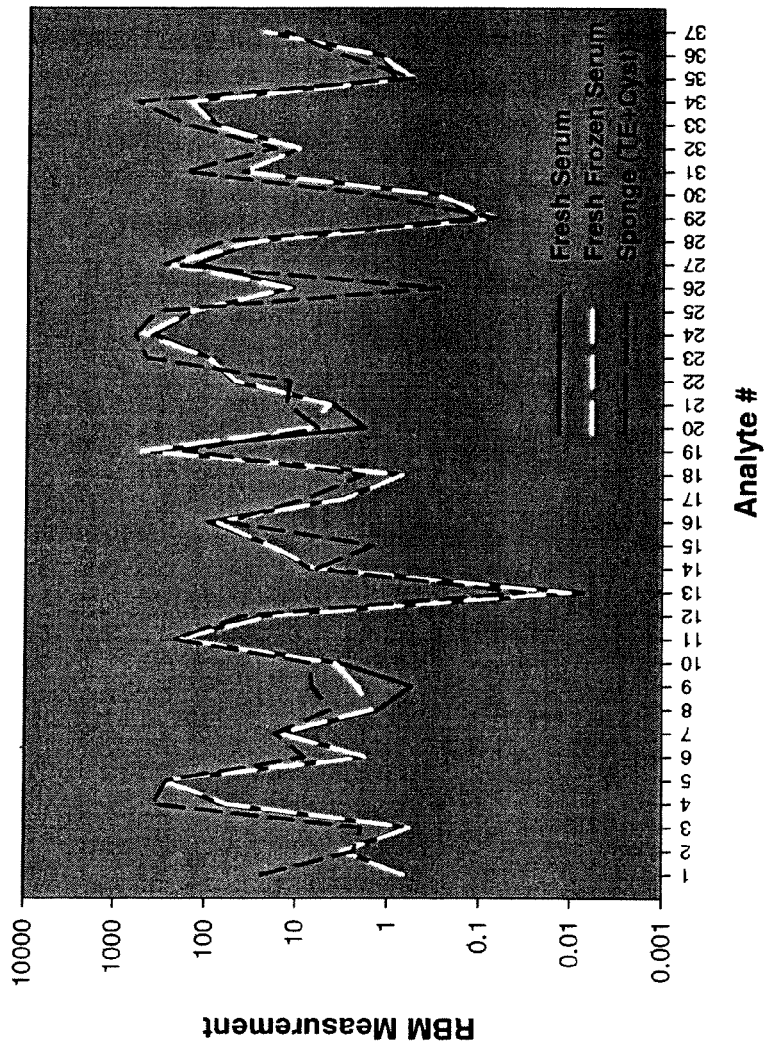
FIG. 20 is a graphical illustration of the quantity of various serum analytes stored on sponge (TE+Cysteine) at room temperature after 55 days, vs. fresh and frozen serum (see the data presented in Tables 5-7).
Figure 22:
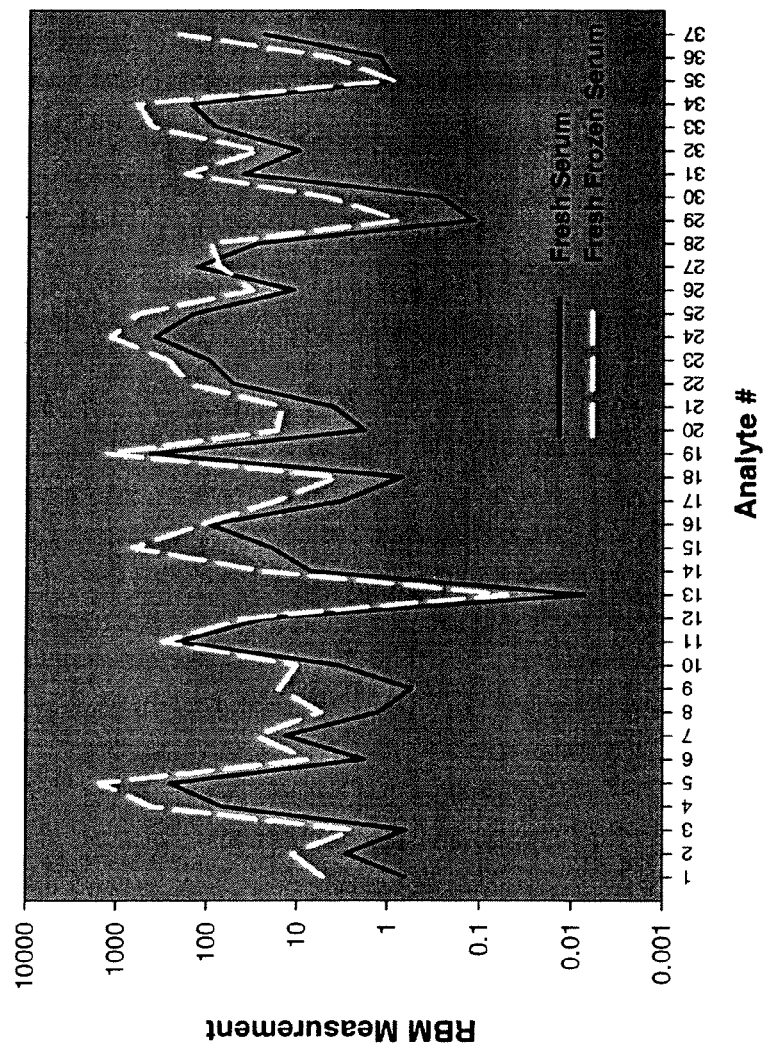
FIG. 22 is a graphical illustration of the quantity of various serum analytes of various serum analytes in fresh vs. frozen serum (187 days).
Figure 24:
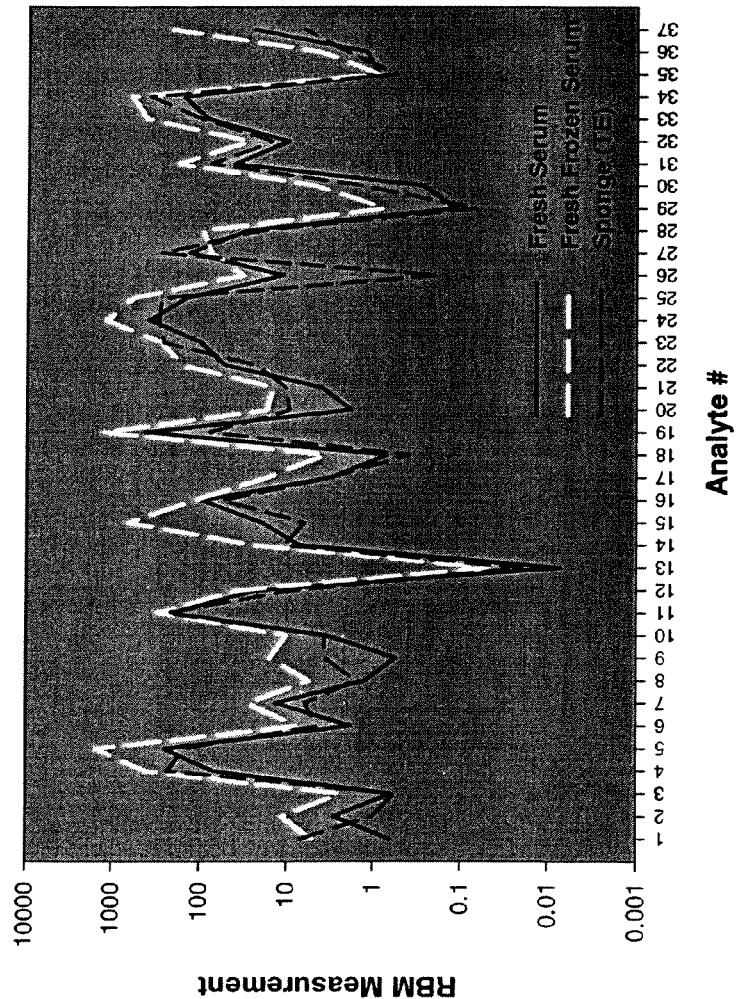
FIG. 24 is a graphical illustration of the quantity of various serum analytes stored on sponge (TE) at room temperature after 187 days, vs. fresh and frozen serum (see the data presented in Tables 5-7).
Figure 25:
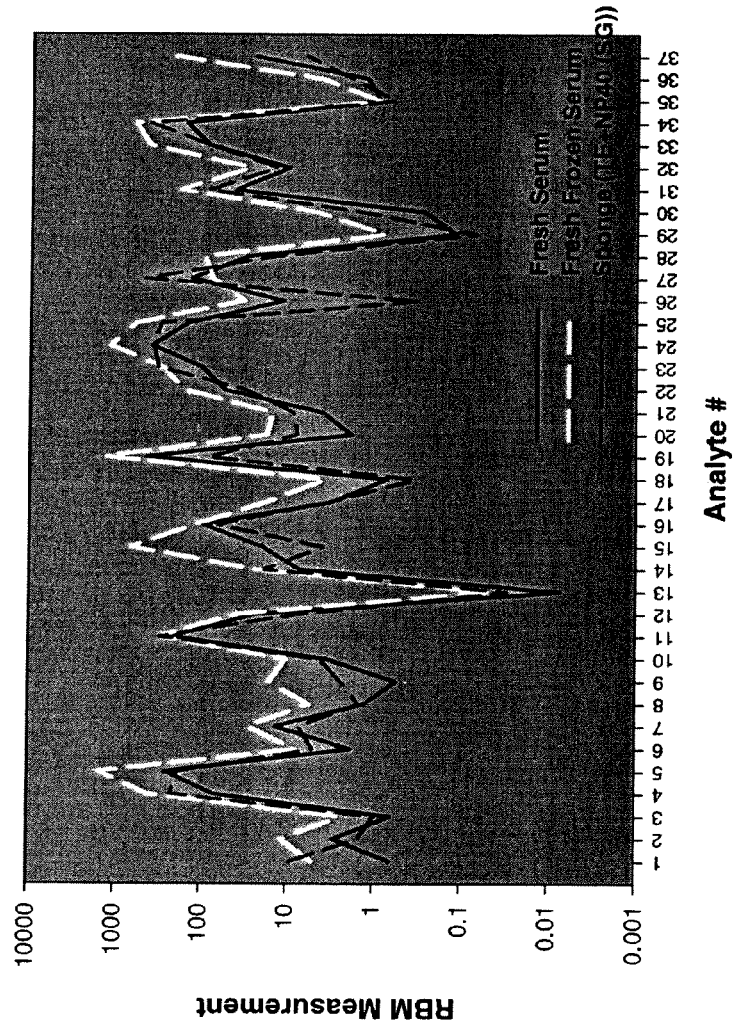
FIG. 25 is a graphical illustration of the quantity of various serum analytes stored on sponge (TE+NP40) at room temperature after 187 days, vs. fresh and frozen serum (see the data presented in Tables 5-7).
Figure 26:
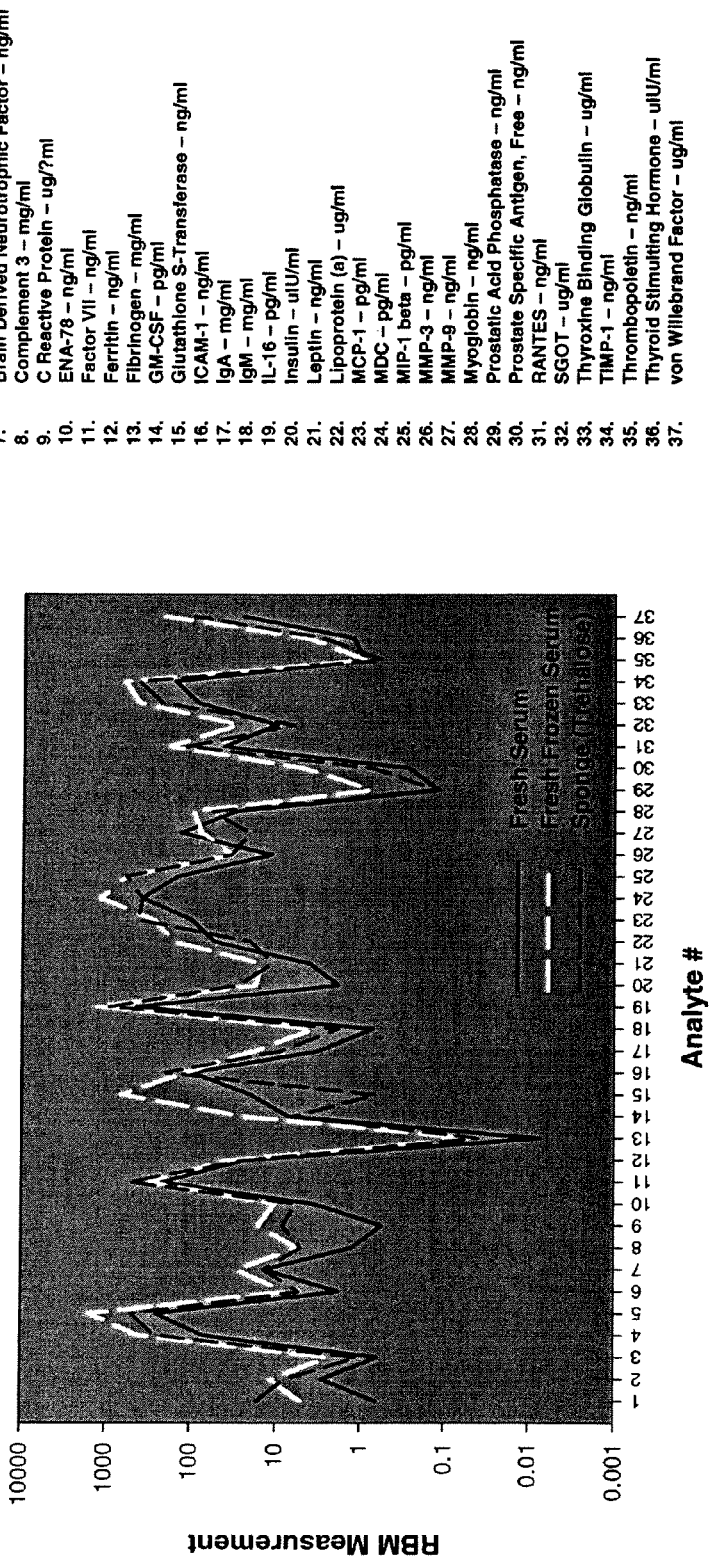
FIG. 26 is a graphical illustration of the quantity of various serum analytes stored on sponge (Trehalose) at room temperature after 187 days, vs. fresh and frozen serum (see the data presented in Tables 5-7).
Figure 27:
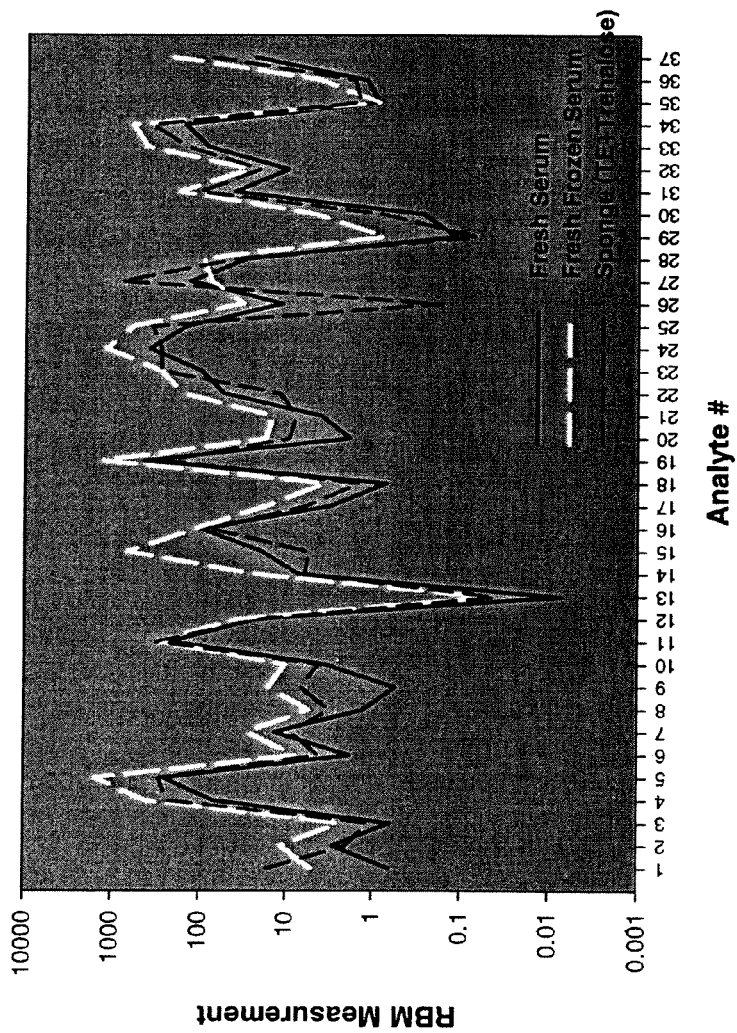
FIG. 27 is a graphical illustration of the quantity of various serum analytes stored on sponge (TE+Trehalose) at room temperature after 187 days, vs. fresh and frozen serum (see the data presented in Tables 5-7).
Figure 28:
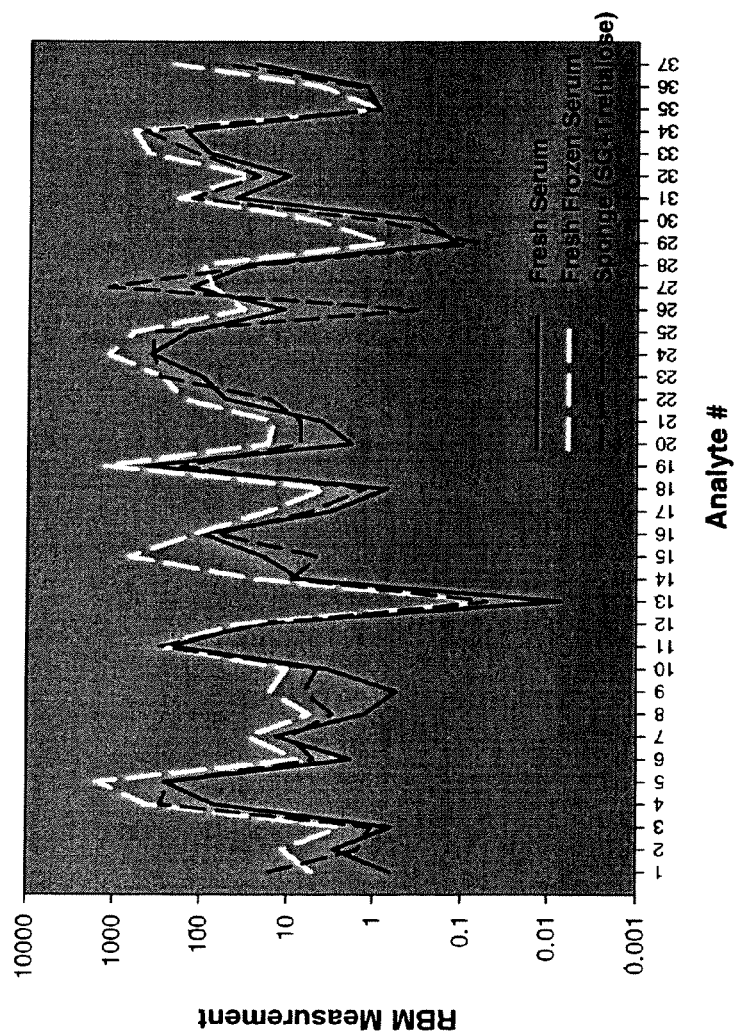
FIG. 28 is a graphical illustration of the quantity of various serum analytes stored on sponge (TE+Trehalose+NP40) at room temperature after 187 days, vs. fresh and frozen serum (see the data presented in Tables 5-7).
Figure 29:
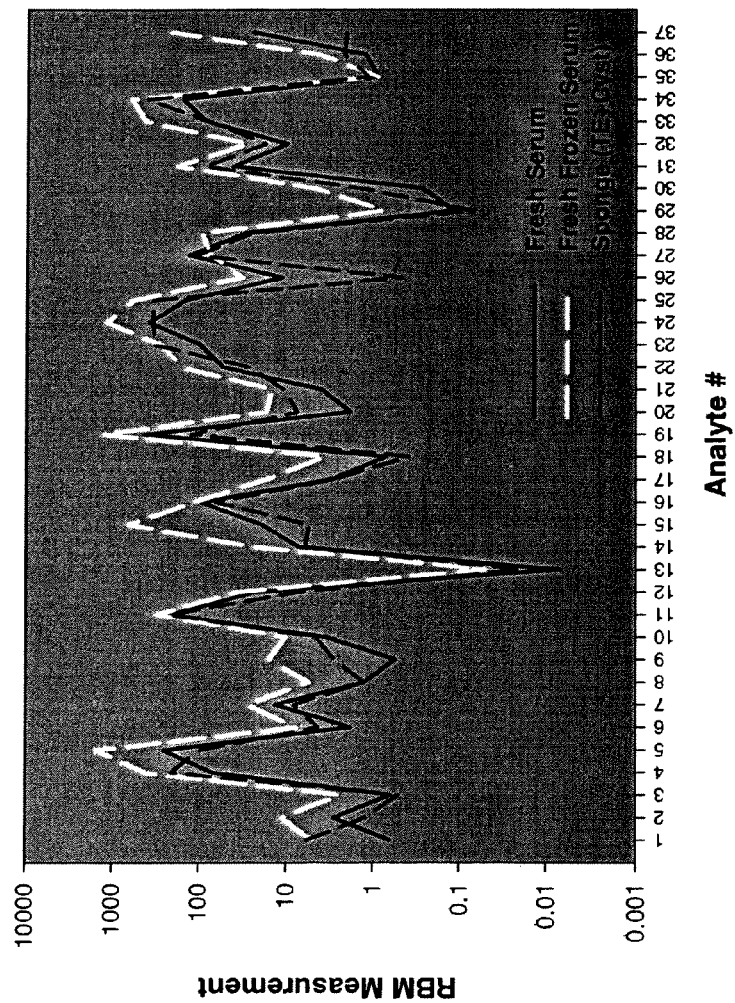
FIG. 29 is a graphical illustration of the quantity of various serum analytes stored on sponge (TE+Cysteine) at room temperature after 187 days, vs. fresh and frozen serum (see the data presented in Tables 5-7).
Figure 30:
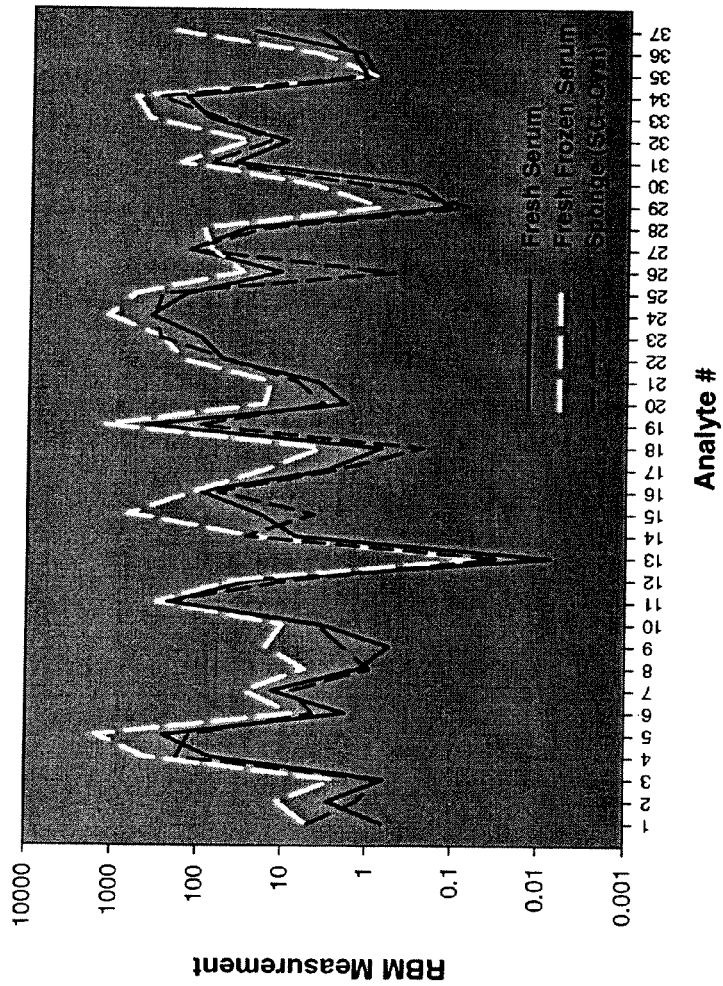
FIG. 30 is a graphical illustration of the quantity of various serum analytes stored on sponge (TE+Cysteine+NP40) at room temperature after 187 days, vs. fresh and frozen serum (see the data presented in Tables 5-7).

An exemplary storage unit is illustrated in FIGS. 2 and 3. In brief, sample can be absorbed to substrate contained in a vessel, as illustrated in FIG. 2. The sample is applied to the substrate housed in a storage unit (e.g., vessel), any moisture present reduced by drying, and the vessel is capped to store the absorbed sample. The sample can then subsequently be recovered from the substrate as illustrated in FIG. 3. In brief, the absorbed substrate is hydrated with a liquid, the substrate, in this case an elastomeric substrate is compressed one or more times with a plunger, and the liquid containing the eluted sample is recovered by aspiration of the eluate. All steps of sample absorption and elution are contained within the vessel with no need for sample handling or transfer until the eluted sample is aspirated.

The use of a plunger, as illustrated in FIGS. 2 and 3, does not require the use of a filter or similar barrier attached to the plunger in order to recover the sample eluted from the substrate in the plunger barrel. This is because the plunger has passages that allow the elution liquid expelled from the sponge, when the sponge is compressed, to accumulate in the plunger barrel. Although the illustrated plunger has multiple passages for allowing the liquid to pass into the barrel (on both the sides and on the bottom), the plunger will function in the intended manner with a single passage either on the side or on the bottom of the plunger. The top of the plunger can be configured so that it can be locked in a position in the vessel so that the sponge remains compressed while the expelled eluate is recovered. The top of vessel can be open (a hole at the top of the plunger) or openable (e.g., a thin pierceable film or removable closure) so that the elution liquid can be withdrawn from the vessel.

A storage unit comprised of a plurality of vessel containers housing each housing substrates can be designed to facilitate simple and efficient absorption of biomolecule samples and subsequent elution or recovery. For example, the use of a pre-cut sponge template can simplify storage by punching the foam onto the storage unit (e.g., a vessel or plate). The vessel container illustrated in FIGS. 2 and 3 housing the substrate eliminates the need for a centrifuge, and the container is compatible with most HPLC automated sample feeders. The vessel storage unit provides efficient sample handling that is amenable to automation, with full functionality for sample absorption and elution or recovery from substrate.

The vessel storage unit has readily apparent and inherent features. Examples of such features include the ability to absorb sample and elute/recover the absorbed sample in the same unit and without transferring the substrate from one container to another. This avoids associated problems of cross-contamination or sample identity loss. There is no need for a centrifuge or centrifugation to recover the eluted sample a simple compression of the elastomeric substrate (e.g., sponge) will be sufficient to elute or recover the sample from the substrate. The vessel is compatible with many robots that "pick and place" small tubes arrayed in a 96 well SBS format. The vessel is automation friendly. The vessel can be labeled for identification, using a conventional bar code or other system (see, for example, U.S. Patent Application Publication No. 20050026181). The vessel is cost effective as compared to a system of "punch-outs" for storing adsorbed sponges, and the associated equipment. There is also no need to punch the substrate (e.g., sponge) through a pierceable film in order to house the sponge in a storage unit.

Example 6

This example includes studies in which blood absorbed to an elutable elastomeric substrate was stored for various times and subsequently eluted, recovered and analyzed. The exemplary study employs a single step for elution of protein from absorbed polyester sponge,
Single-Step Elution and Recovery of Protein from a Blood Sample Absorbed to Sponge A large number of polyurethane (polyester) sponges (a 6 mm×5 mm cylinder) with various treatments (see below) was absorbed with a blood sample and stored at room temperature. After storage for 7, 12, 28, 55, 85, 187 and 209 days, the blood-absorbed sponge was hydrated with water (150 µl) and protein eluted from the sponge by compressing the sponge contained in a vessel with a plunger. The procedure is essentially as described in Example 4. The protein eluates recovered from sponge stored for 7, 12 (10 and 45 minute elution times), 28, 55, 85, 187 and 209 (more vigorous and longer elution) days were subsequently analyzed for protein concentration using a bicinchoninic acid (BCA) assay, which can detect protein at concentrations of 20-2,000 µg/ml, and is available as a kit (Pierce, Rockford, Ill.). These results are illustrated in Table 4.

The protein eluates recovered from sponge stored for 7, 55 and 187 days were also screened for a panel of analytes using Human MAP™ a bead array system for measuring over 175 analytes in human plasma or serum (Rules Based Medicine, abbreviated as "RBM," Austin, Tex.). This screen is a quantitative screen which detects the presence and if appropriate an approximate amount of these analytes in a sample. These results are illustrated in Tables 5 to 7 and in FIGS. 4 to 30.

Figure 34:
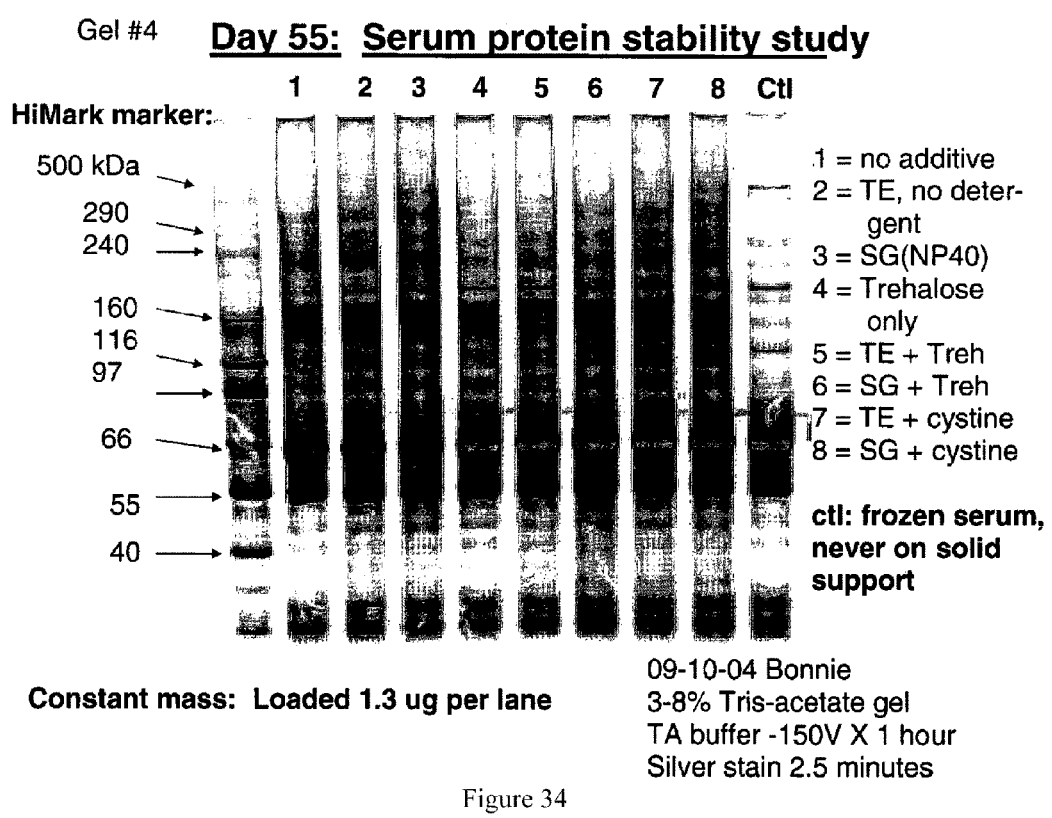
FIG. 34 is a gel electrophoresis result indicating that protein stored after 55 days using 12 sponge material was not significantly degraded.
Figure 35:
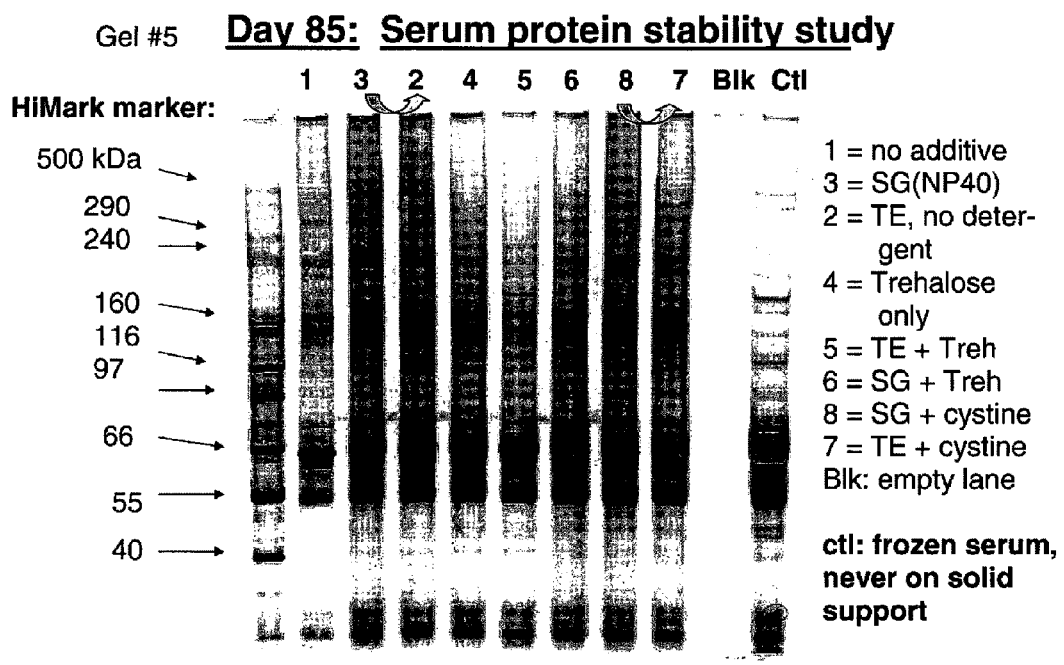
FIG. 35 is a gel electrophoresis result indicating that protein stored after 85 days using 12 sponge material was not significantly degraded.

The recovered protein eluates, from sponge stored for 55 and 85 days, were also subjected to analysis by gel electrophoresis and silver staining. The electrophoresis screen reveals the integrity of the proteins recovered from sponge, and will detect protein degradation. These results are illustrated in FIGS. 34 and 35.

For the results illustrated on Tables 5 to 7 that follow, the top row designates the treatment. For example, GV1, GV2 etc. are each shown twice on the 7 day chart, once for each sample of that particular treatment. Where the treatments are shown as GV11, GV12 and so on, that illustrates the second (55 day) results for GV1, GV2 and so on. Thus, GV11, GV11 and so on are for untreated sponge (Treatment #1); GV3, GV13 are for Treatment #3 (TE+NP40); and GV5, GV15 are for Treatment #5 (TE+Trehalose).

TABLE 4

Polyester Sponge Serum Stability Study

| smpl # | | Day 7 Conc in ug/ml | Day 12 for 10 min elute Conc in ug/ml | Day 12 for 45 min elute Conc in ug/ml | Day 28 Conc in ug/ml | Day 55 Conc in ug/ml | Day 85 Conc in ug/ml | Day 187 Conc in ug/ml | **longer & more vigorous washing for day 209 Conc in ug/ml |
|---|---|---|---|---|---|---|---|---|---|
| | Fresh control serum | 106,027 | 106,027 | 106,027 | 106,027 | 106,027 | 106,027 | 106,027 | 106,027 |
| | Frozen control serum | 107,640 | 102,350 | 102,350 | 101,587 | 103,960 | 108,734 | 112,539 | 100,445 |
| 1 | No additive | 84,424 | 89,600 | 85,200 | 33,800 | 71,400 | 62,200 | 22,636 | 52,053 |
| 2 | TE, no detergent | 100,720 | 112,800 | 108,000 | 54,400 | 56,400 | 75,600 | 49,253 | 81,358 |
| 3 | TE + NP40 (SG) | 97,770 | 114,400 | 118,000 | 103,200 | 101,900 | 103,600 | 68,507 | 77,223 |
| 4 | Trehalose only | 66,834 | 69,200 | 75,200 | 68,400 | 67,600 | 59,400 | 69,701 | 79,474 |
| 5 | TE + treh | 62,717 | 72,400 | 63,200 | 66,000 | 62,500 | 62,000 | 59,969 | 78,426 |
| 6 | SG + treh | 91,057 | 100,400 | 125,200 | 91,200 | 81,800 | 84,000 | 81,851 | 79,707 |
| 7 | TE + cystine | 80,544 | 92,800 | 85,200 | 86,800 | 73,900 | 76,600 | 64,522 | 75,110 |
| 8 | SG + cystine | 94,474 | 114,800 | 109,600 | 99,200 | 102,800 | 98,000 | 68,581 | 83,177 |

| smpl # | | Day 7 Total prot in ug | Day 12 for 10 min elute Total prot in ug | Day 12 for 45 min elute Total prot in ug | Day 28 Total prot in ug | Day 55 Total prot in ug | Day 85 Total prot in ug | Day 187 Total prot in ug | Day 209 Total prot in ug |
|---|---|---|---|---|---|---|---|---|---|
| | Fresh control serum | 15,904 | 15,904 | 15,904 | 15,904 | 15,904 | 15,904 | 15,904 | 15,904 |
| | Frozen control serum | 16,146 | 15,353 | 15,353 | 15,238 | 15,594 | 16,310 | 16,881 | 15,067 |
| 1 | No additive | 12,664 | 13,440 | 12,695 | 5,070 | 10,710 | 9,330 | 3,395 | 7,808 |
| 2 | TE, no detergent | 15,108 | 16,920 | 16,092 | 8,160 | 8,460 | 11,340 | 7,388 | 12,204 |
| 3 | TE + NP40 (SG) | 14,667 | 17,160 | 17,582 | 15,480 | 15,285 | 15,540 | 10,276 | 11,584 |
| 4 | Trehalose only | 10,025 | 10,380 | 11,205 | 10,260 | 10,140 | 8,910 | 10,455 | 11,921 |
| 5 | TE + treh | 9,408 | 10,860 | 9,417 | 9,900 | 9,375 | 9,300 | 8,995 | 11,764 |
| 6 | SG + treh | 13,659 | 15,060 | 18,655 | 13,680 | 12,270 | 12,600 | 12,278 | 11,956 |
| 7 | TE + cystine | 12,082 | 13,920 | 12,695 | 13,020 | 11,085 | 11,490 | 9,678 | 11,267 |
| 8 | SG + cystine | 14,171 | 17,220 | 16,330 | 14,880 | 15,420 | 14,700 | 10,287 | 12,477 |

TABLE 5

Day 7, RBM Analysis of Serum

| Day 7 data normalized to fresh serum value | | GV1 | GV1 | GV2 | GV2 | GV3 | GV3 | GV4 | GV4 | GV5 | GV5 | GV6 |
|---|---|---|---|---|---|---|---|---|---|---|---|---|
| Alpha-2 Macroglobulin | mg/ml | 22.22 | 21.59 | 63.17 | 59.68 | 54.60 | 56.03 | 9.92 | 11.89 | 36.35 | 36.35 | 38.41 |
| Alpha-Fetoprotein | ng/ml | 3.85 | 3.50 | 1.73 | 1.45 | 1.79 | 1.12 | 2.70 | 2.50 | 0.84 | 0.81 | 1.11 |
| Apolipoprotein A1 | mg/ml | 5.18 | 5.61 | 5.97 | 6.50 | 11.19 | 10.35 | 3.89 | 3.84 | 3.61 | 3.66 | 8.27 |
| Apolipoprotein CIII | ug/ml | 6.90 | 6.52 | 7.00 | 7.64 | 7.61 | 6.78 | 5.34 | 6.06 | 4.47 | 4.63 | 4.28 |
| Apolipoprotein H | ug/ml | 4.73 | 4.45 | 5.45 | 5.37 | 4.65 | 4.49 | 3.66 | 3.79 | 3.96 | 3.87 | 4.49 |
| Beta-2 Microglobulin | ug/ml | 5.99 | 6.21 | 7.09 | 6.98 | 6.15 | 5.88 | 4.99 | 4.86 | 4.85 | 4.63 | 5.77 |
| Brain-Derived Neurotrophic Factor | ng/ml | 1.96 | 2.12 | 1.73 | 1.69 | 1.56 | 1.57 | 1.63 | 1.71 | 1.08 | 1.16 | 1.22 |
| Complement 3 | mg/ml | 7.60 | 8.66 | 8.50 | 7.06 | 6.76 | 7.20 | 6.50 | 6.33 | 4.47 | 4.23 | 4.72 |
| C Reactive Protein | ug/ml | 20.55 | 20.91 | 24.00 | 24.00 | 21.09 | 22.55 | 17.27 | 17.13 | 14.75 | 15.60 | 20.18 |
| ENA-78 | ng/ml | 2.43 | 2.46 | 2.27 | 2.27 | 2.17 | 2.19 | 2.11 | 2.09 | 1.61 | 1.63 | 1.86 |
| Factor VII | ng/ml | 1.95 | 1.75 | 1.45 | 1.41 | 1.19 | 1.07 | 2.52 | 2.69 | 1.07 | 1.07 | 0.85 |
| Ferritin | ng/ml | 2.75 | 2.91 | 3.45 | 3.57 | 3.68 | 3.21 | 2.92 | 2.81 | 2.59 | 3.05 | 3.48 |
| Fibrinogen | mg/ml | 4.85 | 5.00 | 6.04 | 5.89 | 5.15 | 5.00 | 2.86 | 3.56 | 5.45 | 5.60 | 4.22 |
| GM-CSF | pg/ml | LOW | LOW | LOW | LOW | LOW | LOW | LOW | LOW | LOW | LOW | LOW |
| Glutathione S-Transferase | ng/ml | LOW | LOW | 0.14 | 0.11 | 0.06 | 0.05 | 0.03 | 0.02 | 0.06 | 0.05 | 0.03 |
| ICAM-1 | ng/ml | 2.31 | 2.13 | 0.71 | 0.68 | 0.63 | 0.58 | 2.31 | 2.27 | 0.58 | 0.57 | 0.51 |
| IgA | mg/ml | 4.42 | 4.83 | 6.06 | 5.77 | 4.76 | 4.64 | 4.23 | 4.20 | 4.10 | 3.72 | 4.70 |
| IgM | mg/ml | 5.04 | 5.48 | 6.25 | 6.11 | 5.11 | 5.08 | 4.14 | 3.80 | 4.23 | 4.24 | 4.58 |
| IL-16 | pg/ml | 2.79 | 2.77 | 1.68 | 0.67 | 0.31 | 0.32 | 2.38 | 2.32 | 0.73 | 0.69 | 0.63 |
| Insulin | uIU/ml | 16.12 | 15.41 | 4.35 | 4.23 | 2.81 | 2.77 | 13.44 | 13.17 | 3.11 | 3.13 | 1.82 |
| Leptin | ng/ml | 3.91 | 3.66 | 3.27 | 3.00 | 2.75 | 2.60 | 2.44 | 2.29 | 1.65 | 1.58 | 1.82 |
| Lipoprotein (a) | ug/ml | 0.41 | 0.39 | 0.22 | 0.19 | 0.24 | 0.22 | 0.86 | 0.87 | 0.52 | 0.53 | 0.17 |
| MCP-1 | pg/ml | 5.96 | 5.79 | 4.48 | 4.57 | 3.48 | 3.40 | 4.73 | 4.56 | 3.21 | 3.42 | 2.37 |
| MDC | pg/ml | 2.30 | 2.34 | 2.24 | 2.11 | 2.32 | 2.26 | 1.27 | 1.26 | 0.95 | 0.94 | 1.33 |
| MIP-1beta | pg/ml | 4.05 | 3.88 | 2.22 | 2.39 | 1.93 | 1.79 | 3.27 | 2.99 | 1.70 | 1.69 | 1.43 |
| MMP-3 | ng/ml | 5.90 | 5.07 | LOW | LOW | LOW | LOW | 4.35 | 4.12 | LOW | LOW | LOW |
| MMP-9 | ng/ml | 0.40 | 0.54 | 6.59 | 6.05 | 10.63 | 10.11 | 0.63 | 0.19 | 7.73 | 7.58 | 11.67 |
| Myglobin | ng/ml | 4.06 | 3.06 | 1.63 | 1.73 | 2.33 | 1.87 | 2.12 | 1.66 | 0.96 | 0.92 | 1.23 |
| Prostatic Acid Phosphatase | ng/ml | LOW | LOW | LOW | LOW | LOW | LOW | 0.23 | LOW | LOW | LOW | LOW |
| Prostate Specific Antigen, Free | ng/ml | 3.96 | 3.79 | 4.36 | 3.89 | 3.33 | 3.01 | 2.92 | 2.48 | 1.99 | 1.96 | 2.08 |
| RANTES | ng/ml | 4.29 | 4.29 | 5.15 | 5.53 | 5.24 | 4.65 | 4.51 | 4.24 | 4.53 | 4.05 | 6.13 |
| Serum Amyloid P | ug/ml | 2.97 | 2.70 | 3.59 | 3.65 | 2.87 | 3.41 | 2.29 | 2.58 | 2.76 | 2.52 | 3.44 |
| SGOT | ug/ml | 0.98 | 0.89 | 2.50 | 2.70 | 3.01 | 3.25 | 1.00 | 1.11 | 3.33 | 3.35 | 4.62 |
| Thyroxine Binding Globulin | ug/ml | 5.68 | 5.67 | 6.58 | 7.21 | 5.57 | 5.52 | 4.86 | 4.82 | 4.50 | 4.25 | 5.37 |
| TIMP-1 | ng/ml | 3.78 | 3.95 | 4.84 | 4.76 | 4.18 | 4.45 | 3.45 | 3.65 | 3.61 | 3.50 | 3.89 |
| Thrombopoietin | ng/ml | LOW | LOW | LOW | LOW | LOW | LOW | LOW | LOW | LOW | LOW | LOW |
| Thyroid Stimulating Hormone | uIU/ml | 4.13 | 3.77 | 2.47 | 2.43 | 1.97 | 1.77 | 2.29 | 2.15 | 1.35 | 1.24 | 1.01 |
| von Willebrand Factor | ug/ml | 6.21 | 7.41 | 7.33 | 7.58 | 5.77 | 6.37 | 5.61 | 5.29 | 5.81 | 5.77 | 6.81 |

| Day 7 data normalized to fresh serum value | | GV6 | GV7 | GV7 | GV8 | GV8 | Frozen cont 1 | Frozen cont 2 | Fresh serum actual val | idd |
|---|---|---|---|---|---|---|---|---|---|---|
| Alpha-2 Macroglobulin | mg/ml | 38.41 | 53.65 | 54.29 | 45.24 | 45.87 | 1.55 | 1.52 | 0.63 | 0.03 |
| Alpha-Fetoprotein | ng/ml | 0.85 | 1.50 | 1.36 | 1.44 | 1.12 | 1.61 | 5.48 | 2.83 | 0.94 |
| Apolipoprotein A1 | mg/ml | 8.65 | 6.32 | 5.39 | 9.84 | 9.85 | 1.27 | 1.23 | 0.62 | 0.05 |
| Apolipoprotein CIII | ug/ml | 4.77 | 8.40 | 6.16 | 5.50 | 6.96 | 1.57 | 1.20 | 68.70 | 5.92 |
| Apolipoprotein H | ug/ml | 4.61 | 3.70 | 3.59 | 4.25 | 4.02 | 1.20 | 1.13 | 251.50 | 7.36 |
| Beta-2 Microglobulin | ug/ml | 5.18 | 6.32 | 6.43 | 5.47 | 5.10 | 1.10 | 0.99 | 1.82 | 0.05 |
| Brain-Derived Neurotrophic Factor | ng/ml | 1.16 | 1.99 | 1.96 | 1.74 | 1.77 | 1.09 | 1.01 | 13.40 | 0.03 |
| Complement 3 | mg/ml | 4.31 | 6.46 | 6.37 | 7.79 | 6.67 | 1.28 | 1.06 | 1.27 | 0.00 |
| C Reactive Protein | ug/ml | 17.85 | 23.27 | 21.09 | 17.95 | 17.09 | 4.96 | 5.02 | 0.55 | 0.00 |
| ENA-78 | ng/ml | 1.89 | 2.34 | 2.35 | 2.30 | 2.33 | 0.96 | 0.94 | 3.48 | 0.06 |
| Factor VII | ng/ml | 0.78 | 1.16 | 1.10 | 0.98 | 1.08 | 1.12 | 1.09 | 216.00 | 0.87 |
| Ferritin | ng/ml | 2.85 | 3.23 | 2.99 | 3.53 | 1.36 | 1.05 | 23.05 | 3.75 |
| Fibrinogen | mg/ml | 4.53 | 5.45 | 4.85 | 4.22 | 5.00 | LOW | LOW | 0.01 | 0.01 |
| GM-CSF | pg/ml | LOW | LOW | LOW | LOW | LOW | LOW | LOW | 7.22 | 6.11 |
| Glutathione S-Transferase | ng/ml | 0.02 | 0.08 | 0.08 | 0.03 | 0.04 | 2.01 | 1.18 | 19.20 | 0.86 |
| ICAM-1 | ng/ml | 0.52 | 0.66 | 0.65 | 0.58 | 0.57 | 1.06 | 1.07 | 96.60 | 4.00 |
| IgA | mg/ml | 4.61 | 5.77 | 4.48 | 4.61 | 4.57 | 1.23 | 1.09 | 3.17 | 0.02 |
| IgM | mg/ml | 4.52 | 5.72 | 5.62 | 5.25 | 5.11 | 1.21 | 1.06 | 0.71 | 0.02 |
| IL-16 | pg/ml | 0.65 | 0.91 | 0.88 | 0.56 | 0.54 | 0.95 | 0.86 | 440.50 | 70.10 |
| Insulin | uIU/ml | 2.05 | 3.16 | 2.97 | 1.90 | 1.81 | 3.92 | 3.89 | 1.83 | 1.52 |
| Leptin | ng/ml | 1.83 | 2.75 | 2.72 | 2.31 | 2.50 | 1.08 | 1.05 | 4.04 | 0.13 |
| Lipoprotein (a) | ug/ml | 0.17 | 0.18 | 0.17 | 0.23 | 0.23 | 1.24 | 1.15 | 53.85 | 0.15 |
| MCP-1 | pg/ml | 2.31 | 4.84 | 4.49 | 4.11 | 3.78 | 0.80 | 0.78 | 97.85 | 41.10 |
| MDC | pg/ml | 1.46 | 2.24 | 2.13 | 2.13 | 2.12 | 1.11 | 1.06 | 385.00 | 17.40 |
| MIP-1beta | pg/ml | 1.51 | 2.55 | 2.44 | 1.87 | 1.83 | 0.74 | 0.67 | 145.00 | 40.90 |
| MMP-3 | ng/ml | LOW | LOW | LOW | LOW | LOW | 0.97 | 1.01 | 11.30 | 0.29 |
| MMP-9 | ng/ml | 11.60 | 1.70 | 1.61 | 3.29 | 3.43 | 1.51 | 0.91 | 134.50 | 79.10 |
| Myglobin | ng/ml | 1.22 | 1.89 | 1.68 | 2.28 | 2.48 | 1.11 | 1.05 | 29.80 | 0.12 |
| Prostatic Acid Phosphatase | ng/ml | LOW | LOW | LOW | LOW | LOW | 0.95 | 0.87 | 0.12 | 0.07 |

TABLE 5-continued

Day 7, RBM Analysis of Serum

| | | | | | | | | | | |
|---|---|---|---|---|---|---|---|---|---|---|
| Prostate Specific Antigen, Free | ng/ml | 2.04 | 3.53 | 3.39 | 3.21 | 3.15 | 1.06 | 1.19 | 0.28 | 0.18 |
| RANTES | ng/ml | 5.34 | 6.67 | 6.13 | 5.27 | 5.53 | 1.15 | 1.06 | 41.95 | 0.32 |
| Serum Amyloid P | ug/ml | 3.62 | 2.63 | 2.70 | 3.44 | 3.87 | 1.16 | 1.09 | 32.85 | 0.01 |
| SGOT | ug/ml | 4.90 | 2.90 | 3.47 | 3.51 | 3.35 | 1.13 | 1.11 | 10.05 | 4.99 |
| Thyroxine Binding Globulin | ug/ml | 5.04 | 5.24 | 4.59 | 3.84 | 3.75 | 1.15 | 1.17 | 84.80 | 0.05 |
| TIMP-1 | ng/ml | 3.90 | 4.32 | 4.14 | 3.86 | 4.08 | 1.15 | 1.07 | 159.00 | 7.90 |
| Thrombopoietin | ng/ml | LOW | LOW | LOW | LOW | LOW | LOW | LOW | 0.92 | 0.57 |
| Thyroid Stimulating Hormone | uIU/ml | 1.04 | 2.20 | 2.28 | 1.62 | 1.76 | 1.02 | 1.01 | 1.27 | 0.07 |
| von Willebrand Factor | ug/ml | 5.69 | 5.01 | 4.57 | 5.01 | 5.09 | 1.76 | 1.63 | 24.95 | 0.51 |

Key
GV1 = NOTHING
GV2 = TE
GV3 = TE + NP40 (SG)
GV4 = TREH
GV5 = TE + TREH
GV6 = SG + TREH
GV7 = TE + CYST
GV8 = SG + CYST

TABLE 6

Day 55, RBM Analysis of Serum

| Day 55 data normalized to fresh serum value | | GV11 | GV11 | GV12 | GV12 | GV13 | GV13 | GV14 | GV14 | GV15 | GV15 | GV16 |
|---|---|---|---|---|---|---|---|---|---|---|---|---|
| Alpha-2 Macroglobulin | mg/ml | 21.11 | 23.49 | 28.73 | 28.89 | 52.54 | 54.76 | 36.67 | 34.76 | 43.49 | 44.29 | 54.60 |
| Alpha-Fetoprotein | ng/ml | 2.77 | 2.71 | LOW | LOW | 0.63 | 0.64 | 2.03 | 1.90 | LOW | LOW | 0.45 |
| Apolipoprotein A1 | mg/ml | 1.94 | 2.00 | 2.26 | 1.98 | 4.92 | 5.23 | 1.79 | 1.92 | 2.27 | 2.11 | 3.31 |
| Apolipoprotein CIII | ug/ml | 4.73 | 4.60 | 4.40 | 4.02 | 5.52 | 5.84 | 4.88 | 4.53 | 4.69 | 5.15 | 4.37 |
| Apolipoprotein H | ug/ml | 1.71 | 1.64 | 0.95 | 0.96 | 1.53 | 1.43 | 1.71 | 1.75 | 1.71 | 1.65 | 1.50 |
| Beta-2 Microglobulin | ug/ml | 4.16 | 4.07 | 3.04 | 3.07 | 4.65 | 4.66 | 4.15 | 4.12 | 3.97 | 3.84 | 3.88 |
| Brain-Derived Neurotrophic Factor | ng/ml | 1.13 | 1.19 | 0.68 | 0.72 | 1.16 | 1.10 | 1.28 | 1.27 | 0.80 | 0.78 | 0.81 |
| Complement 3 | mg/ml | 2.50 | 2.40 | 2.35 | 2.57 | 3.10 | 3.21 | 3.31 | 3.31 | 3.46 | 3.77 | 3.28 |
| C Reactive Protein | ug/ml | 9.53 | 9.07 | 8.56 | 8.45 | 11.60 | 11.27 | 12.93 | 13.05 | 13.44 | 13.33 | 12.11 |
| ENA-78 | ng/ml | 1.94 | 2.03 | 1.35 | 1.36 | 1.86 | 1.87 | 1.89 | 1.80 | 1.45 | 1.45 | 1.45 |
| Factor VII | ng/ml | 1.42 | 1.62 | 0.88 | 0.88 | 0.99 | 0.98 | 1.29 | 1.31 | 0.86 | 0.82 | 0.80 |
| Ferritin | ng/ml | 0.87 | 1.03 | 1.24 | 1.15 | 1.68 | 1.42 | 1.39 | 1.33 | 1.87 | 1.70 | 1.79 |
| Fibrinogen | mg/ml | 2.51 | 2.25 | 2.25 | 1.47 | 2.78 | 2.51 | 2.78 | 1.99 | 3.32 | 3.18 | 2.91 |
| GM-CSF | pg/ml | LOW | LOW | LOW | LOW | LOW | LOW | LOW | LOW | LOW | LOW | LOW |
| Glutathione S-Transferase | ng/ml | LOW | LOW | 0.07 | 0.09 | 0.06 | LOW | LOW | LOW | 0.08 | 0.08 | LOW |
| ICAM-1 | ng/ml | 1.51 | 1.65 | 0.46 | 0.48 | 0.59 | 0.59 | 0.97 | 0.97 | 0.41 | 0.42 | 0.51 |
| IgA | mg/ml | 2.05 | 1.82 | 1.63 | 1.65 | 2.15 | 1.94 | 3.15 | 3.28 | 2.59 | 2.79 | 2.54 |
| IgM | mg/ml | 2.03 | 1.94 | 2.03 | 1.82 | 2.03 | 2.21 | 2.94 | 3.20 | 3.08 | 3.03 | 2.61 |
| IL-16 | pg/ml | 1.91 | 1.99 | LOW | LOW | LOW | LOW | 1.90 | 1.89 | 0.35 | 0.31 | LOW |
| Insulin | uIU/ml | 16.28 | 16.78 | 2.28 | 2.61 | 2.26 | 2.52 | 12.62 | 12.90 | 2.38 | 2.21 | 1.19 |
| Leptin | ng/ml | 3.56 | 3.69 | 2.29 | 2.45 | 2.38 | 2.31 | 2.22 | 2.23 | 1.61 | 1.61 | 1.46 |
| Lipoprotein (a) | ug/ml | 0.35 | 0.38 | 0.15 | 0.17 | 0.20 | 0.22 | 0.16 | 0.18 | 0.12 | 0.14 | 0.20 |
| MCP-1 | pg/ml | 4.59 | 4.85 | 2.83 | 2.85 | 3.69 | 3.56 | 4.80 | 4.55 | 3.29 | 2.94 | 2.62 |
| MDC | pg/ml | 1.46 | 1.54 | 1.09 | 1.03 | 1.92 | 1.86 | 1.20 | 1.17 | 0.85 | 0.83 | 1.06 |
| MIP-1beta | pg/ml | 3.78 | 4.14 | 1.37 | 1.30 | 2.02 | 1.98 | 3.63 | 3.51 | 1.59 | 1.57 | 1.48 |
| MMP-3 | ng/ml | 3.01 | 3.08 | LOW | LOW | LOW | LOW | 2.58 | 2.62 | LOW | LOW | LOW |
| MMP-9 | ng/ml | 0.83 | 1.06 | 2.85 | 3.10 | 5.76 | 5.71 | LOW | LOW | 4.88 | 4.77 | 8.33 |
| Myglobin | ng/ml | 1.74 | 2.30 | 1.09 | 1.17 | 0.90 | 0.93 | 2.22 | 2.88 | 1.38 | 1.39 | 0.94 |
| Prostatic Acid Phosphatase | ng/ml | LOW | LOW | LOW | LOW | LOW | LOW | LOW | LOW | LOW | LOW | LOW |
| Prostate Specific Antigen, Free | ng/ml | 3.47 | 3.86 | 3.89 | 4.11 | 4.93 | 4.75 | 1.73 | 1.86 | 2.36 | 2.21 | 2.67 |
| RANTES | ng/ml | 2.84 | 2.91 | 3.00 | 2.84 | 4.46 | 4.05 | 3.96 | 4.15 | 4.65 | 4.10 | 4.34 |
| Serum Amyloid P | ug/ml | 1.36 | 1.39 | 1.81 | 1.80 | 1.99 | 1.72 | 1.96 | 1.84 | 2.50 | 2.39 | 2.21 |
| SGOT | ug/ml | LOW | LOW | 2.06 | 2.44 | 2.19 | 2.46 | 1.23 | 0.83 | 3.02 | 3.02 | 3.25 |
| Thyroxine Binding Globulin | ug/ml | 2.85 | 2.85 | 1.78 | 1.79 | 2.46 | 2.33 | 3.24 | 3.14 | 2.78 | 2.72 | 2.36 |
| TIMP-1 | ng/ml | 2.97 | 3.35 | 2.76 | 2.67 | 3.92 | 3.86 | 3.32 | 3.40 | 3.15 | 3.27 | 3.08 |
| Thrombopoietin | ng/ml | LOW | LOW | LOW | LOW | LOW | LOW | LOW | LOW | LOW | LOW | LOW |
| Thyroid Stimulating Hormone | uIU/ml | 2.90 | 3.20 | 1.76 | 1.83 | 1.91 | 2.02 | 1.84 | 2.05 | 1.24 | 1.24 | 1.12 |
| von Willebrand Factor | ug/ml | 0.82 | 0.83 | 0.75 | 0.65 | 0.71 | 0.66 | 1.33 | 1.31 | 1.39 | 1.49 | 1.31 |

| Day 55 data normalized to fresh serum value | | GV16 | GV17 | GV17 | GV18 | GV18 | Frozen cont 1 | Frozen cont 2 | Fresh serum actual val | idd |
|---|---|---|---|---|---|---|---|---|---|---|
| Alpha-2 Macroglobulin | mg/ml | 48.73 | 39.68 | 34.76 | 44.13 | 45.08 | 1.01 | 1.04 | 0.63 | 0.03 |
| Alpha-Fetoprotein | ng/ml | LOW | 0.83 | 0.80 | 0.47 | 0.36 | 0.77 | 1.30 | 2.83 | 0.94 |

TABLE 6-continued

Day 55, RBM Analysis of Serum

| | | | | | | | | | | | |
|---|---|---|---|---|---|---|---|---|---|---|---|
| Apolipoprotein A1 | mg/ml | 3.47 | 3.03 | 3.13 | 4.85 | 4.82 | 0.95 | 0.91 | 0.62 | 0.05 |
| Apolipoprotein CIII | ug/ml | 4.51 | 5.25 | 5.37 | 5.31 | 5.56 | 0.89 | 0.78 | 68.70 | 5.92 |
| Apolipoprotein H | ug/ml | 1.47 | 1.06 | 1.03 | 1.16 | 1.11 | 1.05 | 1.10 | 251.50 | 7.36 |
| Beta-2 Microglobulin | ug/ml | 3.66 | 4.51 | 4.24 | 4.34 | 4.23 | 0.88 | 1.02 | 1.82 | 0.05 |
| Brain-Derived Neurotrophic Factor | ng/ml | 0.82 | 1.31 | 1.23 | 1.26 | 1.32 | 1.04 | 1.10 | 13.40 | 0.03 |
| Complement 3 | mg/ml | 3.58 | 3.00 | 3.57 | 2.56 | 3.01 | 1.09 | 1.20 | 1.27 | 0.00 |
| C Reactive Protein | ug/ml | 11.16 | 13.20 | 11.18 | 10.93 | 11.65 | 3.60 | 4.13 | 0.55 | 0.00 |
| ENA-78 | ng/ml | 1.44 | 2.03 | 2.01 | 1.87 | 1.91 | 1.03 | 1.10 | 3.48 | 0.06 |
| Factor VII | ng/ml | 0.88 | 1.03 | 0.99 | 1.05 | 0.99 | 0.81 | 0.99 | 216.00 | 0.87 |
| Ferritin | ng/ml | 1.70 | 1.57 | 1.87 | 1.84 | 1.50 | 0.85 | 0.81 | 23.05 | 3.75 |
| Fibrinogen | mg/ml | 3.59 | 2.78 | 3.59 | 2.78 | 2.51 | 1.00 | 1.00 | 0.01 | 0.01 |
| GM-CSF | pg/ml | LOW | LOW | LOW | LOW | LOW | LOW | LOW | 7.22 | 6.11 |
| Glutathione S-Transferase | ng/ml | LOW | 0.08 | 0.08 | LOW | LOW | 0.86 | 1.21 | 19.20 | 0.86 |
| ICAM-1 | ng/ml | 0.52 | 0.64 | 0.64 | 0.66 | 0.65 | 0.69 | 0.93 | 96.60 | 4.00 |
| IgA | mg/ml | 2.87 | 2.42 | 2.46 | 2.32 | 2.11 | 0.91 | 0.98 | 3.17 | 0.02 |
| IgM | mg/ml | 2.68 | 2.68 | 2.69 | 2.14 | 2.11 | 1.01 | 0.99 | 0.71 | 0.02 |
| IL-16 | pg/ml | LOW | 0.42 | 0.40 | 0.24 | 0.28 | 1.09 | 1.15 | 440.50 | 70.10 |
| Insulin | uIU/ml | 1.06 | 3.37 | 3.10 | 1.74 | 1.77 | 3.80 | 4.22 | 1.83 | 1.52 |
| Leptin | ng/ml | 1.49 | 3.24 | 3.27 | 2.45 | 2.42 | 0.97 | 1.22 | 4.04 | 0.13 |
| Lipoprotein (a) | ug/ml | 0.21 | 0.24 | 0.22 | 0.29 | 0.30 | 0.73 | 1.05 | 53.85 | 0.15 |
| MCP-1 | pg/ml | 2.62 | 4.80 | 4.61 | 4.84 | 4.83 | 0.96 | 1.05 | 97.85 | 41.10 |
| MDC | pg/ml | 1.03 | 1.59 | 1.61 | 1.68 | 1.71 | 1.16 | 1.29 | 385.00 | 17.40 |
| MIP-1beta | pg/ml | 1.50 | 2.48 | 2.47 | 2.21 | 1.99 | 1.04 | 0.99 | 145.00 | 40.90 |
| MMP-3 | ng/ml | LOW | LOW | LOW | LOW | LOW | 0.91 | 1.27 | 11.30 | 0.29 |
| MMP-9 | ng/ml | 8.33 | 2.39 | 2.15 | 2.67 | 2.78 | 1.87 | 2.01 | 134.50 | 79.10 |
| Myglobin | ng/ml | 1.00 | 2.26 | 2.23 | 1.32 | 1.38 | 0.94 | 1.00 | 29.80 | 0.12 |
| Prostatic Acid Phosphatase | ng/ml | LOW | LOW | LOW | LOW | LOW | LOW | LOW | 0.12 | 0.07 |
| Prostate Specific Antigen, Free | ng/ml | 2.84 | 5.68 | 5.50 | 5.93 | 5.86 | 0.81 | 1.37 | 0.28 | 0.18 |
| RANTES | ng/ml | 4.65 | 4.77 | 4.15 | 4.74 | 4.41 | 0.95 | 1.03 | 41.95 | 0.32 |
| Serum Amyloid P | ug/ml | 2.44 | 2.30 | 1.98 | 1.97 | 2.00 | 0.95 | 1.03 | 32.85 | 0.01 |
| SGOT | ug/ml | 3.74 | 1.77 | 1.93 | 2.13 | 2.34 | 0.94 | 1.03 | 10.05 | 4.99 |
| Thyroxine Binding Globulin | ug/ml | 2.31 | 2.11 | 1.97 | 1.89 | 1.90 | 0.99 | 1.11 | 84.80 | 0.05 |
| TIMP-1 | ng/ml | 3.19 | 3.70 | 3.94 | 3.61 | 3.84 | 0.96 | 1.03 | 159.00 | 7.90 |
| Thrombopoietin | ng/ml | LOW | LOW | LOW | LOW | LOW | LOW | LOW | 0.92 | 0.57 |
| Thyroid Stimulating Hormone | uIU/ml | 1.18 | 2.73 | 2.62 | 2.20 | 2.18 | 0.96 | 1.18 | 1.27 | 0.07 |
| von Willebrand Factor | ug/ml | 1.34 | 0.59 | 0.58 | 0.68 | 0.69 | 0.92 | 1.06 | 24.95 | 0.51 |

Key
GV1 = NOTHING
GV2 = TE
GV3 = TE + NP40 (SG)
GV4 = TREH
GV5 = TE + TREH
GV6 = SG + TREH
GV7 = TE + CYST
GV8 = SG + CYST

TABLE 7

Difference RBM: Day 55 vs Day 7

| Day 55 data div by day 7 data | GV1 | GV1 | GV2 | GV2 | GV3 | GV3 | GV4 | GV4 | GV5 | GV5 |
|---|---|---|---|---|---|---|---|---|---|---|
| Alpha-2 Macroglobulin | 0.95 | 1.09 | 0.45 | 0.48 | 0.96 | 0.98 | 3.70 | 2.92 | 1.20 | 1.22 |
| Alpha-Fetoprotein | 0.72 | 0.77 | 1.00 | 0.35 | 0.57 | 0.75 | 0.76 | 1.00 | 1.00 | |
| Apolipoprotein A1 | 0.37 | 0.36 | 0.38 | 0.31 | 0.44 | 0.50 | 0.46 | 0.50 | 0.63 | 0.58 |
| Apolipoprotein CIII | 0.69 | 0.71 | 0.63 | 0.53 | 0.72 | 0.86 | 0.91 | 0.75 | 1.05 | 1.11 |
| Apolipoprotein H | 0.36 | 0.37 | 0.17 | 0.18 | 0.33 | 0.32 | 0.47 | 0.46 | 0.43 | 0.43 |
| Beta-2 Microglobulin | 0.69 | 0.65 | 0.43 | 0.44 | 0.76 | 0.79 | 0.83 | 0.85 | 0.82 | 0.83 |
| Brain-Derived Neurotrophic Factor | 0.58 | 0.56 | 0.39 | 0.43 | 0.74 | 0.70 | 0.79 | 0.74 | 0.74 | 0.68 |
| Complement 3 | 0.33 | 0.28 | 0.28 | 0.36 | 0.46 | 0.45 | 0.51 | 0.52 | 0.77 | 0.89 |
| C Reactive Protein | 0.46 | 0.43 | 0.36 | 0.35 | 0.55 | 0.50 | 0.75 | 0.76 | 0.91 | 0.85 |
| ENA-78 | 0.80 | 0.82 | 0.59 | 0.60 | 0.85 | 0.85 | 0.89 | 0.86 | 0.90 | 0.89 |
| Factor VII | 0.73 | 0.93 | 0.60 | 0.62 | 0.83 | 0.92 | 0.51 | 0.49 | 0.80 | 0.76 |
| Ferritin | 0.32 | 0.35 | 0.36 | 0.32 | 0.46 | 0.44 | 0.48 | 0.47 | 0.72 | 0.56 |
| Fibrinogen | 0.52 | 0.45 | 0.37 | 0.25 | 0.54 | 0.50 | 0.97 | 0.56 | 0.61 | 0.57 |
| GM-CSF | 1.00 | 1.00 | 1.00 | 1.00 | 1.00 | 1.00 | 1.00 | 1.00 | 1.00 | 1.00 |
| Glutathione S-Transferase | 1.00 | 1.00 | 0.50 | 0.84 | 0.94 | 1.00 | 1.00 | 1.00 | 1.24 | 1.63 |
| ICAM-1 | 0.65 | 0.77 | 0.65 | 0.70 | 0.95 | 1.01 | 0.42 | 0.43 | 0.70 | 0.73 |
| IgA | 0.46 | 0.38 | 0.27 | 0.29 | 0.45 | 0.42 | 0.75 | 0.78 | 0.63 | 0.75 |
| IgM | 0.40 | 0.35 | 0.32 | 0.30 | 0.40 | 0.43 | 0.71 | 0.84 | 0.73 | 0.71 |

TABLE 7-continued

| Difference RBM: Day 55 vs Day 7 | | | | | | | | | | |
|---|---|---|---|---|---|---|---|---|---|---|
| IL-16 | 0.68 | 0.72 | 1.00 | 1.00 | 1.00 | 1.00 | 0.80 | 0.82 | 0.48 | 0.44 |
| Insulin | 1.01 | 1.09 | 0.53 | 0.62 | 0.81 | 0.91 | 0.94 | 0.98 | 0.76 | 0.71 |
| Leptin | 0.91 | 1.01 | 0.70 | 0.82 | 0.84 | 0.92 | 0.91 | 0.98 | 0.97 | 1.02 |
| Lipoprotein (a) | 0.85 | 0.99 | 0.71 | 0.91 | 0.84 | 0.98 | 0.19 | 0.20 | 0.23 | 0.25 |
| MCP-1 | 0.77 | 0.84 | 0.63 | 0.62 | 1.06 | 1.05 | 1.02 | 1.00 | 1.03 | 0.86 |
| MDC | 0.63 | 0.66 | 0.49 | 0.49 | 0.83 | 0.83 | 0.95 | 0.93 | 0.89 | 0.89 |
| MIP-1beta | 0.93 | 1.07 | 0.62 | 0.54 | 1.05 | 1.11 | 1.11 | 1.17 | 0.93 | 0.93 |
| MMP-3 | 0.51 | 0.61 | 1.00 | 1.00 | 1.00 | 1.00 | 0.59 | 0.64 | 1.00 | 1.00 |
| MMP-9 | 2.09 | 1.96 | 0.43 | 0.51 | 0.54 | 0.56 | 1.00 | 1.00 | 0.63 | 0.63 |
| Myglobin | 0.43 | 0.75 | 0.67 | 0.67 | 0.38 | 0.49 | 1.05 | 1.74 | 1.44 | 1.51 |
| Prostatic Acid Phosphatase | 1.00 | 1.00 | 1.00 | 1.00 | 1.00 | 1.00 | 1.00 | 1.00 | 1.00 | 1.00 |
| Prostate Specific Antigen, Free | 0.87 | 1.02 | 0.89 | 1.06 | 1.48 | 1.58 | 0.59 | 0.75 | 1.19 | 1.13 |
| RANTES | 0.66 | 0.68 | 0.58 | 0.51 | 0.85 | 0.87 | 0.88 | 0.98 | 1.03 | 1.01 |
| Serum Amyloid P | 0.46 | 0.52 | 0.50 | 0.49 | 0.69 | 0.50 | 0.86 | 0.71 | 0.91 | 0.95 |
| SGOT | 1.00 | 1.00 | 0.82 | 0.90 | 0.73 | 0.76 | 1.23 | 0.74 | 0.91 | 0.90 |
| Thyroxine Binding Globulin | 0.50 | 0.50 | 0.27 | 0.25 | 0.44 | 0.42 | 0.67 | 0.65 | 0.62 | 0.64 |
| TIMP-1 | 0.79 | 0.85 | 0.57 | 0.56 | 0.94 | 0.87 | 0.96 | 0.93 | 0.87 | 0.94 |
| Thrombopoietin | 1.00 | 1.00 | 1.00 | 1.00 | 1.00 | 1.00 | 1.00 | 1.00 | 1.00 | 1.00 |
| Thyroid Stimulating Hormone | 0.70 | 0.85 | 0.71 | 0.76 | 0.97 | 1.14 | 0.80 | 0.95 | 0.92 | 1.00 |
| von Willebrand Factor | 0.13 | 0.11 | 0.10 | 0.09 | 0.12 | 0.10 | 0.24 | 0.25 | 0.24 | 0.26 |

| Day 55 data div by day 7 data | GV6 | GV6 | GV7 | GV7 | GV8 | GV8 | Frozen cont 1 | Frozen cont 2 |
|---|---|---|---|---|---|---|---|---|
| Alpha-2 Macroglobulin | 1.42 | 1.27 | 0.74 | 0.64 | 0.98 | 0.98 | 0.65 | 0.68 |
| Alpha-Fetoprotein | 0.40 | 1.00 | 0.55 | 0.59 | 0.32 | 0.32 | 0.48 | 0.24 |
| Apolipoprotein A1 | 0.40 | 0.40 | 0.48 | 0.58 | 0.49 | 0.49 | 0.74 | 0.74 |
| Apolipoprotein CIII | 1.02 | 0.95 | 0.63 | 0.87 | 0.97 | 0.80 | 0.56 | 0.65 |
| Apolipoprotein H | 0.33 | 0.32 | 0.29 | 0.29 | 0.27 | 0.28 | 0.88 | 0.97 |
| Beta-2 Microglobulin | 0.67 | 0.71 | 0.71 | 0.66 | 0.79 | 0.83 | 0.81 | 1.03 |
| Brain-Derived Neurotrophic Factor | 0.66 | 0.71 | 0.66 | 0.63 | 0.73 | 0.75 | 0.96 | 1.09 |
| Complement 3 | 0.69 | 0.83 | 0.46 | 0.56 | 0.33 | 0.45 | 0.85 | 1.13 |
| C Reactive Protein | 0.60 | 0.63 | 0.57 | 0.53 | 0.61 | 0.68 | 0.73 | 0.82 |
| ENA-78 | 0.78 | 0.76 | 0.87 | 0.86 | 0.81 | 0.82 | 1.07 | 1.17 |
| Factor VII | 0.94 | 1.14 | 0.89 | 0.89 | 1.07 | 0.91 | 0.73 | 0.91 |
| Ferritin | 0.51 | 0.59 | 0.49 | 0.55 | 0.62 | 0.42 | 0.62 | 0.77 |
| Fibrinogen | 0.69 | 0.79 | 0.51 | 0.74 | 0.66 | 0.50 | 1.00 | 1.00 |
| GM-CSF | 1.00 | 1.00 | 1.00 | 1.00 | 1.00 | 1.00 | 1.00 | 1.00 |
| Glutathione S-Transferase | 1.00 | 1.00 | 1.03 | 0.99 | 1.00 | 1.00 | 0.43 | 1.02 |
| ICAM-1 | 0.98 | 1.00 | 0.97 | 0.99 | 1.14 | 1.14 | 0.65 | 0.87 |
| IgA | 0.54 | 0.62 | 0.42 | 0.55 | 0.50 | 0.46 | 0.74 | 0.90 |
| IgM | 0.57 | 0.59 | 0.47 | 0.48 | 0.41 | 0.41 | 0.84 | 0.93 |
| IL-16 | 1.00 | 1.00 | 0.46 | 0.46 | 0.42 | 0.52 | 1.15 | 1.33 |
| Insulin | 0.65 | 0.52 | 1.07 | 1.04 | 0.92 | 0.98 | 0.97 | 1.08 |
| Leptin | 0.80 | 0.82 | 1.18 | 1.20 | 1.06 | 0.97 | 0.89 | 1.16 |
| Lipoprotein (a) | 1.19 | 1.24 | 1.35 | 1.28 | 1.27 | 1.26 | 0.59 | 0.91 |
| MCP-1 | 1.10 | 1.13 | 0.99 | 1.03 | 1.18 | 1.28 | 1.20 | 1.34 |
| MDC | 0.79 | 0.70 | 0.71 | 0.78 | 0.79 | 0.81 | 1.01 | 1.22 |
| MIP-1beta | 1.04 | 0.99 | 0.97 | 1.01 | 1.18 | 1.09 | 1.41 | 1.47 |
| MMP-3 | 1.00 | 1.00 | 1.00 | 1.00 | 1.00 | 1.00 | 0.94 | 1.26 |
| MMP-9 | 0.71 | 0.72 | 1.40 | 1.34 | 0.81 | 0.81 | 1.24 | 2.21 |
| Myglobin | 0.77 | 0.82 | 1.19 | 1.32 | 0.58 | 0.56 | 0.84 | 0.96 |
| Prostatic Acid Phosphatase | 1.00 | 1.00 | 1.00 | 1.00 | 1.00 | 1.00 | 1.00 | 1.00 |
| Prostate Specific Antigen, Free | 1.28 | 1.40 | 1.61 | 1.62 | 1.85 | 1.86 | 0.76 | 1.15 |
| RANTES | 0.71 | 0.87 | 0.71 | 0.68 | 0.90 | 0.80 | 0.82 | 0.97 |
| Serum Amyloid P | 0.64 | 0.67 | 0.87 | 0.73 | 0.57 | 0.52 | 0.81 | 0.95 |
| SGOT | 0.70 | 0.76 | 0.61 | 0.56 | 0.61 | 0.70 | 0.83 | 0.93 |
| Thyroxine Binding Globulin | 0.44 | 0.46 | 0.40 | 0.43 | 0.49 | 0.51 | 0.86 | 0.95 |
| TIMP-1 | 0.79 | 0.82 | 0.86 | 0.95 | 0.94 | 0.94 | 0.83 | 0.96 |
| Thrombopoietin | 1.00 | 1.00 | 1.00 | 1.00 | 1.00 | 1.00 | 1.00 | 1.00 |
| Thyroid Stimulating Hormone | 1.11 | 1.14 | 1.24 | 1.15 | 1.35 | 1.24 | 0.95 | 1.17 |
| von Willebrand Factor | 0.19 | 0.24 | 0.12 | 0.13 | 0.14 | 0.14 | 0.53 | 0.65 |

GV1 = NOTHING
GV2 = TE
GV3 = TE + NP40 (SG)
GV4 = TREH
GV5 = TE + TREH
GV6 = SG + TREH
GV7 = TE + CYST
GV8 = SG + CYST

The results illustrated in Tables 5 to 7 and FIGS. 4 to 30 indicate that numerous proteins are present in the sample recovered from sponge, after long-term storage. The finding that proteins are present at detectable quantities indicates that the proteins can be detected and quantified in a sample recovered from sponge without the need to concentrate or enrich or purify the recovered protein. Thus, protein recovered from sponge can be directly subjected to analysis requiring proteins to be present above minimal concentrations, without the need for further enrichment, purification or concentration of the recovered protein.

The results in Table 4 indicate that the treatments providing the greatest preservation of stored peptide are Treatments #3 and #6. These treatments provided the best overall recovery of proteins, and for antibody detection of the trace proteins.

The electrophoresis results illustrated in FIGS. 34 and 35 indicate that protein stored using 12 sponge material was not significantly degraded. Thus, protein storage using sponge substrates can be used to preserve proteins, and is applicable where high quality recovered protein is required for a subsequent analysis or application.

In order to determine the reproducibility of protein recovery, the concentration of eluted serum protein was analyzed at several times over a two month period. An average of these data was obtained and an estimate of variability which was the one SD from the mean, presented as a 18 percentage relative to the mean (see the Table immediately below). Variability over 2 months of sampling was observed to be in the +/−7% to +/−14% range. This relatively small variability is comparable to values that would be obtained for frozen samples over the same time period, due to pipetting error and error in the fluorimetric BCA protein determination method. Thus, protein recovery from sponge substrate was reproducible.

Quantitative Protein Recovery Data for the Various Treatments

| SAMPLE TYPE | Protein Recovery Concentration | *avg % recovery (One SD of the Mean) |
|---|---|---|
| Fresh Control Serum | 106 mg/ml | Reference |
| Frozen Control Serum | 102 mg/ml | 98.3% (11) |
| No Treatment | 85.2 mg/ml | 81% (12) |
| Treatment 1 | 108 mg/ml | 99.5% (7) |
| Treatment 2 | 118 mg/ml | 101% (14) |
| Treatment 3 | 75.2 mg/ml | 64.3% (9) |
| Treatment 4 | 63.2 mg/ml | 61.3% (13) |
| Treatment 5 | 125 mg/ml | 96% (11) |
| Treatment 6 | 85.2 mg/ml | 79.8% (8) |
| Treatment 7 | 110 mg/ml | 98.3% (15) |

*The values in the above Table are estimates based upon averaging 5 samples and pooling of performance over serial collections during 2 months. Recovery variability will be diminished by optimizing the mechanical aspects of hydration and elution.

The relatively lower apparent recovery data for treatments 3, 4, and 5 is a quantitative artifact due to a skewing created by the different method used for fluorimetric quantitation (BCA) resulting from interaction of the protein-dye complex with the additives present in these treatments. This conclusion is based upon the relative lowering of those signals relative to fresh or other air-dried sample treatments seen immediately upon drying and is not time dependent thereafter over six months.

The apparently-artifact of lowering (about 30-40%) due to not repeatedly compressing the sponge prior to recovery of the liquid is confirmed secondarily via quantitative PAGE electrophoresis and by the bead-based immunoassay from Rules Based Medicine (Austin Tex.), neither of which reveal any evidence for systematic diminishment of protein mass in Treatments 3, 4, or 5 relative to the other treatments. Consequently, Treatments 3, 4, and 5 are likely to also provide preservation of stored peptide.

The data is for simple water extraction without compression of the sponge so yields are lower compared to protocols in which sponge is compressed. Treatment 4, for example provides similar yields to Treatments 1 and 2 using when compressing the sponge several times during elution.

Example 7

This example includes studies in which blood sample absorbed to an elutable elastomeric substrate was stored for various times and subsequently eluted, recovered and analyzed. The exemplary study employs two sequential steps: 1) elution of protein from blood absorbed to polyester sponge; and 2) elution of nucleic acid from blood absorbed to the same polyester sponge.

Two-Step Elution and Recovery of Protein and Nucleic Acid from a Blood Sample Absorbed to Sponge In this study, blood absorbed to a polyester sponge was stored for 167 days. Following storage, protein was eluted and recovered from the sponge substrate followed by elution and recovery of nucleic acid from the same sponge substrate.

A polyurethane (e.g., polyester) sponge (a 6 mm×5 mm cylinder) with various treatments (see below) was absorbed with a blood sample and stored at room temperature for various amounts of time. After storage for 167 days, the blood-absorbed sponge was hydrated with water (150 ul) and protein eluted by compressing the sponge contained in a vessel with a plunger. Following protein elution, sponge was hydrated with an alkaline elution liquid (pH 11.7-11.), compressed multiple times, incubated at room temperature (30 min), and compressed again multiple times. This process was repeated, eluates combined and analyzed. The two-step elution and recovery procedure is essentially as described in Example 4.

Figure 36:
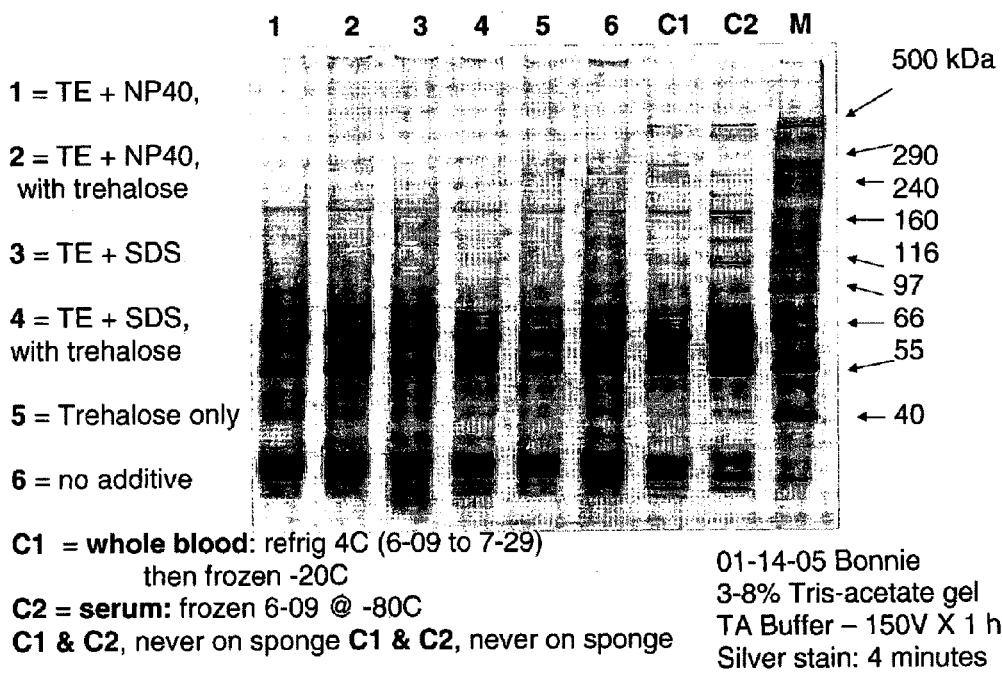
FIG. 36 is a gel electrophoresis result of the total recovered protein eluted from a polyester sponge used to absorb blood and stored for 167 days.
Figure 37:
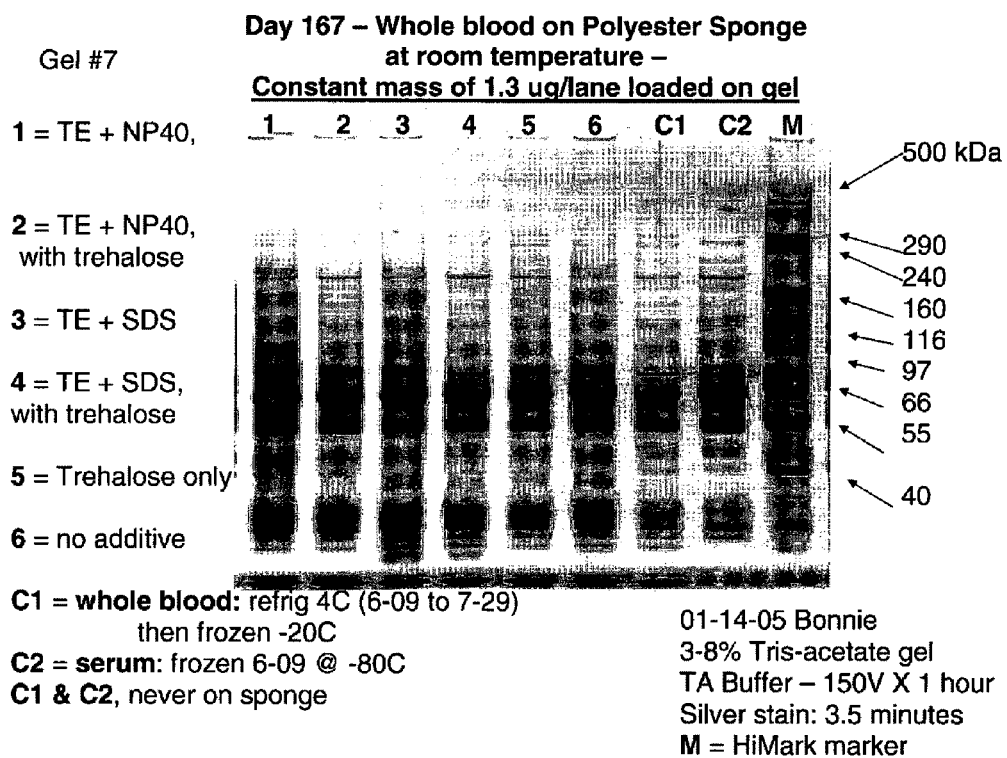
FIG. 37 is a gel electrophoresis result of the total recovered protein eluted from a polyester sponge used to absorb blood and stored for 167 days.

The protein eluate recovered from the stored sample was subsequently analyzed quantitatively and qualitatively. In particular, the total recovered protein in the eluate was determined using a BCA analysis, as previously described. The total recovered protein in the eluate was also qualitatively analyzed by electrophoresis and silver staining. These results are illustrated in FIGS. 36 and 37.

Yield of Total Protein Recovered (ug/ml) from Sponge Stored for 167 Days Using Various Treatments (in Approximately 120 uL volume), as Determined by BCA

| | |
|---|---|
| Treatment #1 = TE + NP40 = | 150.914 |
| Treatment #2 = TE + NP40 + trehalose = | 197.959 |
| Treatment #3 = TE + SDS = | 165.175 |
| Treatment #4 = TE + SDS + trehalose = | 177.038 |
| Treatment #5 = Trehalose only = | 148.897 |
| Treatment #6 = no additive = | 154.525 |
| Control C1 = whole blood frozen = | 191.028 |
| Control C2 = serum frozen = | 113.733 |

The nucleic acid eluate recovered from the stored sample in the second elution step was subsequently analyzed quantitatively and qualitatively. In particular, the amount of DNA present in the eluate was determined using a semi-quantitative polymerase chain reaction (PCR). Briefly, DNA eluate was diluted 10-fold into a standard 50 μL PCR reaction, containing an oligonucleotide PCR primer pair specific for the human amelogenin gene, which yields a single 558 bp PCR product. As positive quantitative controls, a series of serially diluted purified human DNA samples were also analyzed at 10 ng, 1 ng, 0.1 ng, 0.01 ng per reaction. Forty cycles of PCR were performed and the eluate DNA was compared to the known human DNA samples. The comparison was performed by subjecting 5 µL of each PCR reaction to 5% acrylamide electrophoresis. The resulting electophoresis pattern (i.e. a single 558 by band per sample) was visualized by fluorescent staining with ethidium bromide and data acquisition with a CCD. The resulting digitals from the electrophoresis bands were compared, and the DNA concentration in the eluates was estimated by interpolation of the mass concentration of the known standards, based upon the validated assumption that the ratio of PCR product yields was proportional to the ratio of DNA mass in the original samples. In this assay, the calculated DNA yields are estimated to be accurate to within about +/−30%. In the Table below, Q1 and Q2 refer to duplicate measurements of the amount of DNA in the original 150 uL of blood that had been absorbed to the sponge. These values (Q1, Q2) were obtained by processing of 150 uL of the blood (in duplicate) via column chromatography using a QiaAmp-mini product (Qiagen). Based on those un-dried references, about ½ of the applied blood DNA was recovered from elastomeric substrate with treatments #2 and #5. Other treatments yielded relatively lower recovery.

The recovered DNA present in the eluate was also qualitatively analyzed by gel electrophoresis and staining. These results are illustrated in FIG. 38.

Yield of Total DNA (Per 150 uL) Recovered from Sponge Following Storage for 167 Days, as Determined by Semi Quantitative PCR (in Nanograms)

| | |
|---|---|
| Treatment #1 = TE + NP40 = | 100 ng |
| Treatment #2 = TE + NP40 + trehalose = | 750 ng |
| Treatment #3 = TE + SDS = | 10 ng |
| Treatment #4 = TE + SDS + trehalose = | 100 ng |
| Treatment #5 = Trehalose only = | 750 ng |
| Treatment #6 = no additive = | 100 ng |
| Control Q1 = whole blood frozen = | 1500 ng |
| Control Q2 = whole blood frozen = | 1500 ng |

The results above indicate that stable protein could be recovered from substrate following prolonged room temperature storage. Recovered protein appeared identical to protein of frozen whole blood control, as assessed by polyacrylamide gel electrophoresis (PAGE). For all treatments, greater than 80% of the protein was recovered from substrate. Thus, elutable elastomeric substrate provides a reliable means to store protein in a form that resists degradation.

The results above also indicate that DNA can be stored long-term in a preserved form that resists degradation. The DNA is therefore suitable for analysis or application requiring high quality non-degraded DNA, such as amplification, sequencing and cloning. Furthermore, the recovered DNA could directly be used in PCR, which is sensitive to the presence of protein contaminants. Thus, the recovered DNA need not be subjected to phenol:chloroform extraction or other techniques for removing protein contaminants prior to use in PCR and other such methods where protein contaminants may interfere with the procedure.

Recovery of DNA varied depending on the treatment. Treatments #2 (NP40-Trehalose) and #5 (Trehalose added alone) provided the best DNA recovery and Treatment #6 (untreated polyester sponge), also provided effective DNA recovery. Recovery for each of Treatments #2 and #5 was approximately 50% (750 ng DNA) per substrate unit. Trehalose appears to enhance DNA recovery, but does not appear to significantly improve protein recovery under the studied conditions. Sucrose like trehalose may also enhance recovery of nucleic acid.

What is claimed is:

1. A storage unit having
   a plurality of compartments, each compartment having a physical size sufficient for holding an elutable porous or semi-porous elastomeric substrate, and
   an elutable porous or semi-porous elastomeric substrate comprised in a compartment,
       wherein said elutable porous or semi-porous elastomeric substrate comprises a material selected from the group consisting of polyester, polystyrene, polyurethane, and polyvinyl alcohol (PVA), and
       wherein a peptide or a nucleic acid is absorbed to said elutable porous or semi-porous elastomeric substrate.

2. The storage unit of claim 1, further comprising instructions for eluting or recovering an absorbed peptide or absorbed nucleic acid from the elutable porous or semi-porous elastomeric substrate.

3. The storage unit of claim 1, further comprising instructions for preparing an aqueous liquid for eluting or recovering an absorbed peptide or absorbed nucleic acid from the elutable porous or semi-porous elastomeric substrate.

4. The storage unit of claim 1, wherein each of said plurality of compartments is a well in a multi-well plate.

5. The storage unit of claim 1, wherein the peptide or the nucleic acid absorbed to the porous or semi-porous elastomeric substrate has higher resistance to degradation than a peptide or a nucleic acid not absorbed to the porous or semi-porous elastomeric substrate.

6. The storage unit of claim 1, wherein the porous or semi-porous elastomeric substrate comprising the peptide or the nucleic acid absorbed thereto contains less than 25% water by mass relative to the total mass of the absorbed substrate.

7. The storage unit of claim 1, wherein at least 30% of the peptide or the nucleic acid absorbed to the porous or semi-porous elastomeric substrate is recoverable from the substrate.

8. The storage unit of claim 1, wherein the porous or semi-porous elastomeric substrate is a foam or a sponge.

9. The storage unit of claim 1, wherein the material comprising the porous or semi-porous elastomeric substrate is reversibly compressible to at least ½ of the volume of the material in a non-compressed state.

10. The storage unit of claim 1, wherein the material comprising the porous or semi-porous elastomeric substrate is reversibly expandable to at least 2-fold the volume of the material in a non-expanded state.

11. The storage unit of claim 1, wherein the porous or semi-porous elastomeric substrate further comprises a substance selected from the group consisting of buffers, chelating agents, denaturing agents, detergents, reducing agents, antioxidants, preservatives, stabilizing agents, protease inhibitors, nuclease inhibitors, anti-microbials, and low-water uptake saccharides.

* * * * *